(12) United States Patent
Coates

(10) Patent No.: US 11,013,554 B2
(45) Date of Patent: May 25, 2021

(54) CATHETER APPARATUSES FOR MODULATION OF NERVES IN COMMUNICATION WITH PULMONARY SYSTEM AND ASSOCIATED SYSTEMS AND METHODS

(71) Applicant: MEDTRONIC ARDIAN LUXEMBOURG S.A.R.L., Luxembourg (LU)

(72) Inventor: Paul Coates, Santa Rosa, CA (US)

(73) Assignee: MEDTRONIC ARDIAN LEXEMBOURG S.A.R.L., Luxembourg (LU)

( * ) Notice: Subject to any disclaimer, the term of this patent is extended or adjusted under 35 U.S.C. 154(b) by 216 days.

(21) Appl. No.: 15/515,977

(22) PCT Filed: Nov. 13, 2015

(86) PCT No.: PCT/IB2015/002240
§ 371 (c)(1),
(2) Date: Mar. 30, 2017

(87) PCT Pub. No.: WO2016/075536
PCT Pub. Date: May 19, 2016

(65) Prior Publication Data
US 2018/0185090 A1    Jul. 5, 2018

Related U.S. Application Data

(60) Provisional application No. 62/080,189, filed on Nov. 14, 2014, provisional application No. 62/080,248, (Continued)

(51) Int. Cl.
*A61B 18/14* (2006.01)
*A61B 18/02* (2006.01)
(Continued)

(52) U.S. Cl.
CPC ...... *A61B 18/1492* (2013.01); *A61B 18/0206* (2013.01); *G01R 5/26* (2013.01);
(Continued)

(58) Field of Classification Search
CPC ...... A61B 17/0206; A61B 2018/00577; A61B 2018/0212; A61B 2018/00375;
(Continued)

(56) References Cited

U.S. PATENT DOCUMENTS 4,602,624 A    7/1986  Naples et al.
4,649,936 A    3/1987  Ungar et al.
(Continued)

FOREIGN PATENT DOCUMENTS

EP    2701795         3/2014
WO    WO1994007446    4/1994
(Continued)

OTHER PUBLICATIONS

U.S. Appl. No. 95/002,110, filed Aug. 29, 2010, Demarais, et al.
(Continued)

*Primary Examiner* — Linda C Dvorak
*Assistant Examiner* — Annabeth E Rodriguez

(57) ABSTRACT

Devices and systems for the selective positioning of an intravascular neuromodulation device are disclosed herein. Such systems can include, for example, an elongated shaft and a therapeutic assembly carried by a distal portion of the elongated shaft. The therapeutic assembly is configured for delivery within a blood vessel. The therapeutic assembly can include one or more energy delivery elements configured to deliver therapeutic energy to nerves proximate a vessel wall.

18 Claims, 32 Drawing Sheets

Related U.S. Application Data filed on Nov. 14, 2014, provisional application No. 62/082,635, filed on Nov. 21, 2014.

(51) Int. Cl.
  *A61B 18/00* (2006.01)
  *G01R 5/26* (2006.01)
  *A61N 7/00* (2006.01)
  *A61B 90/00* (2016.01)

(52) U.S. Cl.
  CPC ............ *A61B 2018/0022* (2013.01); *A61B 2018/0025* (2013.01); *A61B 2018/00148* (2013.01); *A61B 2018/00214* (2013.01); *A61B 2018/00255* (2013.01); *A61B 2018/00267* (2013.01); *A61B 2018/00279* (2013.01); *A61B 2018/00351* (2013.01); *A61B 2018/00375* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 2018/0212* (2013.01); *A61B 2018/0262* (2013.01); *A61B 2018/1407* (2013.01); *A61B 2090/3966* (2016.02); *A61B 2218/002* (2013.01); *A61N 2007/0026* (2013.01)

(58) Field of Classification Search
  CPC ...... A61B 2018/00214; A61B 18/1492; A61B 17/22; A61B 18/14; A61B 2017/00292; A61B 2017/00296; A61B 2017/003; A61B 2017/00336; A61B 2017/0034; A61B 2017/00305; A61B 2017/00318; G01R 5/26
  See application file for complete search history.

(56) References Cited

U.S. PATENT DOCUMENTS

| | | | |
|---|---|---|---|
| 4,709,698 A | 12/1987 | Johnston et al. | |
| 4,764,504 A | 8/1988 | Johnson et al. | |
| 4,890,623 A | 1/1990 | Cook et al. | |
| 4,976,711 A | 12/1990 | Parins et al. | |
| 5,297,564 A | 3/1994 | Love | |
| 5,300,068 A | 4/1994 | Rosar et al. | |
| 5,333,614 A | 8/1994 | Feiring | |
| 5,358,514 A | 10/1994 | Schulman et al. | |
| 5,368,591 A | 11/1994 | Lennox et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,626,576 A | 5/1997 | Janssen | |
| 5,647,361 A * | 7/1997 | Damadian | A61B 5/055 128/897 |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,772,590 A | 6/1998 | Webster, Jr. | |
| 5,823,956 A | 10/1998 | Roth et al. | |
| 5,824,031 A * | 10/1998 | Cookston | A61M 25/01 607/122 |
| 5,829,447 A | 11/1998 | Stevens et al. | |
| 5,855,614 A | 1/1999 | Stevens et al. | |
| 5,860,974 A | 1/1999 | Abele | |
| 5,865,787 A | 2/1999 | Shapland | |
| 5,891,138 A | 4/1999 | Tu et al. | |
| 5,893,885 A | 4/1999 | Webster, Jr. | |
| 5,924,424 A | 7/1999 | Stevens et al. | |
| 5,944,710 A | 8/1999 | Dev et al. | |
| 5,954,719 A | 9/1999 | Chen et al. | |
| 5,983,141 A | 11/1999 | Sluijter et al. | |
| 6,004,269 A | 12/1999 | Crowley et al. | |
| 6,009,877 A | 1/2000 | Edwards | |
| 6,024,740 A | 2/2000 | Lesh et al. | |
| 6,036,687 A | 3/2000 | Laufer et al. | |
| 6,066,134 A | 5/2000 | Eggers et al. | |
| 6,079,414 A | 6/2000 | Roth | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,142,993 A | 11/2000 | Whayne et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,237,605 B1 | 5/2001 | Vaska et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,309,399 B1 | 10/2001 | Barbut et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,405,732 B1 | 6/2002 | Edwards et al. | |
| 6,413,255 B1 | 7/2002 | Stern | |
| 6,488,679 B1 | 12/2002 | Swanson et al. | |
| 6,506,189 B1 | 1/2003 | Rittman et al. | |
| 6,514,226 B1 | 2/2003 | Levin et al. | |
| 6,522,926 B1 | 2/2003 | Kieval et al. | |
| 6,542,781 B1 | 4/2003 | Koblish et al. | |
| 6,562,034 B2 | 5/2003 | Edwards et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,640,120 B1 | 10/2003 | Swanson et al. | |
| 6,651,672 B2 | 11/2003 | Roth | |
| 6,679,268 B2 | 1/2004 | Stevens et al. | |
| 6,685,648 B2 | 2/2004 | Flaherty et al. | |
| 6,711,444 B2 | 3/2004 | Koblish | |
| 6,736,835 B2 | 5/2004 | Pellegrino et al. | |
| 6,752,805 B2 | 6/2004 | Maguire et al. | |
| 6,845,267 B2 | 1/2005 | Harrison et al. | |
| 6,850,801 B2 | 2/2005 | Kieval et al. | |
| 6,869,431 B2 | 3/2005 | Maguire et al. | |
| 6,885,888 B2 | 4/2005 | Rezai | |
| 6,893,436 B2 | 5/2005 | Woodard et al. | |
| 6,917,834 B2 | 7/2005 | Koblish et al. | |
| 6,923,808 B2 | 8/2005 | Taimisto | |
| 6,939,346 B2 | 9/2005 | Kannenberg et al. | |
| 6,949,097 B2 | 9/2005 | Stewart et al. | |
| 6,955,175 B2 | 10/2005 | Stevens et al. | |
| 6,960,207 B2 | 11/2005 | Vanney et al. | |
| 7,087,026 B2 | 8/2006 | Callister et al. | |
| 7,087,053 B2 | 8/2006 | Vanney | |
| 7,100,614 B2 | 9/2006 | Stevens et al. | |
| 7,149,574 B2 | 12/2006 | Yun et al. | |
| 7,162,303 B2 | 1/2007 | Levin et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,584,004 B2 | 9/2009 | Caparso et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 7,819,866 B2 | 10/2010 | Bednarek | |
| 8,131,371 B2 | 3/2012 | Demarais et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |

(56) References Cited

U.S. PATENT DOCUMENTS

| | | | |
|---|---|---|---|
| 8,500,733 B2 * | 8/2013 | Watson | A61B 18/1492 606/41 |
| 8,740,895 B2 | 6/2014 | Mayse et al. | |
| 8,777,943 B2 | 7/2014 | Mayse et al. | |
| 8,798,738 B2 | 8/2014 | Machado et al. | |
| 9,028,391 B2 | 5/2015 | Gnanashanmugam et al. | |
| 2002/0139379 A1 | 10/2002 | Edwards et al. | |
| 2002/0165532 A1 | 11/2002 | Hill, III et al. | |
| 2002/0183682 A1 | 12/2002 | Darvish et al. | |
| 2003/0050635 A1 | 3/2003 | Truckai et al. | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0125790 A1 | 7/2003 | Fastovsky et al. | |
| 2003/0181897 A1 | 9/2003 | Thomas et al. | |
| 2003/0199863 A1 | 10/2003 | Swanson et al. | |
| 2003/0216792 A1 | 11/2003 | Levin et al. | |
| 2003/0229340 A1 | 12/2003 | Sherry et al. | |
| 2003/0233099 A1 | 12/2003 | Danek et al. | |
| 2004/0010289 A1 | 1/2004 | Biggs et al. | |
| 2004/0019348 A1 | 1/2004 | Stevens et al. | |
| 2004/0054363 A1 * | 3/2004 | Vaska | A61B 17/22012 606/27 |
| 2004/0117032 A1 | 6/2004 | Roth | |
| 2004/0215186 A1 | 10/2004 | Cornelius et al. | |
| 2005/0080409 A1 | 4/2005 | Young et al. | |
| 2005/0096647 A1 | 5/2005 | Steinke et al. | |
| 2005/0187579 A1 | 8/2005 | Danek et al. | |
| 2005/0228460 A1 | 10/2005 | Levin et al. | |
| 2005/0288730 A1 | 12/2005 | Deem et al. | |
| 2006/0085054 A1 | 4/2006 | Zikorus et al. | |
| 2006/0095029 A1 | 5/2006 | Young et al. | |
| 2006/0100618 A1 | 5/2006 | Chan et al. | |
| 2006/0206150 A1 | 9/2006 | Demarais et al. | |
| 2006/0271111 A1 | 11/2006 | Demarais et al. | |
| 2007/0129720 A1 | 6/2007 | Demarais et al. | |
| 2007/0265687 A1 | 11/2007 | Deem et al. | |
| 2008/0319513 A1 | 12/2008 | Pu et al. | |
| 2009/0036948 A1 | 2/2009 | Levin et al. | |
| 2009/0299355 A1 | 12/2009 | Bencini et al. | |
| 2010/0023088 A1 | 1/2010 | Stack et al. | |
| 2010/0137860 A1 | 6/2010 | Demarais et al. | |
| 2010/0137952 A1 | 6/2010 | Demarais et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2012/0116382 A1 | 5/2012 | Ku et al. | |
| 2012/0130289 A1 | 5/2012 | Demarais et al. | |
| 2012/0130345 A1 | 5/2012 | Levin et al. | |
| 2012/0143179 A1 | 6/2012 | Avitall | |
| 2012/0172837 A1 | 7/2012 | Demarais et al. | |
| 2013/0090649 A1 | 4/2013 | Smith et al. | |
| 2013/0310822 A1 | 11/2013 | Mayse et al. | |
| 2014/0142408 A1 | 5/2014 | De La Rama et al. | |
| 2014/0148883 A1 | 5/2014 | Stack et al. | |
| 2014/0180277 A1 | 6/2014 | Chen | |
| 2014/0221975 A1 | 8/2014 | Gnanashanmugam et al. | |
| 2014/0228614 A1 | 8/2014 | Stopek | |
| 2014/0228858 A1 | 8/2014 | Stopek | |
| 2014/0243807 A1 | 8/2014 | Margolis | |
| 2014/0276724 A1 | 9/2014 | Goshayeshgar | |
| 2014/0276728 A1 | 9/2014 | Goshayeshgar | |
| 2014/0276792 A1 | 9/2014 | Kaveckis et al. | |
| 2014/0364926 A1 | 12/2014 | Nguyen et al. | |

FOREIGN PATENT DOCUMENTS

| | | | |
|---|---|---|---|
| WO | WO1995025472 | 9/1995 | |
| WO | WO1995031142 | 11/1995 | |
| WO | WO1997036548 | 10/1997 | |
| WO | WO1998017190 | 4/1998 | |
| WO | WO1998042403 | 10/1998 | |
| WO | WO-9900060 A1 * | 1/1999 | A61B 18/1492 |
| WO | WO1999000060 | 1/1999 | |
| WO | WO2001022897 | 4/2001 | |
| WO | WO2001070114 | 9/2001 | |
| WO | WO2003022167 | 3/2003 | |
| WO | WO2003082080 | 10/2003 | |
| WO | WO2005030072 | 4/2005 | |
| WO | WO2005041748 | 5/2005 | |
| WO | WO2005110528 | 11/2005 | |
| WO | WO2006041881 | 4/2006 | |
| WO | WO2006105121 | 10/2006 | |
| WO | WO2007008954 | 1/2007 | |
| WO | WO2007078997 | 7/2007 | |
| WO | WO2008049084 | 4/2008 | |
| WO | WO2010056771 | 5/2010 | |
| WO | WO2012057915 | 5/2012 | |
| WO | WO2014124241 | 8/2014 | |
| WO | WO2014150204 | 9/2014 | |
| WO | WO2014160422 | 10/2014 | |
| WO | WO2014189887 | 11/2014 | |

OTHER PUBLICATIONS

U.S. Appl. No. 95/002,209, filed Sep. 13, 2012, Levin, et al.
U.S. Appl. No. 95/002,233, filed Sep. 13, 2012, Levin, et al.
U.S. Appl. No. 95/002,243, filed Sep. 13, 2012, Levin, et al.
U.S. Appl. No. 95/002,253, filed Sep. 13, 2012, Demarais, et al.
U.S. Appl. No. 95/002,255, filed Sep. 13, 2012, Demarais, et al.
U.S. Appl. No. 95/002,292, filed Sep. 14, 2012, Demarais, et al.
U.S. Appl. No. 95/002,327, filed Sep. 14, 2012, Demarais, et al.
U.S. Appl. No. 95/002,335, filed Sep. 14, 2012, Demarais, et al.
U.S. Appl. No. 95/00,336, filed Sep. 14, 2012, Levin, et al.
U.S. Appl. No. 95/002,356, filed Sep. 14, 2012, Demarais, et al.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Dibona, et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.

(56) References Cited

OTHER PUBLICATIONS

Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
OZ, Mehmet, Pressure Relief, Time, Jan. 9, 2012, 2 pages. <www.time.com/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.

(56) References Cited

OTHER PUBLICATIONS

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n. I.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison AwardsIm" Edison Awards: Honoring Innovations & Innovators, 2013, 2 pp., <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Curtis, et al., "Surgical therapy for persistent hypertension after renal transplantation." Transplantation, 1981, 31: 125-128.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Doumas, Michael et al., "Renal Nerve Ablation for Resistant Hypertension: The Dust Has Not Yet Settled." The Journal of Clinical Hypertension. 2014; vol. 16, No. 6, 2 pages.

Dubuc, M., et al., "Feasibility of cardiac cryoablation using a transvenous steerable electrode catheter." J Intery Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR 8: 527-533 (1997).

Hall, W. H., et al. "Combined embolization and percutaneous radiofrequency ablation of a solid renal tumor." Am. J. Roentgenol,174: 1592-1594 (2000).

Han, Y.-M, et al., "Renal artery embolization with diluted hot contrast medium: An experimental study." J Vasc Intery Radiol, 12: 862-868 (2001).

Hansen, J. M., et al. "The transplanted human kidney does not achieve functional reinnervation." Clin. Sci, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Messerli, Franz H. et al. "Renal Denervation for Resistant Hypertension: Dead or Alive?" Healio: Cardiology today's Intervention, May/Jun. 2014, 2 pages.

Millard, F. C., et al, "Renal Embolization for ablation of function in renal failure and hypertension." Postgraduate Medical Journal, 65, 729-734, (1989).

Miller, Reed, "Finding A Future for Renal Denervation With Better Controlled Trials." Pharma & Medtech Business Intelligence, Article # 01141006003, Oct. 6, 2014, 4 pages.

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

(56) References Cited

OTHER PUBLICATIONS

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Papademetriou, Vasilios et al., "Catheter-Based Renal Denervation for Resistant Hypertension: 12-Month Results of the EnligHTN 1 First-in-Human Study Using a Multielectrode Ablation System." Hypertension. 2014; 64: 565-572.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Smithwick et al., "Splanchnicectomy for Essential Hypertension." J. Am. Med. Assn. 152:16 (1953), pp. 1501-04.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversable renal denervation on haemodynamic and excretory functions on the ipsilateral and contralateral kidney in the cat." Hypertension, 4: 181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Valente, "Laparoscopic renal denervation for intractable ADPKS-related pain." Nephrol Dial Transplant, 16: 160 (2001).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Chen, "Pulmonary artery denervation for pulmonary hypertention: results from PADN-I study and future studies." Cardiovascular Research Foundation, Nanjing First Hospital, Nanjing Medical University, powerpoint, 2013, 11pages.

Rothman, "Pulmonary Artery Denervation for the Treatment of Pulmonary Hypertension." Cardiovascular Research Foundation, The University of Sheffield, powerpoint, 2013, 22 pages.

Sobotka, P. "Sympathetic Modification in Heart Failure and Hypertension." TCT 25 Cardiovascular Research Foundation, 28 pages. (No date).

Search Report and Written Opinion dated Jan. 9, 2015 for PCT Application No. PCT/US2014/062060.

Search Report and Written Opinion dated Jan. 21, 2015 for PCT Application No. PCT/US2014/062055.

Search Report and Written Opinion dated Nov. 9, 2016 for PCT Application No. PCT/IB2015/002313.

Search Report and Written Opinion dated Sep. 11, 2016 for PCT Application No. PCT/IB2015/002313.

Search Report dated Feb. 20, 2017 for PCT Application No. PCT/IB2015/002240.

Search Report dated Oct. 17, 2013 for European Application No. 13159256.

* cited by examiner

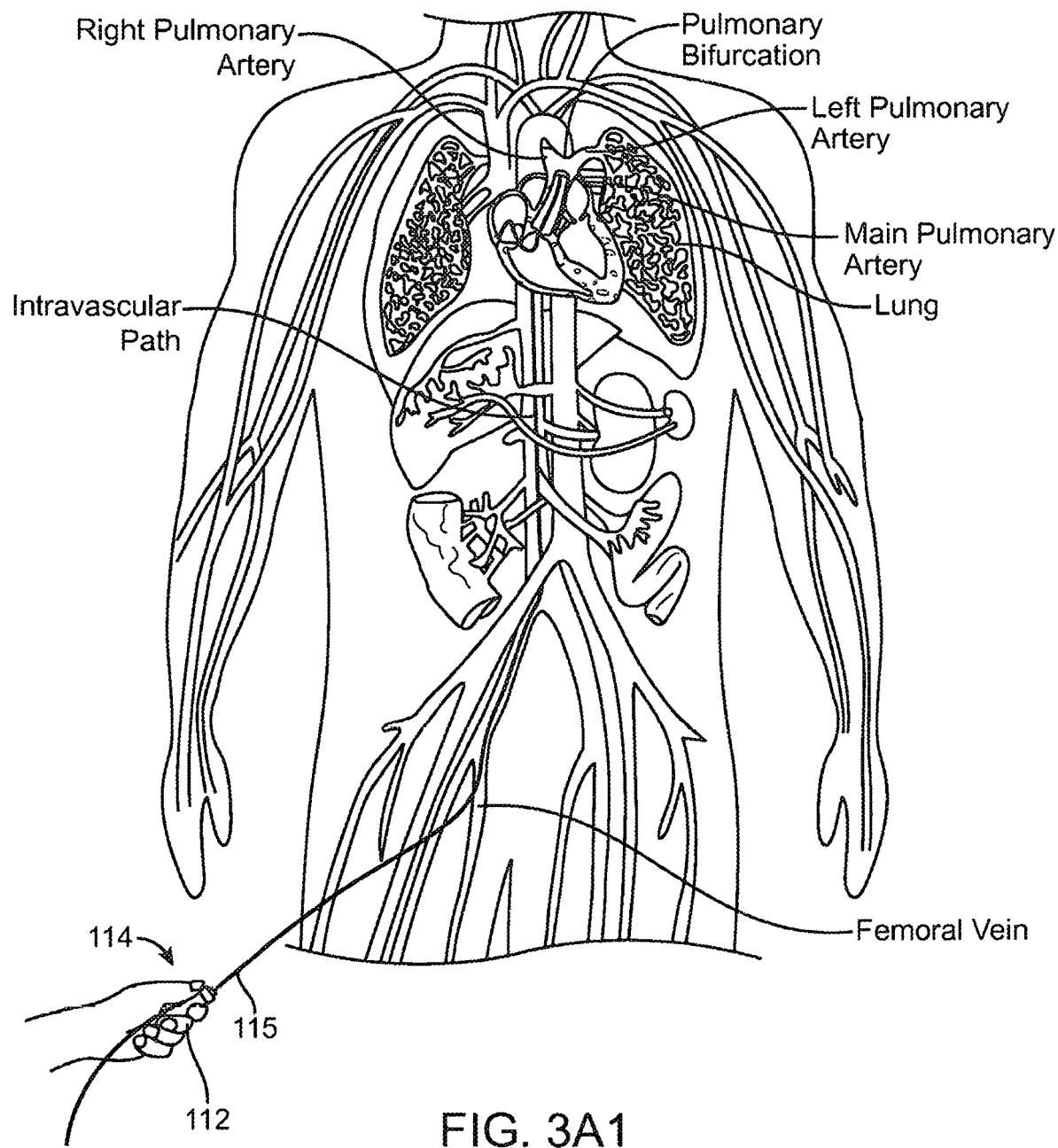
FIG. 3A1

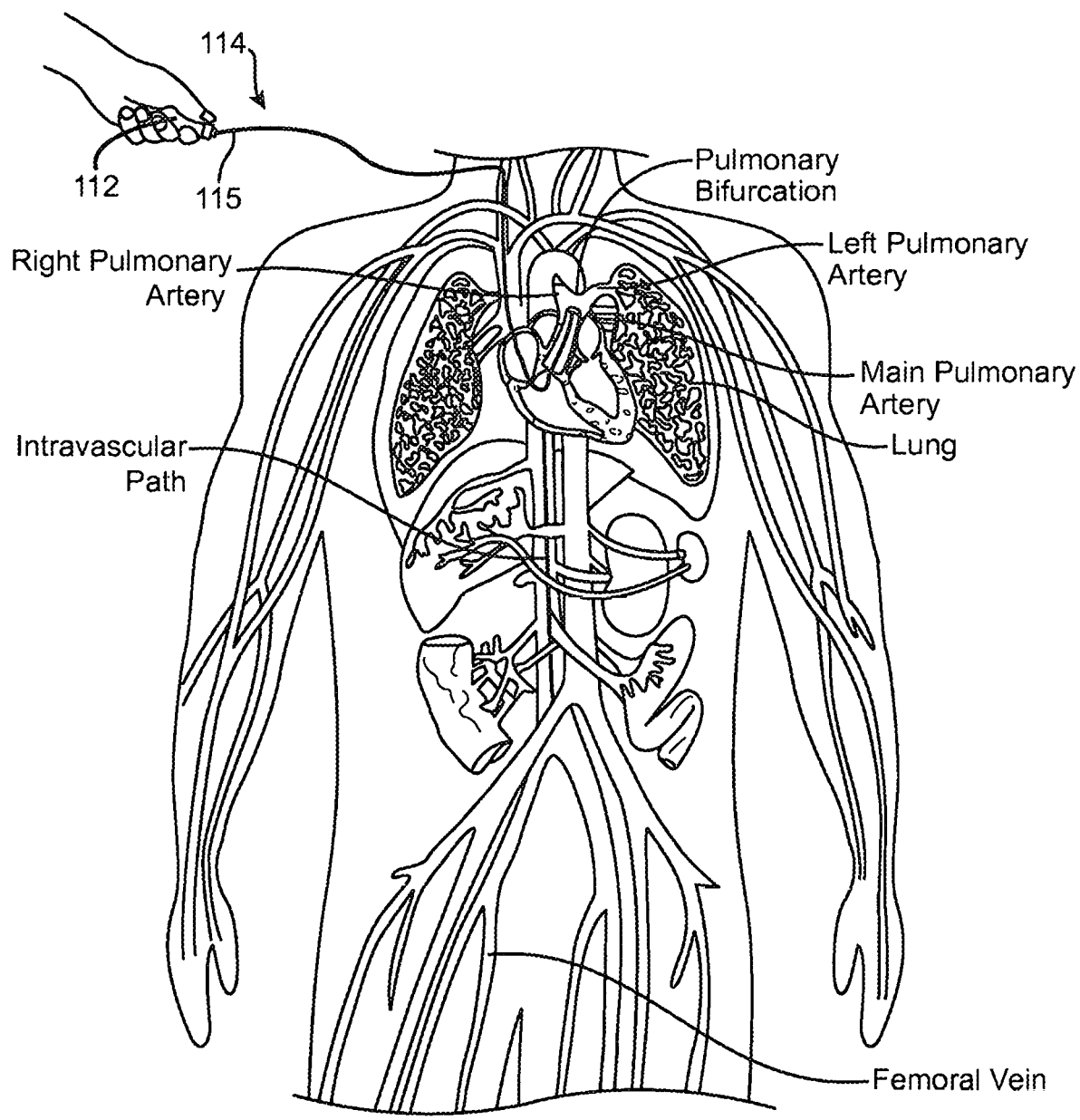
FIG. 3A2

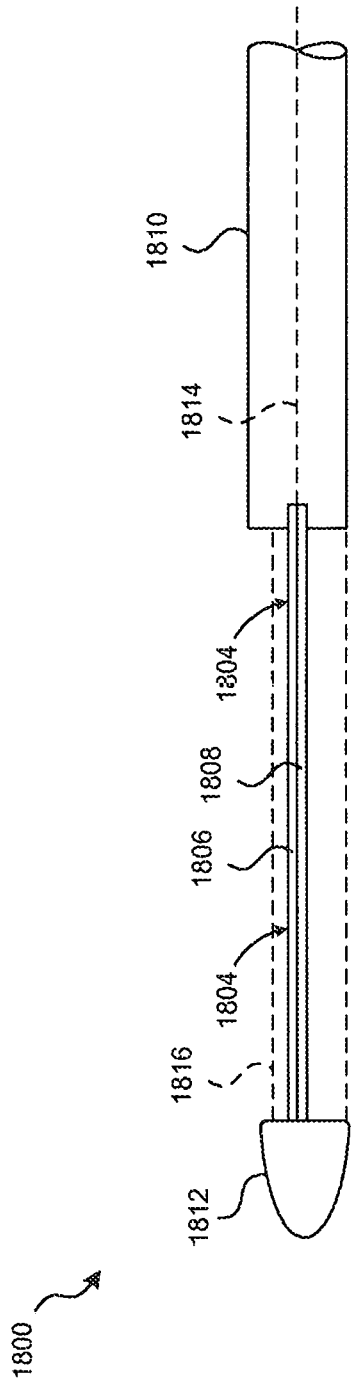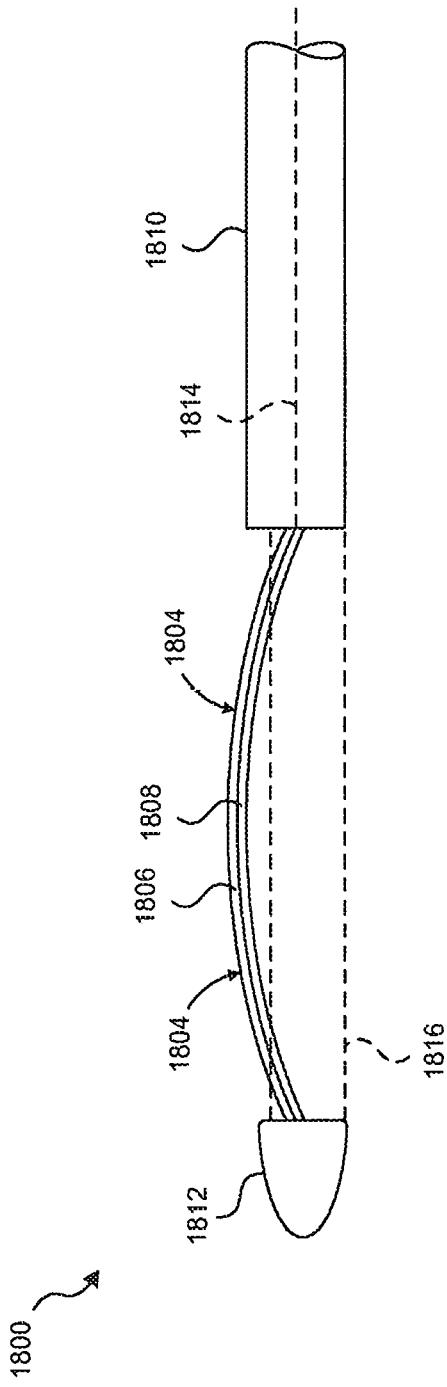

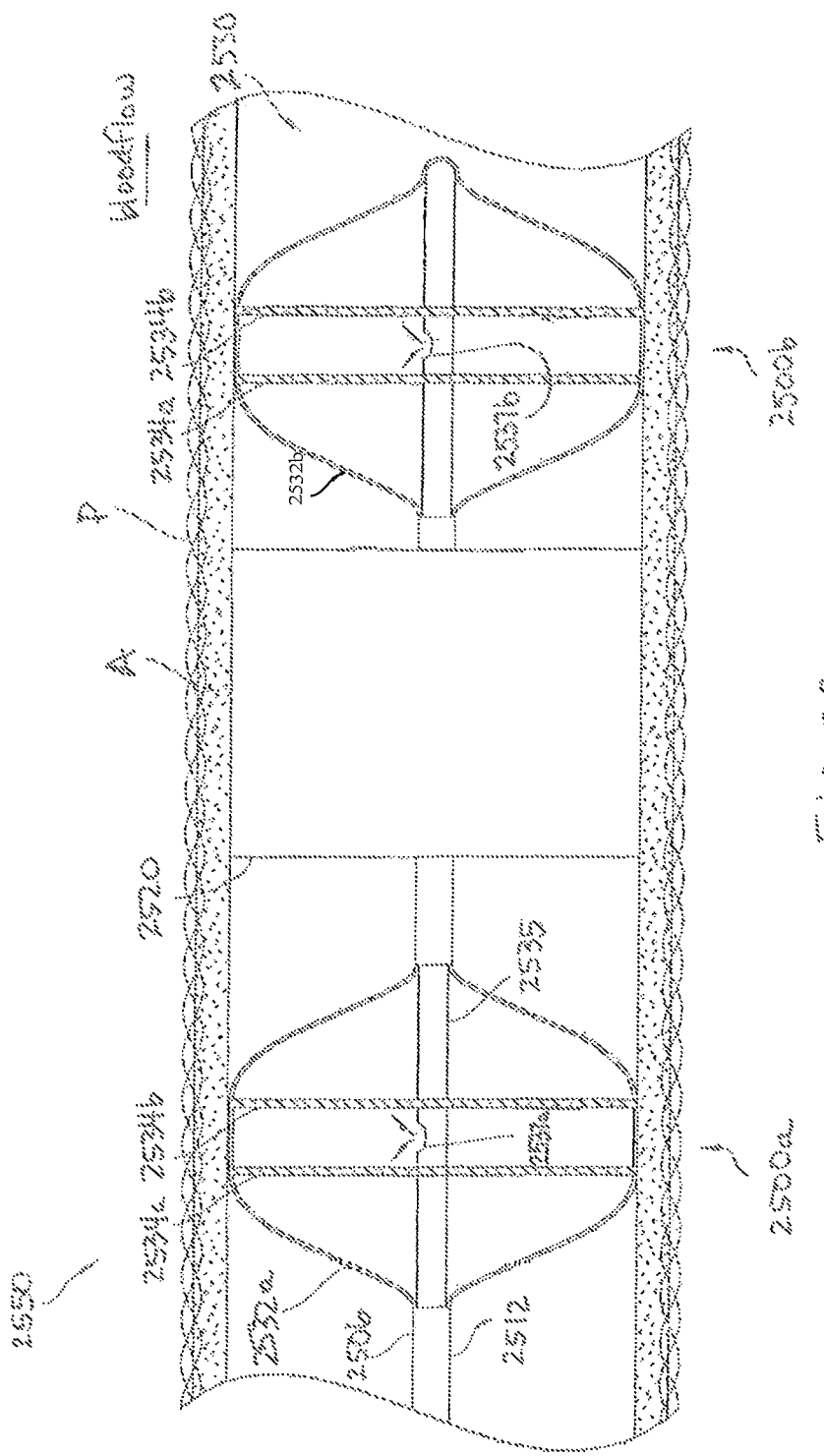

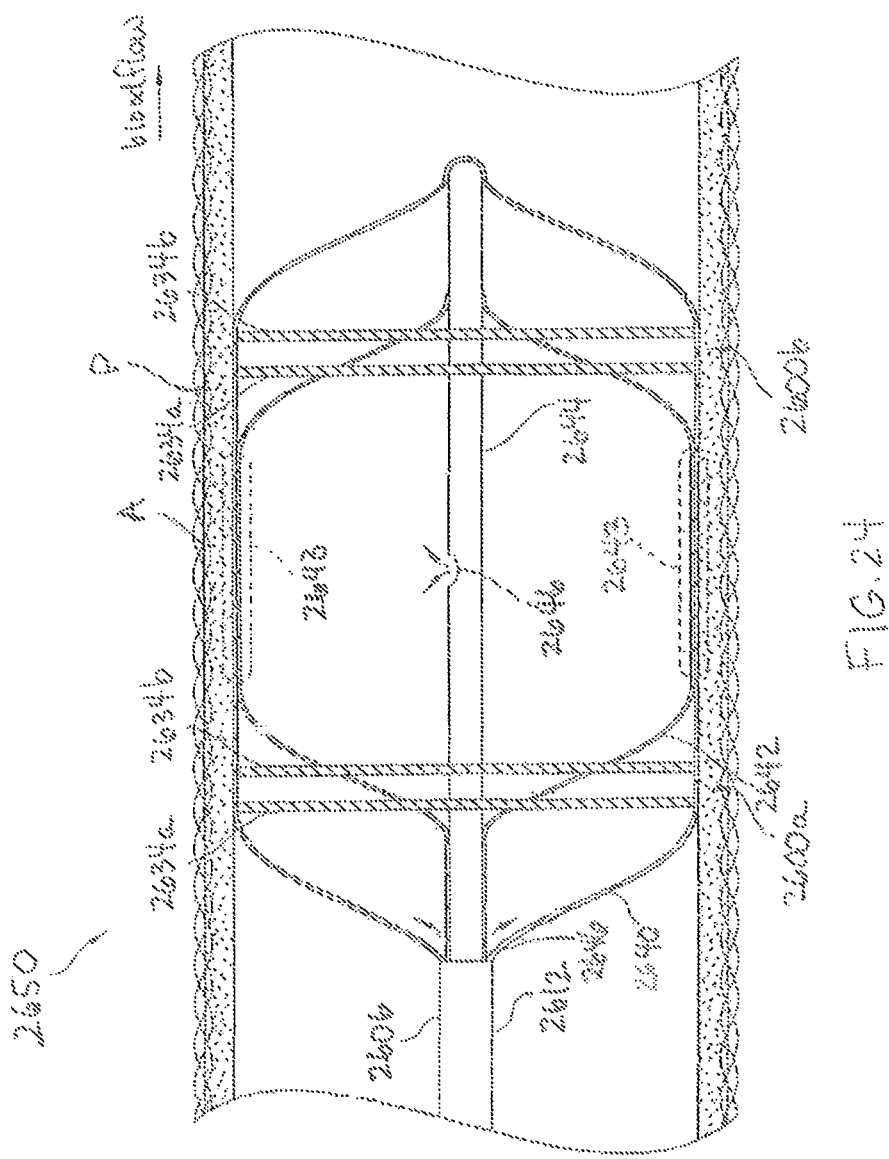

CATHETER APPARATUSES FOR MODULATION OF NERVES IN COMMUNICATION WITH PULMONARY SYSTEM AND ASSOCIATED SYSTEMS AND METHODS

CROSS-REFERENCE TO RELATED APPLICATION(S)

This application claims the benefit of U.S. Provisional Application No. 62/080,189, filed Nov. 14, 2014, U.S. Provisional Application No. 62/080,248, filed Nov. 14, 2014, and U.S. Provisional Application No. 62/082,635, filed Nov. 21, 2014, all of which are incorporated herein by reference in their entireties. Further, components and features of embodiments disclosed in the applications incorporated by reference may be combined with various components and features disclosed and claimed in the present application.

TECHNICAL FIELD

The present technology relates generally to modulation of nerves that communicate with the pulmonary system (e.g., pulmonary neuromodulation or "PN") and associated systems and methods. In particular, several embodiments are directed to radio frequency ("RF") ablation catheter apparatuses for intravascular modulation of nerves that communicate with the pulmonary system and associated systems and methods.

BACKGROUND

Pulmonary hypertension is an increase in blood pressure in the pulmonary vasculature. When portions of the pulmonary vasculature are narrowed, blocked or destroyed, it becomes harder for blood to flow through the lungs. As a result, pressure within the lungs increases and makes it hard for the heart to push blood through the pulmonary arteries and into the lungs, thereby causing the pressure in the arteries to rise. Also, because the heart is working harder than normal, the right ventricle becomes strained and weak, which can lead to heart failure. While there are pharmacologic strategies to treat pulmonary hypertension, there is no curative therapy other than lung transplantation. Thus, there is a strong public-health need for alternative treatment strategies.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology.

FIG. 3A1 is an illustrative cross-sectional anatomical front view showing the advancement of the catheter shown in FIG. 1 along an intravascular path in accordance with an embodiment of the present technology.

FIG. 3A2 is an illustrative cross-sectional anatomical front view showing the advancement of the catheter shown in FIG. 1 along another intravascular path in accordance with an embodiment of the present technology.

FIG. 17C is a side view of the distal portion of the catheter shown in FIG. 17A in a low-profile state configured in accordance with an embodiment of the present technology.

FIG. 17D is a side view of the distal portion of the catheter shown in FIG. 17A in a deployed state configured in accordance with an embodiment of the present technology.

FIG. 23 is an enlarged partially schematic side view of a distal portion of a treatment device within a blood vessel in accordance with a further embodiment of the present technology.

FIG. 24 is an enlarged side view of a distal portion of a treatment device within a blood vessel in accordance with yet another embodiment of the present technology.

DETAILED DESCRIPTION

Figure 1:
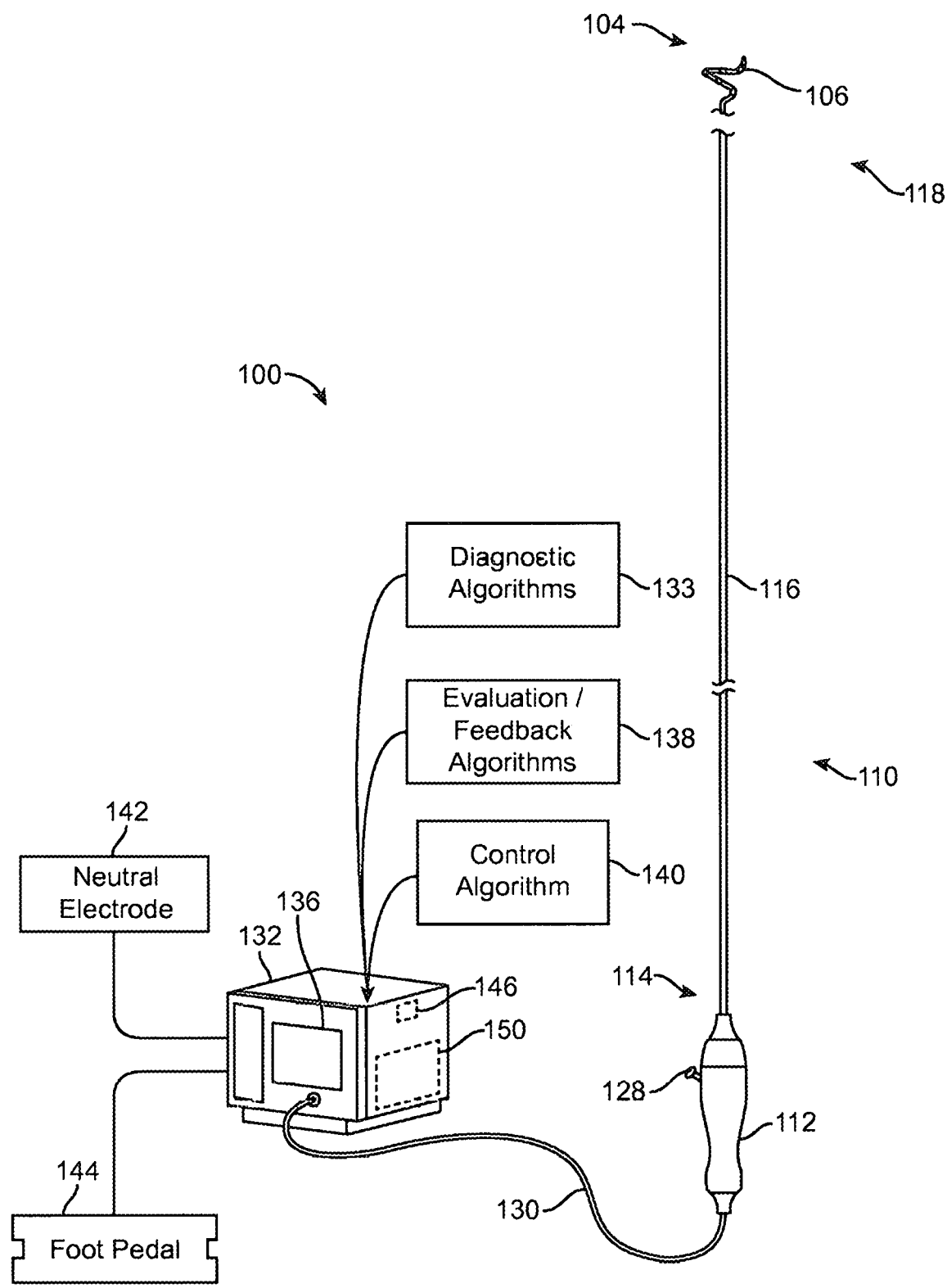
FIG. 1 is a partially-schematic view of a neuromodulation system configured in accordance with an embodiment of the present technology.

The present technology is directed to neuromodulation devices and associated systems and methods. Some embodiments of the present technology, for example, are directed to catheters and associated systems and methods for pulmonary neuromodulation ("PN"). Specific details of several embodiments of the technology are described below with reference to FIGS. 1-28. PN is the partial or complete incapacitation or otherwise effective disruption of nerves that communicate with the pulmonary system. For example, PN may inhibit, reduce, and/or block neural communication along neural fibers (i.e., efferent and/or afferent nerve fibers) innervating the pulmonary vessels. Such incapacitation can be long-term (e.g., permanent or for periods of months, years, or decades) or short-term (e.g., for periods of minutes, hours, days, or weeks). PN is expected to efficaciously treat pulmonary hypertension. Subjects with pulmonary hypertension generally have high blood pressure in the lung vasculature that may lead to heart failure and they may, for example, experience symptoms such as dyspnea (shortness of breath), syncope, fatigue, chest pain and/or edema, and/or other symptoms as well. PN using methods and/or devices described herein may provide a therapeutically beneficial reduction in one or more of these symptoms. Additionally, PN using the methods and/or devices of the present technology may modulate the release of circulating mediators of the nervous system (e.g., the sympathetic nervous system) and/or neuroendocrine system, thereby providing systemic modulation of such mediators and/or modulating the function of specific body organs other than the lungs. For example, the lungs produce significant quantities of catecholamines that affect heart rate, blood pressure, blood glucose levels, etc., and PN using the methods and/or devices of the present technology may increase or decrease the amount of catecholamines released from the lungs.

The catheters, systems and methods of the present technology may effect PN in and/or near one or more pulmonary vessels. As used herein, "pulmonary vessel(s)" include any blood vessel that is adjacent to and/or provides intravascular access proximate to neural pathways that communicate with the pulmonary system. For example, pulmonary vessels can include pulmonary veins and pulmonary arteries, such as the main pulmonary artery ("MPA"), the bifurcated portion of the pulmonary artery, the right pulmonary artery ("RPA"), the left pulmonary artery ("LPA"), segmental pulmonary arteries, and sub-segmental pulmonary arteries. Other non-limiting examples of pulmonary vessels include the right ventricular outflow tract, pulmonary arterioles, and/or any branch and/or extension of any of the pulmonary vessels described above. In some embodiments, the catheters, systems and methods of the present technology may effect PN in and/or near one or more pulmonary arteries (pulmonary arterial neuromodulation or "PAN"). For example, the present technology may effect neuromodulation at a distal portion of the MPA and/or in one or more branches (e.g., distal branches) of the MPA. In certain embodiments, the present technology may effect neuromodulation at or near the pulmonary valve (e.g., to affect nerves above and/or below the pulmonary valve).

As used herein, the terms "distal" and "proximal" define a position or direction with respect to the treating clinician or the clinician's control device (e.g., a handle assembly).

"Distal" or "distally" are a position distant from or in a direction away from the clinician or clinician's control device. "Proximal" and "proximally" are a position near or in a direction toward the clinician or clinician's control device.

It is typically advantageous to at least generally maintain the position of a neuromodulation unit relative to the surrounding anatomy during a neuromodulation treatment. For example, it can be advantageous to at least generally maintain stable contact between a therapeutic element of a neuromodulation unit and an inner wall of a body lumen (e.g., a blood vessel, a duct, an airway, or another naturally occurring lumen within the human body) during a neuromodulation treatment. In an alternative embodiment, it may be advantageous to maintain the position of the therapeutic element at the center of the vessel lumen or in some cases, offset from the center of the vessel lumen by a particular distance. This can enhance control and/or monitoring of the treatment, reduce trauma to the body lumen, and/or have other advantages. In some cases, at least generally maintaining the position of a neuromodulation unit relative to the target anatomy during a neuromodulation treatment can be challenging. For example, certain organs and/or body tissues may move in response to respiration, cardiac contraction and relaxation, peristaltic movement within blood vessels, and patient movement. Such movement of organs and other tissues in a patient's body can cause movement of a catheter shaft within a vessel or other disadvantageous relative movement between a neuromodulation unit connected to the shaft and the anatomy at a target site. Moreover, it may be challenging to maintain a device at the target site. For example, a pulmonary artery may generally be tapered, which can make it difficult to securely deploy certain device configurations there.

Another difficulty may exist with respect to initial positioning of a neuromodulation unit. When a neuromodulation unit is initially positioned at a treatment location within a pulmonary vessel or other body lumen (e.g., a renal vessel), the position of the neuromodulation unit may be suboptimal. For example, a catheter and/or a sheath carrying the catheter may be insufficiently flexible to match the curvature of anatomy near the treatment location (e.g., the curvature of a pulmonary artery between the MPA and the RPA and/or LPA). This may cause the catheter and/or the sheath to enter the body lumen out of alignment with a longitudinal dimension or other feature of the body lumen. When a neuromodulation unit of a misaligned catheter is initially moved into an expanded form, the neuromodulation unit may also be misaligned with the body lumen. When a neuromodulation unit is misaligned, one or more therapeutic elements of the neuromodulation unit may be out of contact or in poor contact with an inner wall of a body lumen, thereby resulting in suboptimal (or no) energy delivery to a target site. Even when the neuromodulation unit is sufficiently well aligned for treatment to begin, misalignment and migration may occur later and disturb the wall contact, potentially requiring the treatment to be aborted. Correcting misalignment of a neuromodulation unit can be challenging when the neuromodulation unit remains directly attached to an associated shaft trapped at a sharp turn.

I. SELECTED EMBODIMENTS OF CATHETERS AND RELATED DEVICES

FIG. 1 is partially-schematic diagram illustrating a pulmonary neuromodulation system 100 ("system 100") configured in accordance with an embodiment of the present technology. The system 100 includes an intravascular catheter 110 operably coupled to an energy source or energy generator 132 via a connector 130 (e.g., a cable). The catheter 110 can include an elongated shaft 116 having a proximal portion 114 and a distal portion 118. The catheter 110 also includes a handle assembly 112 at the proximal portion 114. The catheter 110 can further include a therapeutic assembly 104 carried by or affixed to the distal portion 118 of the elongated shaft 116, and the therapeutic assembly 104 can have one or more energy delivery elements 106 configured to modulate nerves at or near the treatment location. The elongated shaft 116 can be configured to intravascularly locate the therapeutic assembly 104 at a treatment location within a pulmonary artery, renal artery, or other blood vessel or, in a non-vascular delivery, through the esophagus, a bronchus, or another naturally occurring body lumen of a human patient.

The energy generator 132 can be configured to generate a selected form and/or magnitude of energy for delivery to the treatment site via the electrode(s) 106 of the therapeutic assembly 104. For example, the energy generator 132 can include an energy source (not shown) configured to generate RF energy (monopolar or bipolar), pulsed RF energy, microwave energy, optical energy, ultrasound energy (e.g., intravascularly delivered ultrasound, extracorporeal ultrasound, high-intensity focused ultrasound (HIFU)), direct heat energy, chemicals, radiation (e.g., infrared, visible, gamma), or another suitable type of energy. In some embodiments of devices, the devices may be configured for use with a source of cryotherapeutic energy, and/or for use with a source of one or more chemicals (e.g., to provide the cryotherapeutic energy and/or chemical(s) to a target site for PAN). In a particular embodiment, the energy generator 132 includes an RF generator operably coupled to one or more electrodes 106 of the therapeutic assembly 104.

In some embodiments, instead of or in addition to the energy delivery elements 106, the therapeutic assembly 104 can have ports or other substance delivery features to produce chemically based neuromodulation by delivering one or more chemicals. For example, suitable chemicals include guanethidine, one or more alcohols (e.g., ethanol), phenol, a neurotoxin (e.g., vincristine), or other suitable agents selected to alter, damage, or disrupt nerves. Additionally, in some embodiments the substance delivery features can be configured to deliver one or more pain management agents (e.g., an anesthetic agent) to the treatment site and/or one or more substances that enhance or otherwise control energy delivered by one or more electrodes 106 and/or effect nerve sensitivity or activation.

Furthermore, the energy generator 132 can be configured to control, monitor, supply, or otherwise support operation of the catheter 110. For example, a control mechanism, such as foot pedal 144, may be connected (e.g., pneumatically connected or electrically connected) to the energy generator 132 to allow an operator to initiate, terminate and/or adjust various operational characteristics of the energy generator, such as power delivery. In some embodiments, the energy generator 132 may be configured to provide delivery of a monopolar electric field via the electrode(s) 106. In such embodiments, one or more neutral or dispersive electrodes 142 may be electrically connected to the energy generator 132 and selectively positioned at a location within the patient's body (e.g., at, near, or within the esophagus, a bronchus, etc.) and/or attached to the exterior of the patient (not shown). The dispersive electrode 142 can be positioned to direct the applied electric field in a particular direction and/or towards or away from a particular anatomical location. Also, it can be advantageous to position the dispersive electrode such that it does not interfere with the line of sight of the imaging device.

In some embodiments, the system 100 includes a remote control device (not shown) that can be configured to be sterilized to facilitate its use within a sterile field. The remote control device can be configured to control operation of the therapeutic assembly 104, the energy generator 132, and/or other suitable components of the system 100. For example, the remote control device can be configured to allow for selective activation of the therapeutic assembly 104. In other embodiments, the remote control device may be omitted and its functionality may be incorporated into the handle 112 or energy generator 132.

As shown in FIG. 1, the energy generator 132 can further include an indicator or display screen 136. The energy generator 132 can include other indicators, including one or more LEDs, a device configured to produce an audible indication, and/or other suitable communicative devices. In the embodiment shown in FIG. 1, the display 136 includes a user interface configured to receive information or instructions from a user and/or provide feedback to the user. For example, the energy generator 132 can be configured to provide feedback to an operator before, during, and/or after a treatment procedure via the display 136. The feedback can be based on output from one or more sensors (not shown) associated with the therapeutic assembly 104 such as temperature sensor(s), impedance sensor(s), current sensor(s), voltage sensor(s), flow sensor(s), chemical sensor(s), ultrasound sensor(s), optical sensor(s), pressure sensor(s) and/or other sensing or monitoring devices. In some embodiments, the sensors can be used to monitor or detect the presence or location of target neural structures and/or assess the extent or efficacy of the treatment, as discussed in greater detail below with reference to FIGS. 21-28.

The system 100 can further include a controller 146 having, for example, memory (not shown) and processing circuitry (not shown). The memory and storage devices are computer-readable storage media that may be encoded with non-transitory, computer-executable instructions such as diagnostic algorithm(s) 133, control algorithm(s) 140, and/or evaluation/feedback algorithm(s) 138. The control algorithms 140 can be executed on a processor (not shown) of the system 100 to control energy delivery to the electrodes 106. In some embodiments, selection of one or more parameters of an automated control algorithm 140 for a particular patient may be guided by diagnostic algorithms 133 that measure and evaluate one or more operating parameters prior to energy delivery. The diagnostic algorithms 133 provide patient-specific feedback to the clinician prior to activating the electrodes 106 which can be used to select an appropriate control algorithm 140 and/or modify the control algorithm 140 to increase the likelihood of efficacious neuromodulation.

Although in the embodiment shown in FIG. 1 the controller 146 is incorporated into the energy generator 132, in other embodiments the controller 146 may be an entity distinct from the energy generator 132. For example, additionally or alternatively, the controller 146 can be a personal computer(s), server computer(s), handheld or laptop device(s), multiprocessor system(s), microprocessor-based system(s), programmable consumer electronic(s), digital camera(s), network PC(s), minicomputer(s), mainframe computer(s), and/or any suitable computing environment.

In some embodiments, the energy source 132 may include a pump 150 or other suitable pressure source (e.g., a syringe) operably coupled to an irrigation port (not shown) at the distal portion 118 of the catheter 110. In other embodiments, the pump 150 can be a standalone device separate from the energy source 132. Positive pressure generated by the pump 150 can be used, for example, to push a protective agent (e.g., saline) through the irrigation port to the treatment site. In yet other embodiments, the catheter 110 can include an adapter (not shown) (e.g., a luer lock) configured to be operably coupled to a syringe (not shown) and the syringe can be used to apply pressure to the shaft 116. In a particular embodiment, the pump 150 or other suitable pressure source can be configured to push one or more of the aforementioned deliverable agents through the irrigation port to the treatment site (e.g., chemically-based neuromodulation agents, pain management agents, energy-enhancement/control agents, agents that affect nerve sensitivity or activation, etc.).

Figure 2A:
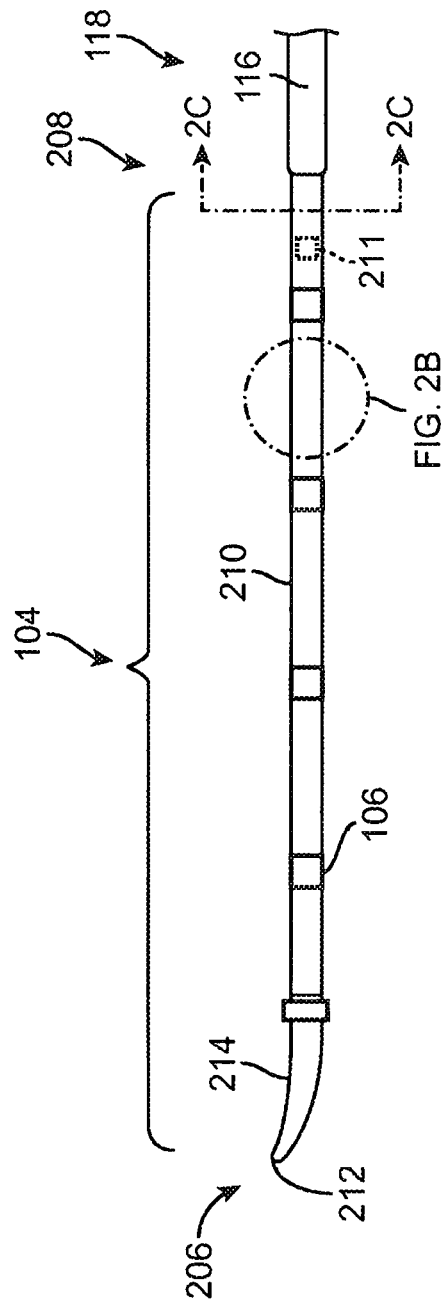
FIG. 2A is an enlarged side view illustrating a therapeutic assembly of the catheter of FIG. 1 in a low-profile configuration in accordance with an embodiment of the present technology.

FIG. 2A is a side view of the therapeutic assembly 104 in a low-profile or delivery state in accordance with an embodiment of the present technology. A proximal region 208 of the therapeutic assembly 104 can be carried by or affixed to the distal portion 118 of the elongated shaft 116. For example, all or a portion (e.g., a proximal portion) of the therapeutic assembly 104 can be an integral extension of the shaft 116. A distal region 206 of the therapeutic assembly 104 may terminate distally with, for example, an atraumatic, flexible curved tip 214 having an opening 212 at its distal end. In some embodiments, the distal region 206 of the therapeutic assembly 104 may also be configured to engage another element of the system 100 or catheter 110.

Figure 2C:
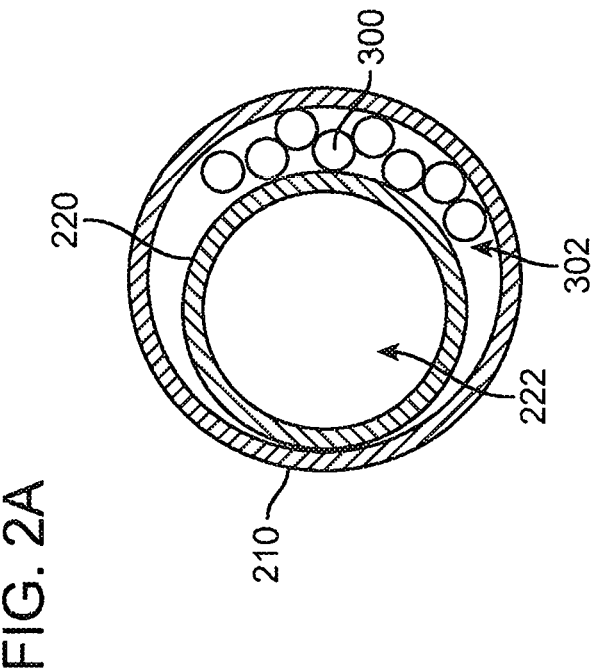
FIG. 2C is a cross-sectional end view taken along line 2C-2C in FIG. 2A.
Figure 2B:
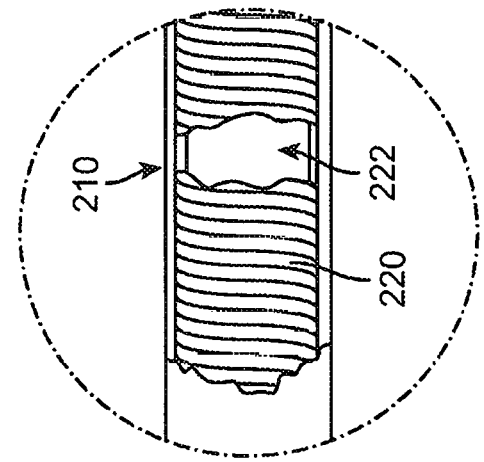
FIG. 2B is a further enlarged cut-away view of a portion of the therapeutic assembly FIG. 2A in accordance with an embodiment of the present technology.

FIG. 2B is an enlarged view of a portion of the therapeutic assembly 104 of FIG. 2A, and FIG. 2C is a cross-sectional end view taken along line 2C-2C in FIG. 2A. Referring to FIGS. 2A-2C together, the therapeutic assembly 104 can include the one or more energy delivery elements 106 carried by a helical/spiral-shaped support structure 210. The helical/spiral support structure 210 can have one or more turns (e.g., two turns, etc.). Examples of suitable energy delivery elements include RF electrodes, ultrasound transducers, cryotherapeutic cooling assemblies, and/or other elements that deliver other types of energy. The energy delivery elements 106, for example, can be separate band electrodes axially spaced apart along the support structure 210 (e.g., adhesively bonded, welded (e.g., laser bonded) or bonded by mechanical interference to the support structure 210 at different positions along the length of the support structure 210). In other embodiments, the therapeutic assembly 104 may have a single energy delivery element 106 at or near the distal portion 118 of the shaft 116.

In embodiments where the support structure includes more than one energy delivery element, the support structure can include, for example, between 1 and 12 energy delivery elements (e.g., 1 element, 4 elements, 10 elements, 12 elements, etc.). In some embodiments, the energy delivery elements can be spaced apart along the support structure every 1 mm to 50 mm, such as every 2 mm to every 15 mm (e.g., every 10 mm, etc.). In the deployed configuration, the support structure and/or therapeutic assembly can have an outer diameter between about 12 mm and about 20 mm (e.g., between about 15 mm and about 18 mm). Additionally, the support structure and energy delivery elements can be configured for delivery within a guide catheter between 5 Fr and 9 Fr. In other examples, other suitable guide catheters may be used, and outer dimensions and/or arrangements of the catheter 110 can vary accordingly.

In some embodiments, the energy delivery elements 106 are formed from gold, platinum, alloys of platinum and iridium, other metals, and/or other suitable electrically conductive materials. The number, arrangement, shape (e.g., spiral and/or coil electrodes) and/or composition of the energy delivery elements 106 may vary. The individual energy delivery elements 106 can be electrically connected to the energy generator 132 by a conductor or bifilar wire 300 (FIG. 2C) extending through a lumen 302 of the shaft 116 and/or support structure 210. For example, the individual energy delivery elements 106 may be welded or otherwise electrically coupled to corresponding energy supply wires 300, and the wires 300 can extend through the elongated shaft 116 for the entire length of the shaft 116 such that proximal ends of the wires 300 are coupled to the handle 112 and/or to the energy generator 132.

In a particular embodiment, the catheter 110 can include an electrical element 211 (FIG. 2A) positioned along the shaft 116 between the energy delivery elements 106 and the proximal portion of the shaft 116. The electrical element 211 can be electrically coupled to the energy delivery elements 106 via their respective bifilar wires 300. The catheter 110 can include an additional bifilar wire (not shown) that electrically couples the electrical element 211 and the energy generator 132. The additional bifilar wire, for example, can extend proximally from the electrical element 211 through the shaft 116 such that the proximal end of the wire is coupled to the handle 112 and/or to the generator 132. In some embodiments, the electrical element 211 can include an analog-to-digital converter configured to receive an analog signal from the energy generator 132 and transmit a digital signal to the energy delivery elements 106. Use of an analog-to-digital converter can be advantageous because, unlike analog signals, digital signals are not susceptible to interference. In these and other embodiments, the electrical element 211 can include a multiplexer configured to independently transmit signals to and/or from one or more of the energy delivery elements.

As shown in the enlarged cut-away view of FIG. 2B, the support structure 210 can be a tube (e.g., a flexible tube) and the therapeutic assembly 104 can include a pre-shaped control member 220 positioned within the tube. Upon deployment, the control member 220 can form at least a portion of the therapeutic assembly 104 into a deployed state (FIG. 3C-3E). For example, the control member 220 can have a pre-set configuration that gives at least a portion of the therapeutic assembly 104 a helical/spiral configuration in the deployed state (FIG. 3C-3E). In some embodiments, the control member 220 includes a tubular structure comprising a Nitinol multifilar stranded wire with a lumen 222 therethrough and sold under the trademark HELICAL HOLLOW STRAND® (HHS), and commercially available from Fort Wayne Metals of Fort Wayne, Ind. The lumen 222 can define a passageway for receiving a guide wire (not shown) that extends proximally from the opening 212 (FIG. 2A) at the tip 214 of the therapeutic assembly 104. In other embodiments, the control member 220 may be composed of different materials and/or have a different configuration. For example, the control member 220 may be formed from nickel-titanium (Nitinol), shape memory polymers, electroactive polymers or other suitable shape memory materials that are pre-formed or pre-shaped into the desired deployed state. Alternatively, the control member 220 may be formed from multiple materials such as a composite of one or more polymers and metals.

As shown in FIG. 2C, the support structure 210 can be configured to fit tightly against the control member 220 and/or wires 300 to reduce space between an inner portion of the support structure 210 and the components positioned therein. For example, the control member 220 and the inner wall of the support structure 210 can be in intimate contact such that there is little or no space between the control member 220 and the support structure 210. Such an arrangement can help to reduce or prevent the formation of wrinkles in the therapeutic assembly 104 during deployment. The support structure 210 may be composed of one or more polymer materials such as polyamide, polyimide, polyether block amide copolymer sold under the trademark PEBAX®, polyethylene terephthalate ("PET"), polypropylene, aliphatic, polycarbonate-based thermoplastic polyurethane sold under the trademark CARBOTHANE®, ELASTHANE® TPU, a polyether ether ketone ("PEEK") polymer, or another suitable material that provides sufficient flexibility to the support structure 210.

In some embodiments, when the therapeutic assembly 104 and/or support structure 210 is in deployed configuration, the therapeutic assembly 104 and/or support structure 210 preferably define a minimum width of greater than or equal to approximately 0.040". Additionally, the support structure 210 and energy delivery elements 106 are configured for delivery within a guide catheter no smaller than a 5 French guide catheter. In other examples, other suitable guide catheters may be used, and outer dimensions and/or arrangements of the catheter 110 can vary accordingly.

Referring to FIG. 2A, the curved tip 214 can be configured to provide an exit (e.g., via the opening 212) for a guide wire that directs the guide wire away from a wall of a vessel or lumen at or near a treatment location. As a result, the curved tip 214 can facilitate alignment of the therapeutic assembly 104 in the vessel or lumen as it expands from the delivery state shown in FIG. 2A. Furthermore, the curved tip 214 can reduce the risk of injuring a wall of the vessel or lumen when a distal end of a guide wire is advanced from the opening 212. The curvature of the tip 214 can be varied depending upon the particular sizing/configuration of the therapeutic assembly 104 and/or anatomy at a treatment location. In some embodiments, the tip 214 may also comprise a radiopaque marker (not shown) and/or one or more sensors (not shown) positioned anywhere along the length of the tip 214. For example, in some embodiments, the tip 214 can include one or more layers of material (e.g., the same or different materials) and the radiopaque marker can be sandwiched between two or more layers. Alternatively, the radiopaque marker can be soldered, glued, laminated, or mechanically locked to the exterior surface of the tip 214. In other embodiments, the entire tip 214 or a portion of the tip 214 can be made of or include a radiopaque material and/or the tip 214 can be coated with a radiopaque material. The tip 214 can be affixed to the distal end of the support structure 210 via adhesive, crimping, over-molding, or other suitable techniques.

The flexible curved tip 214 can be made from a polymer material (e.g., polyether block amide copolymer sold under the trademark PEBAX®), a thermoplastic polyether urethane material (sold under the trademarks ELASTHANE® or PELLETHANE®), or other suitable materials having the desired properties, including a selected durometer. As noted above, the tip 214 is configured to provide an opening for the guide wire, and it is desirable that the tip itself maintain a desired shape/configuration during operation. Accordingly, in some embodiments, one or more additional materials may be added to the tip material to help improve tip shape retention. In one particular embodiment, for example, about 5 to 30 weight percent of siloxane can be blended with the tip material (e.g., the thermoplastic polyether urethane material), and electron beam or gamma irradiation may be used to induce cross-linking of the materials. In other embodiments, the tip 214 may be formed from different material(s) and/or have a different arrangement.

II. SELECTED DELIVERY EMBODIMENTS

Figure 3B:
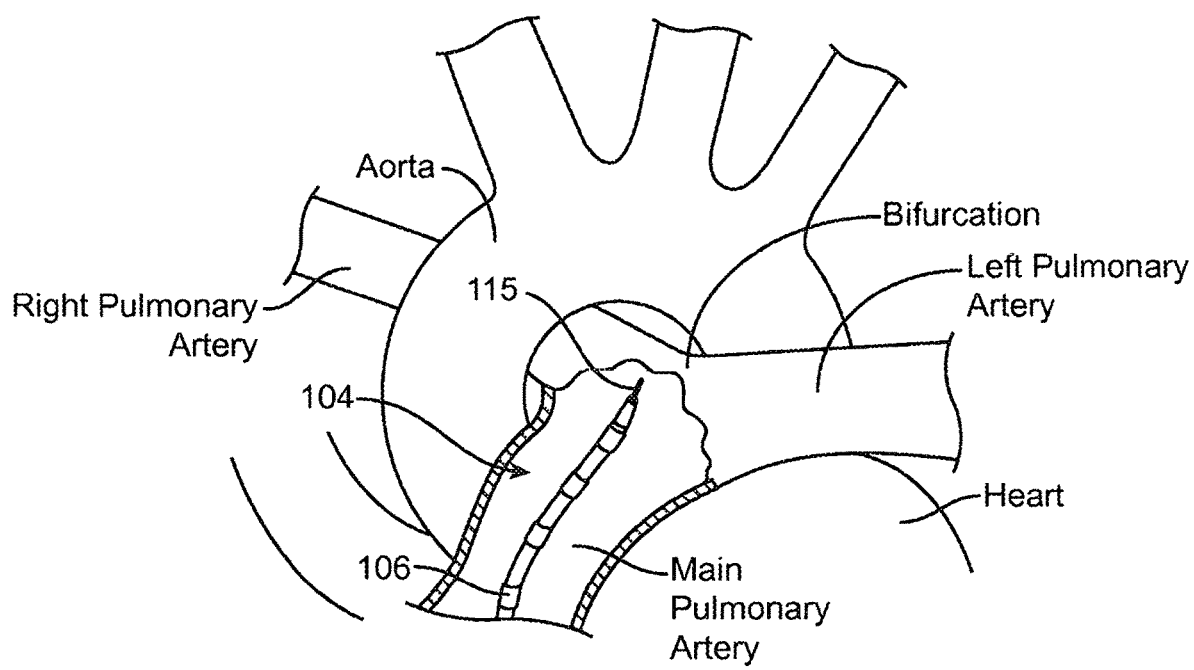
FIG. 3B is a side view of the therapeutic assembly shown in FIG. 2A within the main pulmonary artery in a low-profile configuration in accordance with an embodiment of the present technology.
Figure 3C:
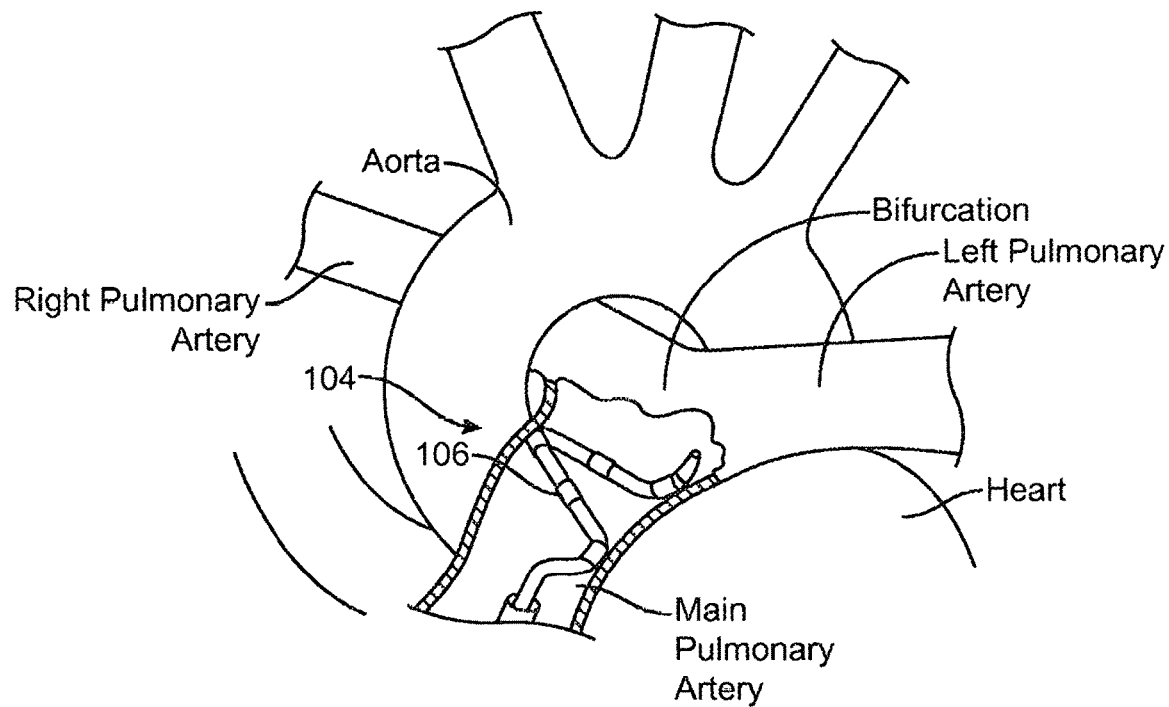
FIG. 3C is a side view of the therapeutic assembly shown in FIG. 2A within the main pulmonary artery in a deployed configuration in accordance with an embodiment of the present technology.
Figure 3D:
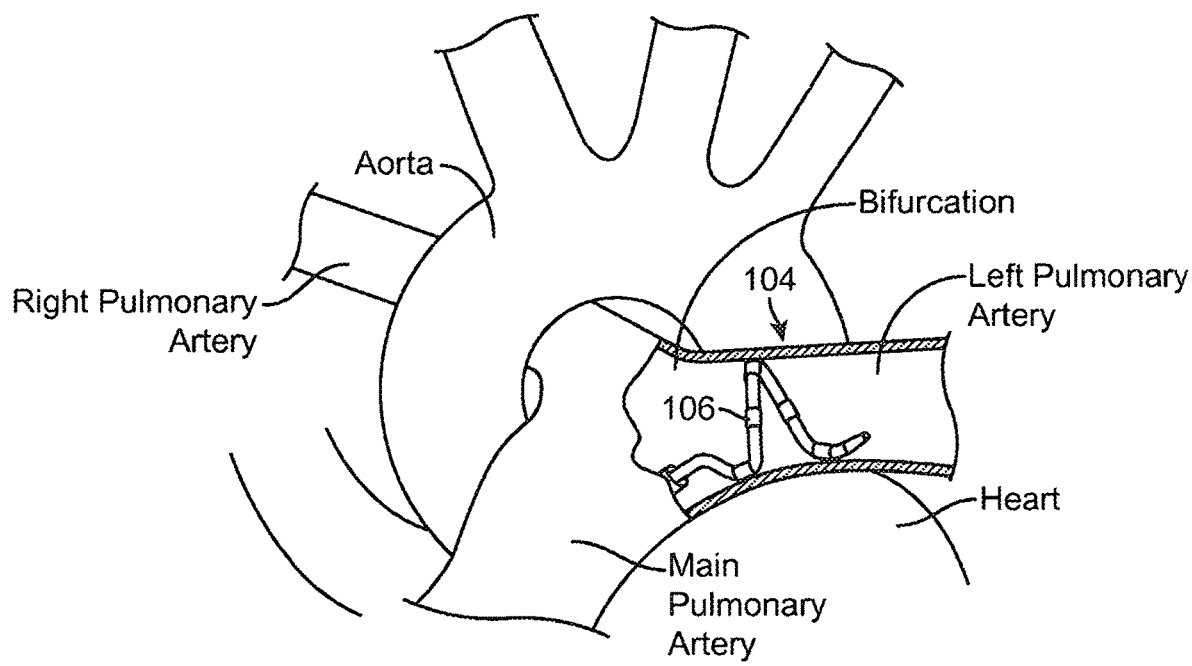
FIG. 3D is a side view of the therapeutic assembly shown in FIG. 2A within the left pulmonary artery in a deployed configuration in accordance with an embodiment of the present technology.
Figure 3E:
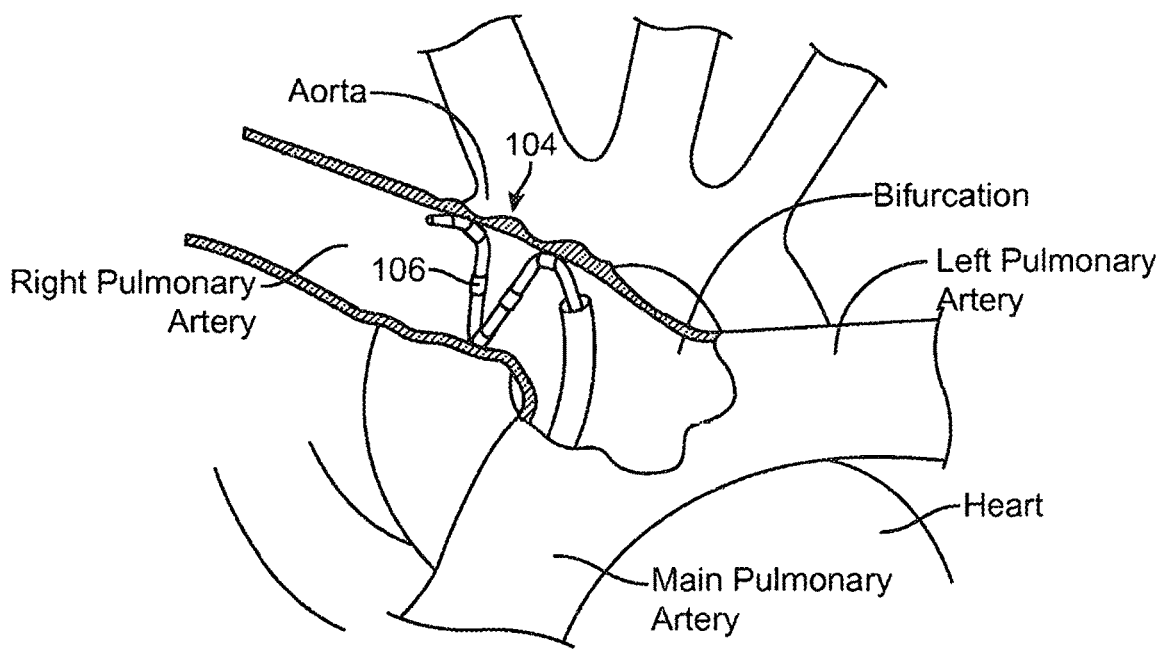
FIG. 3E is a side view of the therapeutic assembly shown in FIG. 2A within the right pulmonary artery in a deployed configuration in accordance with an embodiment of the present technology.

Referring to FIGS. 3A1 and 3A2, intravascular delivery of the therapeutic assembly 104 can include percutaneously inserting a guide wire 115 within the vasculature at an access site and progressing the guidewire to the MPA. Suitable access sites include, for example, the femoral (FIG. 3A1), brachial, radial, axillary, jugular (FIG. 3A2) or subclavian arteries or veins. The lumen 222 (FIGS. 2B and 2C) of the shaft 116 and/or therapeutic assembly 104 can be configured to receive a guide wire 115 in an over-the-wire or rapid exchange configuration. As shown in FIG. 3B, the shaft and the therapeutic assembly (in the delivery state) can then be advanced along the guide wire 115 until at least a portion of the therapeutic assembly 104 reaches the treatment location. As illustrated in FIG. 3A, a section of the proximal portion 114 of the shaft 116 can be extracorporeally positioned and manipulated by the operator (e.g., via the actuator 128 shown in FIG. 1) to advance the shaft through the sometimes tortuous intravascular path and remotely manipulate the distal portion of the shaft.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the therapeutic assembly 104. For example, a fluoroscopy system (e.g., including a flat-panel detector, x-ray, or c-arm) can be rotated to accurately visualize and identify the target treatment site. In other embodiments, the treatment site can be located using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the catheter 110. Further, in some embodiments, image guidance components (e.g., IVUS, OCT) may be integrated with the catheter 110 and/or run in parallel with the catheter 110 to provide image guidance during positioning of the therapeutic assembly 104. For example, image guidance components (e.g., IVUS or OCT) can be coupled to a distal portion of the catheter 110 to provide three-dimensional images of the vasculature proximate the target site to facilitate positioning or deploying the therapeutic assembly 104 within the target blood vessel.

Once the therapeutic assembly 104 is positioned at a treatment location, such as within a pulmonary artery, the guide wire 115 can be at least partially removed (e.g., withdrawn) from or introduced (e.g., inserted) into the therapeutic assembly 104 to transform or otherwise move the therapeutic assembly 104 to a deployed configuration. FIG. 3C is a side view of the therapeutic assembly 104 shown in FIG. 2A within the main pulmonary artery in a deployed configuration, FIG. 3D is a side view of the therapeutic assembly 104 within the left pulmonary artery, and FIG. 3E is a side view of the therapeutic assembly 104 within the right pulmonary artery in accordance with an embodiment of the present technology. As shown in FIGS. 3B-3D, in the deployed state, at least a portion of the therapeutic assembly 104 can be configured to contact an inner wall of a pulmonary artery and to cause a fully-circumferential lesion without the need for repositioning. For example, the therapeutic assembly 104 can be configured to form a continuous or discontinuous lesion that is fully-circumferential within a single plane perpendicular to the longitudinal axis of the vessel (see, for example, FIG. 22A). In other embodiments, the therapeutic assembly 104 can be configured to form a continuous or discontinuous lesion that wraps around the circumference of the vessel (one or more times) along a particular length of the vessel (e.g., generally non-circumferential at longitudinal segments of the treatment location). In several of such embodiments, the lesion can have a helical/spiral configuration. This can facilitate precise and efficient treatment with a low possibility of vessel stenosis. In other embodiments, the therapeutic assembly 104 can be configured to form a partially-circumferential lesion or a fully-circumferential lesion at a single longitudinal segment of the treatment location. In some embodiments, the therapeutic assembly 104 can be configured to cause therapeutically-effective neuromodulation (e.g., using ultrasound energy) without contacting a vessel wall.

As shown in FIGS. 3C-3E, in the deployed state, the therapeutic assembly 104 defines a substantially helical/spiral structure in contact with the pulmonary artery wall along a helical/spiral path. One advantage of this arrangement is that pressure from the helical/spiral structure can be applied to a large range of radial directions without applying pressure to a circumference of the pulmonary vessel. Thus, the spiral/helically-shaped therapeutic assembly 104 is expected to provide stable contact between the energy delivery elements 106 and the pulmonary vessel wall when the wall moves in any direction. Furthermore, pressure applied to the pulmonary vessel wall along a helical/spiral path is less likely to stretch or distend a circumference of a vessel that could thereby cause injury to the vessel tissue. Still another feature of the expanded helical/spiral structure is that it may contact the pulmonary vessel wall in a large range of radial directions and maintain a sufficiently open lumen in the pulmonary vessel allowing blood to flow through the helix/spiral during therapy. In other embodiments, the therapeutic assembly 104 can define a circular structure (see, for example, FIG. 22A) in contact with the pulmonary artery wall along a circular or fully-circumferential path.

In some procedures it may be necessary to adjust the positioning of the therapeutic assembly 104 one or more times. For example, the therapeutic assembly 104 can be used to modulate nerves proximate the wall of the main pulmonary artery, the left pulmonary artery, and/or the right pulmonary artery and/or any branch or extension. Additionally, in some embodiments the therapeutic assembly 104 may be repositioned within the same pulmonary vessel multiple times within the same procedure. After repositioning, the clinician may then re-activate the therapeutic assembly 104 to modulate the nerves.

Often times it may be advantageous to modulate nerves and/or electrical signals at two or more locations within the body. As an example, one device may be used to modulate renal nerves, while another device is used to modulate electrical signals in the heart. As another example, pulmonary neuromodulation may be effected in one location in the body, while modulation of electrical signals may be effected in the heart (e.g., simultaneously or sequentially). In some embodiments, modulation may result in denervation of one or more of the treated locations. In certain embodiments, cardiac tissue (e.g., the right atrium of the heart of a patient) may be ablated to modulate electrical signals within the heart (e.g., preventing abnormal electrical signals from occurring), and one or more renal arteries of the patient may also be ablated to modulate nerves proximate the renal artery or renal arteries (e.g., nerves extending along the outside of the renal artery or renal arteries). The modulation of nerves and/or electrical signals may result in a reduction in clinical symptoms of pulmonary hypertension. Two or more different locations in the body may be modulated in the same procedure (at the same time or at different times) and/or in different procedures (e.g., one taking place immediately after the other has been completed, or days, weeks or months after the other has been completed). Additionally, different types of denervation may be employed in one patient.

In some methods, mechanical devices may be used, such as a device (e.g., an implant) that modulates blood flow, creates an anastomosis, and/or affects baroreceptors. Such devices may be used alone (e.g., multiple of the same type of device in different locations), in combination with each other, and/or in combination with devices that modulate nerves and/or electrical signals.

Although the embodiments shown in FIGS. 3C-3E show a deployed therapeutic assembly 104 in a spiral or helically-shaped configuration, in other embodiments, the therapeutic assembly 104 and/or other portions of the therapeutic assembly 104 can have other suitable shapes, sizes, and/or configurations (e.g., bent, deflected, zig-zag, Malecot, etc.). Examples of other suitable therapeutic assembly configurations, deployment configurations and/or deployment mechanisms can be found in: U.S. application Ser. No. 12/910,631, filed Oct. 22, 2010; U.S. application Ser. No. 13/281,361, filed Oct. 25, 2011; U.S. Provisional Application No. 61/646,218, filed May 5, 2012; U.S. Provisional Application No. 61/895,297, filed Oct. 24, 2013; PCT Application No. PCT/US11/57754, filed Oct. 25, 2011; U.S. Pat. No. 8,888,773, filed Mar. 11, 2013; and U.S. patent application Ser. No. 13/670,452, filed Nov. 6, 2012. All of the foregoing references are incorporated herein by reference in their entireties. Non-limiting examples of devices and systems include the Symplicity Flex™, the Symplicity Spyral™ multielectrode RF ablation catheter, and the Arctic Front Advance™ cardiac cryoablation system.

Figure 4:
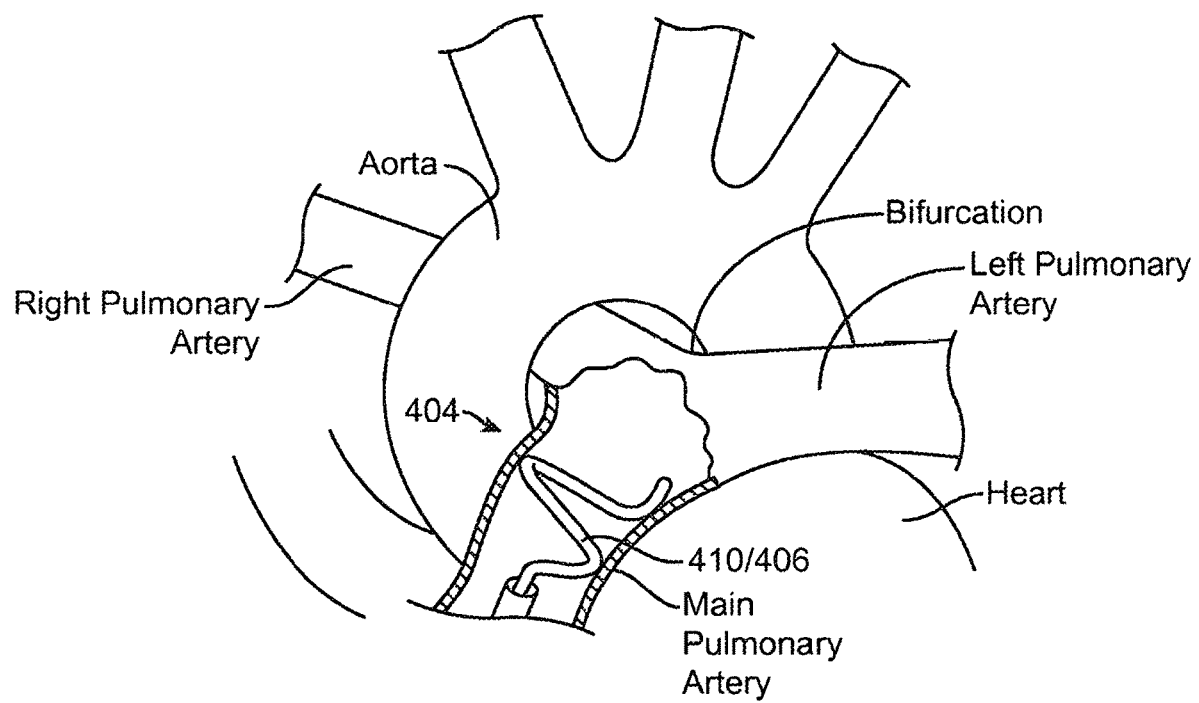
FIG. 4 is a side view of a therapeutic assembly having a single wire electrode configured in accordance with an embodiment of the present technology.

FIG. 4 shows another embodiment of a therapeutic assembly 404 comprising a support structure 410 defined by a single wire electrode 406. For example, the support structure 410 can be a unipolar single metal wire (e.g., Nitinol) that is pre-formed into a helical/spiral shape. The single wire electrode 406 can have a continuous electrically conductive surface along all or a significant part of its length such that it forms a continuous helical lesion around a complete or nearly complete turn of the spiral/helix. In some embodiments, the wire electrode 406 can have a diameter of between about 0.002 inches and about 0.010 inches (e.g., about 0.008 inches). In other embodiments, the therapeutic assembly 404 can include a "ground" electrode that is electrically insulated from the spiral at a more proximal portion of the spiral/helix (e.g., a bipolar configuration). The spiral/helix can have a constant diameter, or in other embodiments the spiral/helix can have a varying diameter. For example, spiral/helix can have a diameter that tapers in a distal direction or a proximal direction. In other embodiments, the single wire electrode has discrete dielectric coating segments that are spaced apart from each other to define discrete energy delivery elements between the dielectric coating segments. The single wire electrode can be made from a shape memory metal or other suitable material. Additionally, the control algorithm 140 (FIG. 1) can be adjusted to account for the increased surface area contact of the single wire electrode 406 such that sufficient ablation depths can be achieved without charring or overheating the inner wall of the vessel.

In some embodiments, the single wire electrode 406 can be delivered with the guide catheter (not shown) or an additional sheath (not shown) for precise positioning and deployment. The guide catheter (not shown) can be advanced and/or manipulated until positioned at a desired location proximate the treatment site. The therapeutic assembly 404 can then be inserted through the guide catheter. In some embodiments, the therapeutic assembly 404 expands into a helical/spiral shape immediately once exiting a distal end of the guide catheter. In other embodiments, the single wire electrode 406 can be tubular and transforms into a helical/spiral shape when a guide wire (placed therethrough) is removed in a proximal direction. In yet other embodiments, the therapeutic assembly 404 expands into a circular shape immediately once exiting a distal end of the guide catheter.

A. Rotation Devices and Methods

Figure 5A:
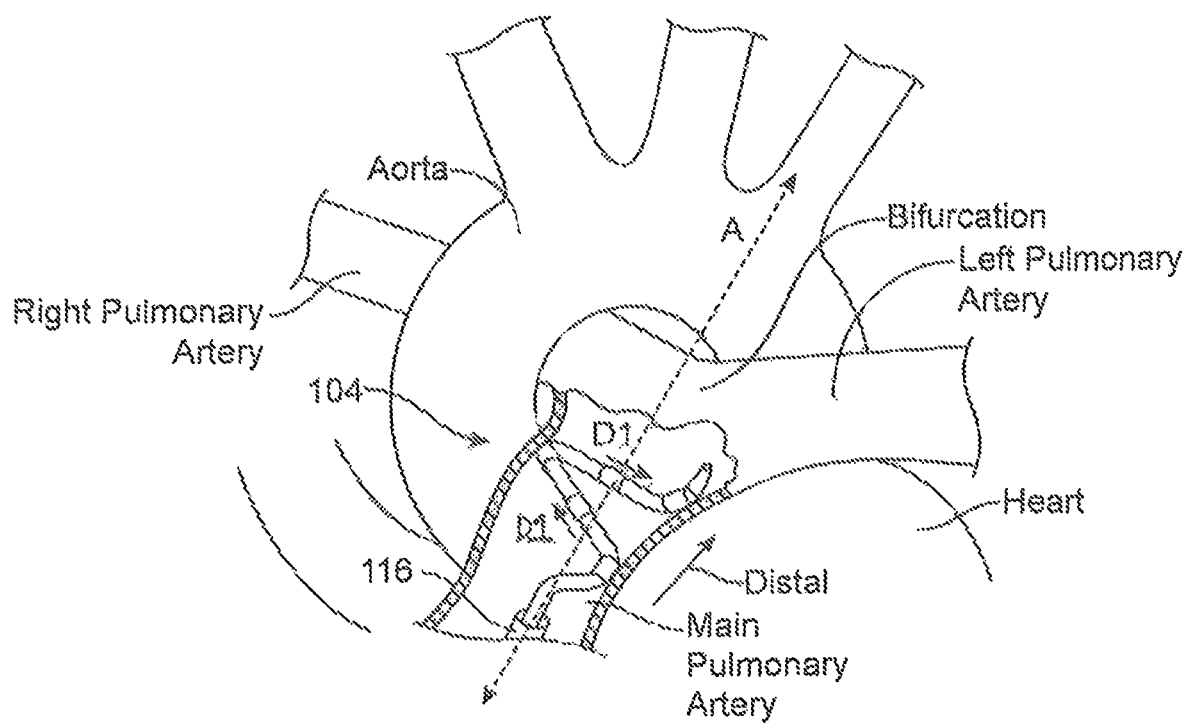
FIGS. 5A-5B are schematic representations illustrating rotational directions of the therapeutic assembly as noted by opposite arrow directions.
Figure 5B:
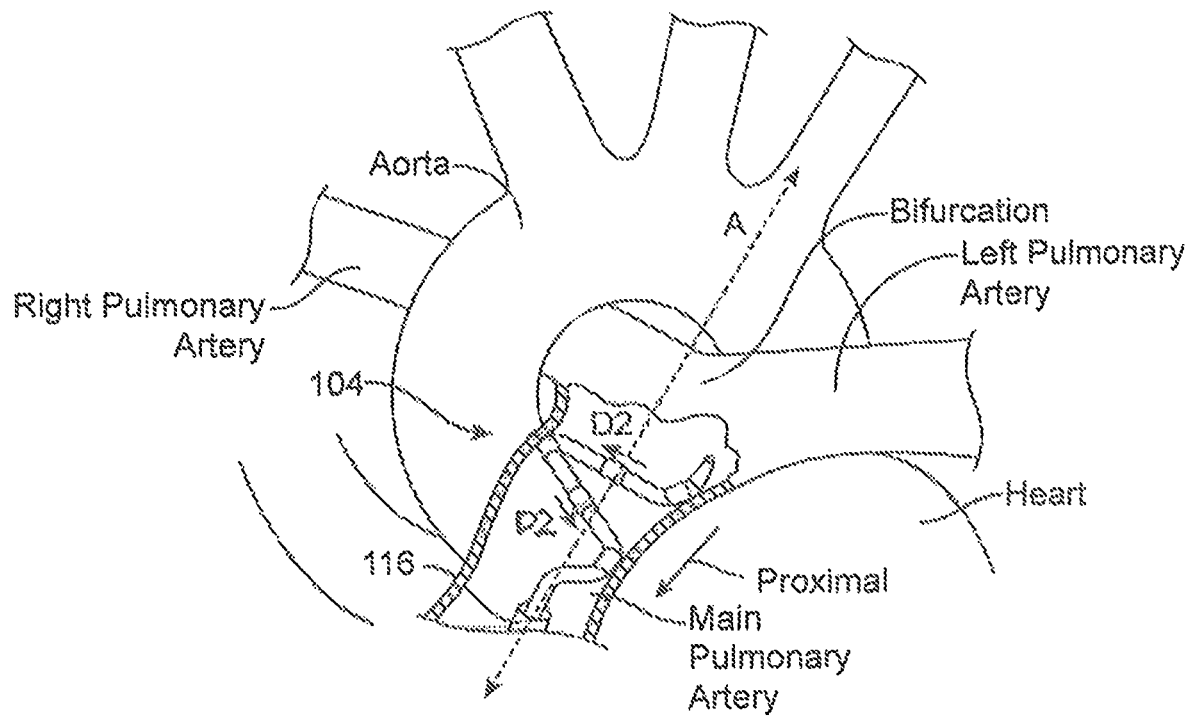

As shown in FIGS. 5A and 5B, the therapeutic assembly 104 can be configured to rotate about a longitudinal axis A when advanced distally from the shaft 116 or retracted proximally from the shaft 116. For example, when the therapeutic assembly 104 is advanced distally, the spiral/helical structure can be rotated in a first direction, as shown by arrows D1 in FIG. 5A. Likewise, when the therapeutic assembly 104 is retracted proximally, the spiral/helical structure can be rotated in a second direction, as shown by arrows D2 in FIG. 5B. Such a rotational feature can be particularly advantageous in the pulmonary vessels, since, at least at the MPA and proximal portions of the LPA and RPA, the pulmonary vessels have relatively large diameters that can require a large number of lesions to provide fully-circumferential coverage and/or effective treatment. To compensate for this, effective treatment in the pulmonary vessels can often times require multiple rotations of the therapeutic assembly 104 to reposition the therapeutic assembly 104 and achieve such a fully-circumferential lesion. Additionally, rotation of the therapeutic assembly 104 can aid in maneuvering the therapeutic assembly 104 through a turn in a vessel, such as when accessing a branch or segment of a larger vessel (e.g., accessing the LPA and RPA from the MPA).

Figure 6:
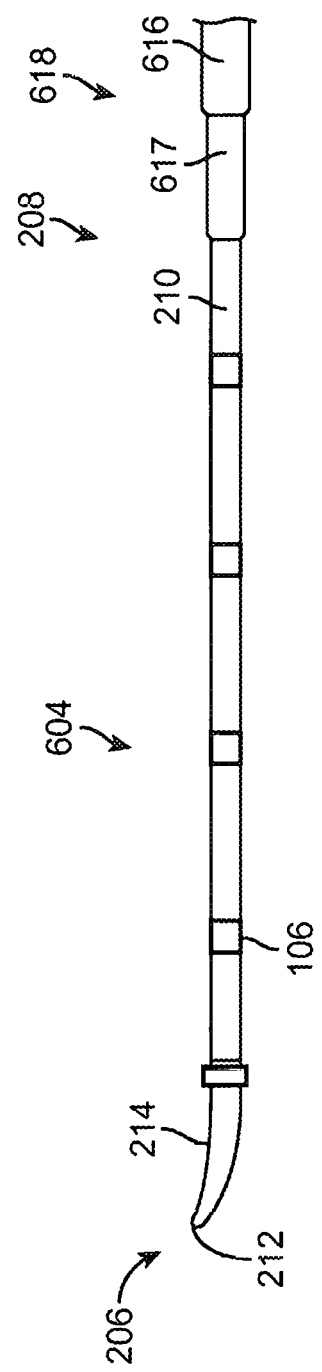
FIG. 6 is a schematic side view of a catheter having an inner sheath configured in accordance with an embodiment of the present technology.

FIG. 6 is a side view of another embodiment of a catheter 618 configured in accordance with the present technology. The catheter 618 can include a therapeutic assembly 604 generally similar to the previously described therapeutic assembly 104 (referenced herein with respect to FIGS. 1-4). As shown in FIG. 6, the catheter 618 includes an inner sheath 617 slidably positioned within a guide catheter 616 between the guide catheter 616 and the therapeutic assembly 604. In certain vessels, contact forces between the therapeutic assembly 604 and the vessel wall can make it difficult to rotate the therapeutic assembly 604 distally and/or proximally. Likewise, a catheter and/or a sheath carrying the catheter 618 may be insufficiently flexible to match the curvature of anatomy near the treatment location, such as the curvature of a pulmonary artery between the MPA and the RPA and/or LPA. This may cause the catheter and/or the sheath to enter the body lumen out of alignment with a longitudinal axis of the body lumen. Because of the inner sheath 617 of the present technology, the guide catheter 616 and the inner sheath 617 can rotate along a central axis independently of one another. Moreover, the inner sheath 617 can be sufficiently flexible to de-couple at least the therapeutic assembly 604 (positioned within a relatively stable pulmonary vessel) from the catheter (e.g., the guide catheter 616) positioned within or nearer to the contracting and expanding heart. This feature can be advantageous because, for example, when at least a portion of the catheter and/or shaft is positioned within the heart, the guide catheter 616 often time translates the pumping movement of the heart to the therapeutic assembly 604. In addition, the inner sheath 617 can also selectively position the therapeutic assembly 604 relative to the vessel wall. For example, in some embodiments it may be advantageous to position the therapeutic assembly 604 at a central location within the vessel lumen before, during, or after energy delivery.

Figure 7A:
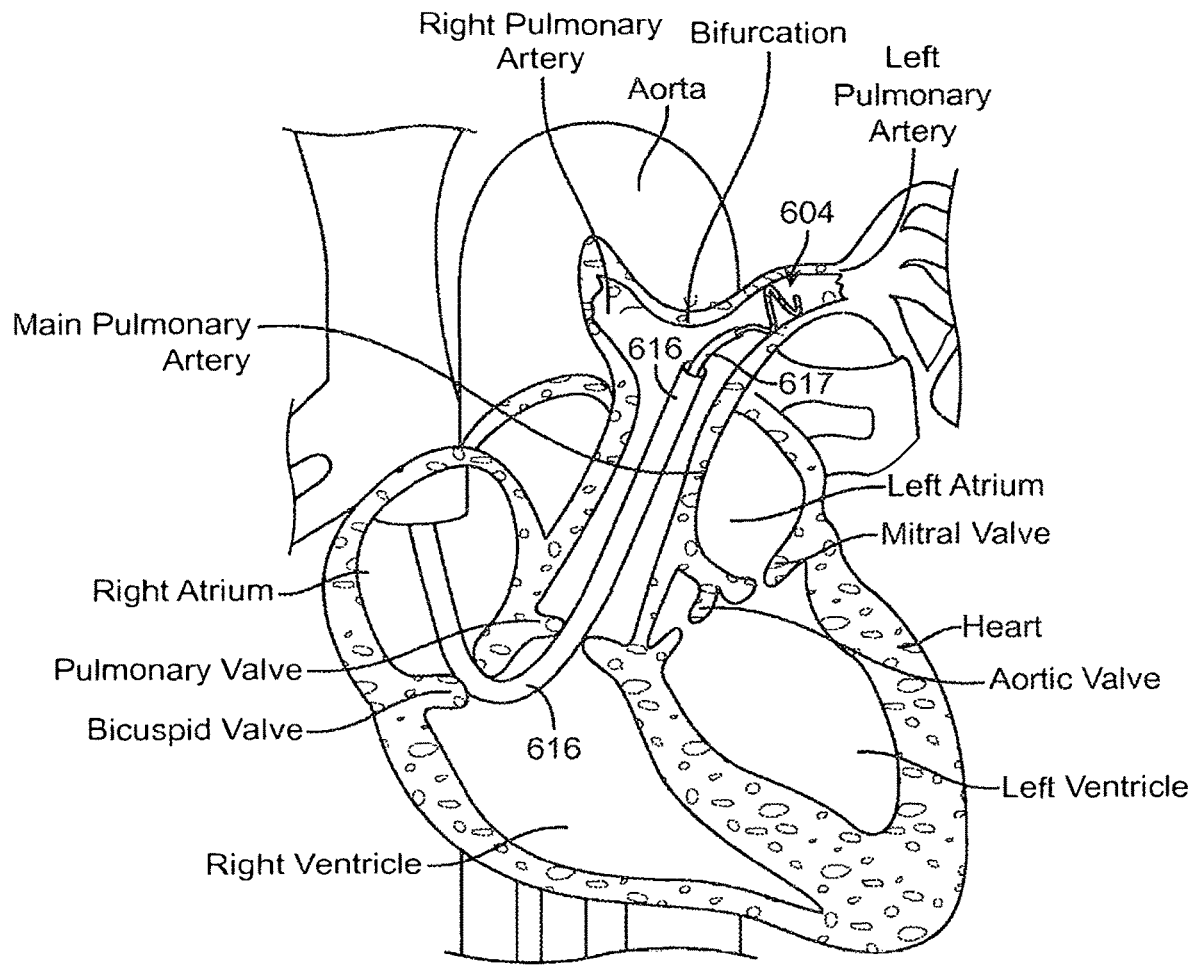
FIGS. 7A-7B are side views of a catheter having an inner sheath positioned within the left pulmonary artery configured in accordance with an embodiment of the present technology.
Figure 7B:
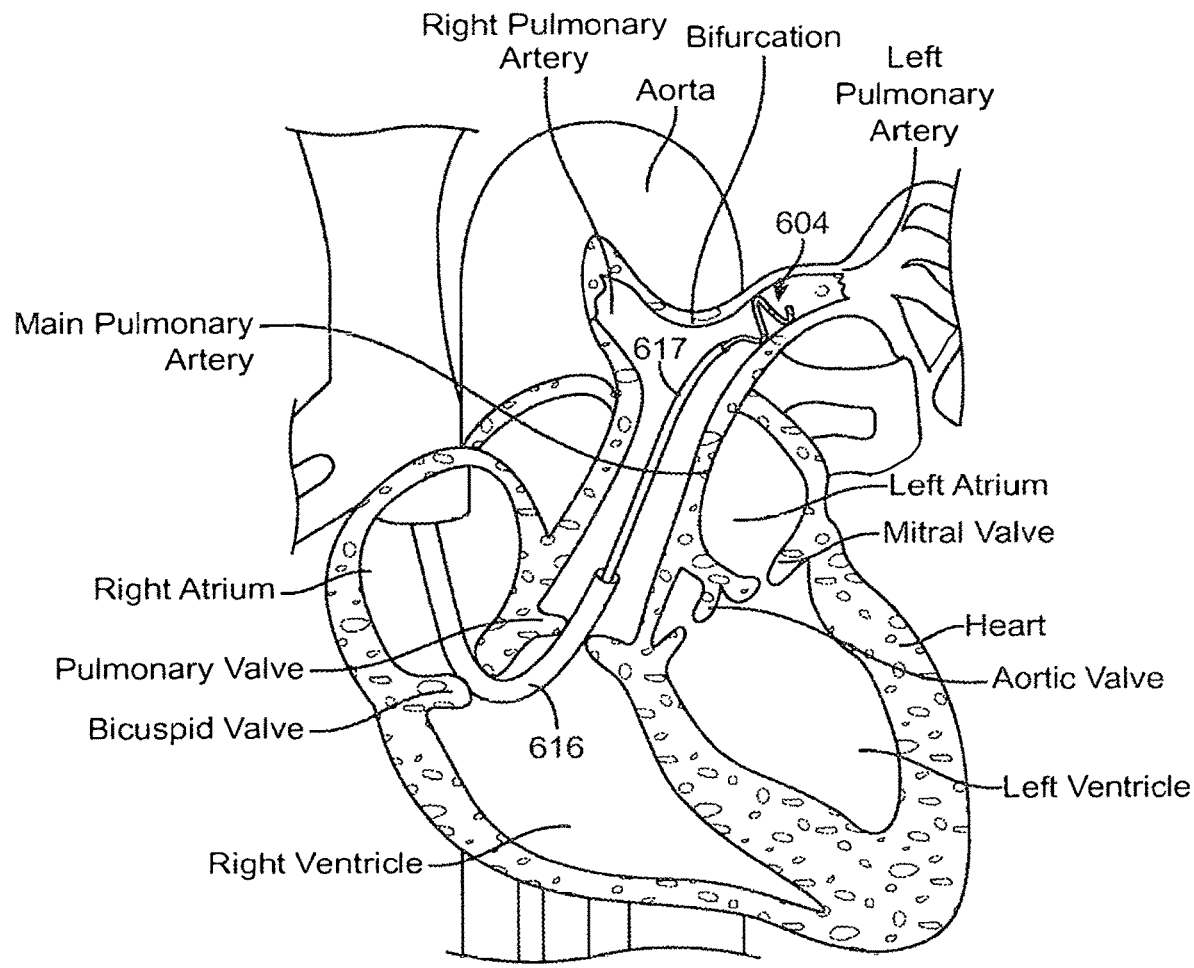

FIGS. 7A and 7B show examples of various deployment configurations of the catheter with the inner sheath 617. As shown in FIG. 7A, the shaft 616 can be advanced along the MPA just proximal to the ostium of the LPA (or RPA (not shown)). The inner sheath 617 (containing the therapeutic assembly 604) can then be advanced past the distal end of the shaft 616 and into the LPA for deployment of the therapeutic assembly 604. As shown in FIG. 7B, in some embodiments the shaft 616 can be advanced just distal of the pulmonary valve. The inner sheath 617 can then be advanced past the distal end of the shaft 616, past the bifurcation, and into the LPA for deployment of the therapeutic assembly 604.

B. Anchoring Devices and Methods

The PN systems and/or therapeutic assemblies discloses herein can include one or more anchoring devices for stabilizing the distal portion and/or therapeutic assembly relative to the vessel wall and/or selectively positioning the distal portion and/or therapeutic assembly relative to the vessel wall (e.g., at a central location within the vessel lumen, selectively offset from the center of the vessel lumen).

Figure 8:
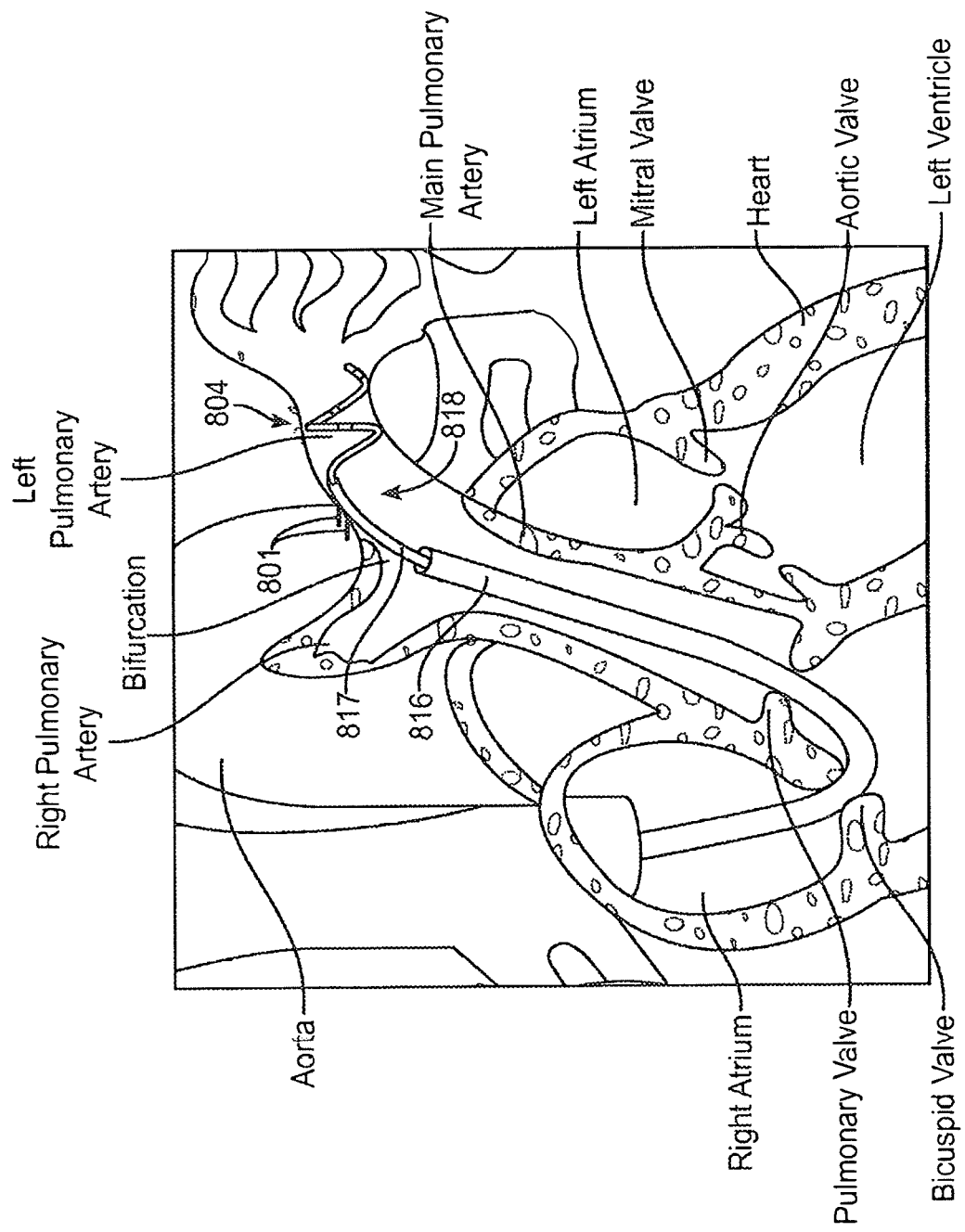
FIG. 8 is a side view of a therapeutic assembly in a deployed configuration having an anchoring device positioned within the left pulmonary artery in accordance with an embodiment of the present technology.

FIG. 8, for example, is a side view of another embodiment of a catheter shown in the deployed configuration within the LPA in accordance with the present technology. The catheter can be generally similar to the previously described catheters 110 or (referenced herein with respect to FIGS. 1-7A). However, as shown in FIG. 8, the catheter includes fixation members 801 (shown schematically for illustrative purposes only) along at least a portion of its shaft 816 and/or inner sheath 817. The fixation members 801 can be configured to contact the inner wall of the pulmonary vessel and stabilize the distal portion 818 and/or therapeutic assembly 804 with respect to the pulmonary vessel. Such stabilization can be advantageous because the pulmonary vessels constantly move as a result of the surrounding anatomy, particularly the contraction and relaxation of the heart, and also the respiratory cycle. As previously discussed, the most common intravascular approach to the pulmonary vessel involves the positioning of at least a portion of the catheter and/or shaft within the heart. As a result, the shaft translates the pumping movement of the heart to the therapeutic assembly 804. The fixation members 801 can stabilize at least the therapeutic assembly 804 within the pulmonary vessel so that movement of the catheter (e.g., the shaft 816) will not affect the alignment and/or contact of the therapeutic assembly 804 and the vessel wall. In some embodiments, the fixation members 801 can be atraumatic or non-tissue penetrating, and in other embodiments the fixation members 801 can be tissue-penetrating (e.g., embedded in the tissue by radial force). The fixation members 801 can have any size or configuration suitable to stabilize the therapeutic assembly 804 relative to the vessel.

Figure 9:
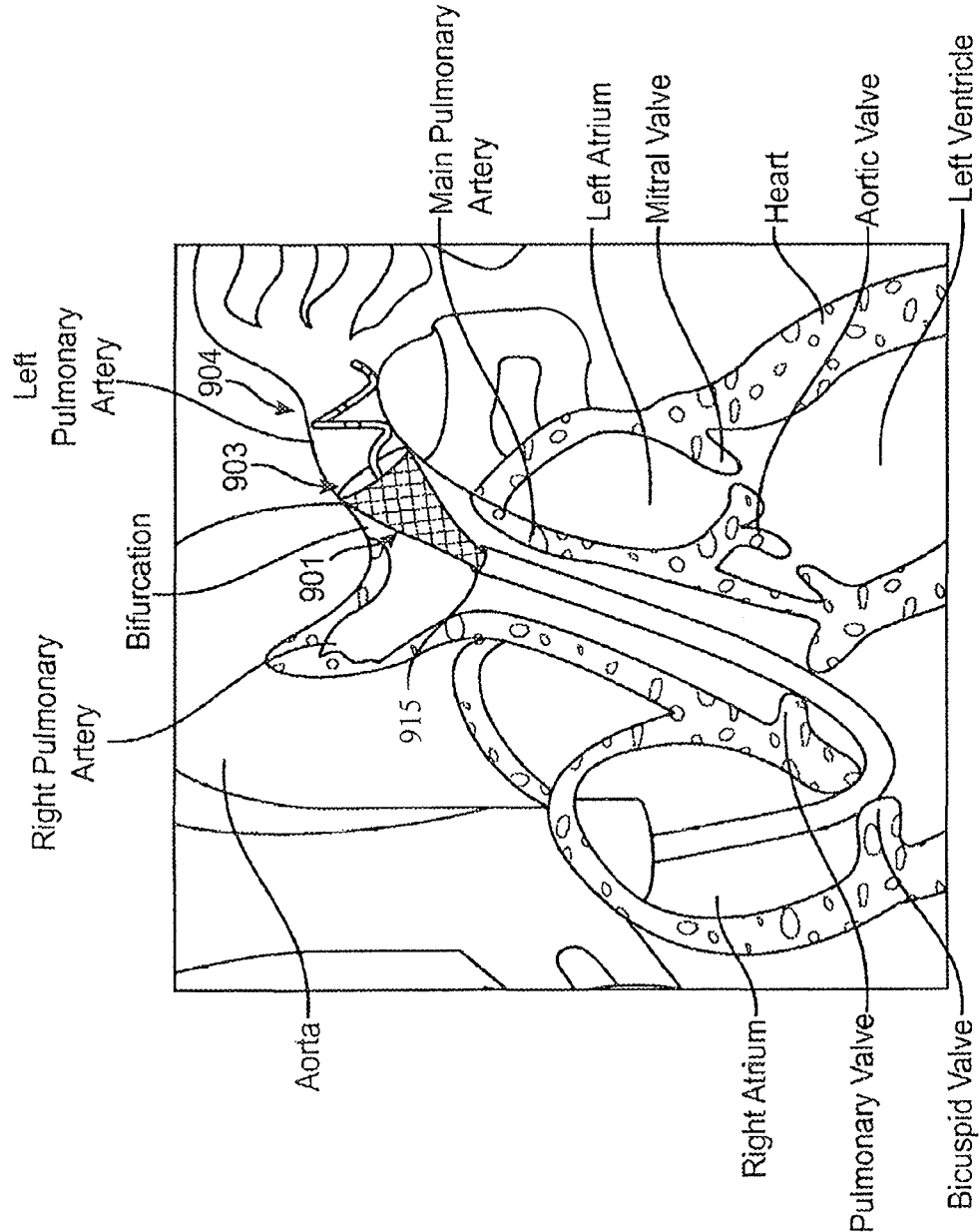
FIG. 9 is a side view of a therapeutic assembly in a deployed configuration having an anchoring device positioned within the left pulmonary artery in accordance with an embodiment of the present technology.

FIG. 9 is a side view of another embodiment of a catheter shown in the deployed configuration within the LPA in accordance with the present technology. The catheter can include an expandable inner sheath 901 that, when in the deployed configuration, expands to an outer radius generally equal to or greater than the inner radius of the vessel at the target location (e.g., a pulmonary vessel). As such, at least a distal end 903 of the sheath 901 can expand to engage the vessel wall thereby exerting a radially outward force against the vessel wall and stabilizing the sheath 901. In some embodiments, the sheath 901 can comprise an expandable stent-like structure which is collapsed in a delivery state within the elongated shaft 916 and expanded to a deployed state when advanced beyond a distal end 915 of the elongated shaft 916. Once deployed, the sheath 901 helps to mechanically isolate the therapeutic assembly 904 from the shaft 916. The sheath 901 can have a generally tapered shape such that the distal end 903 of the sheath 901 has a greater diameter than a proximal end (not shown). In some embodiments, at least a portion of the sheath 901 can include one or more fixation members configured to engage the vessel wall.

Figure 10:
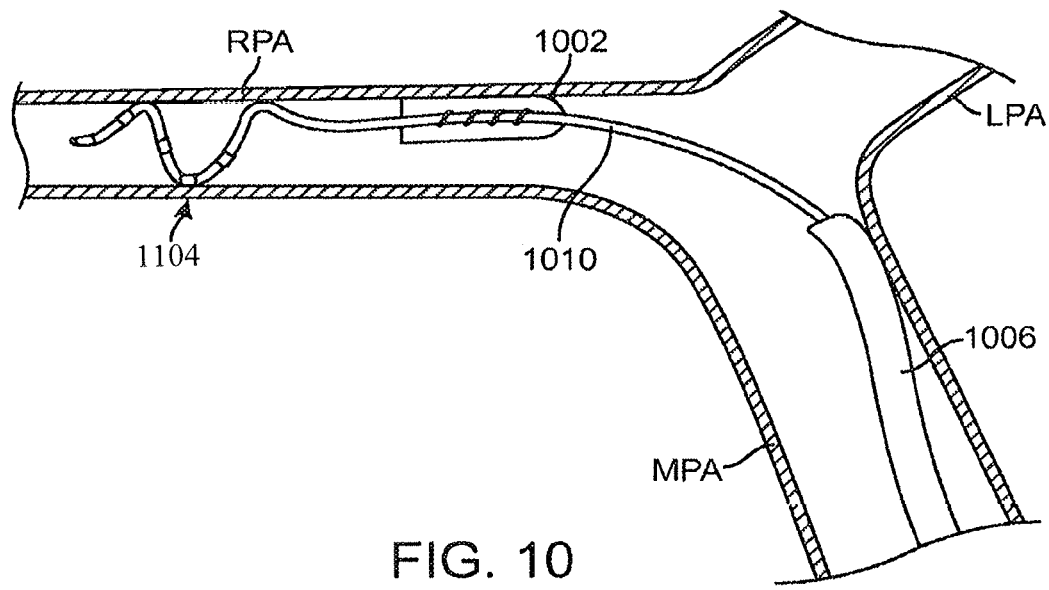
FIG. 10 is a side view of a therapeutic assembly having an anchoring device (shown in cross-section) within the right pulmonary artery in a deployed configuration in accordance with an embodiment of the present technology.

FIG. 10 is a side view of another embodiment of a catheter shown in the deployed configuration within the RPA in accordance with the present technology. The catheter can include a guide sheath 1006 and a circumferentially grooved or threaded elongated member 1010 slideably positioned therethrough. As shown in FIG. 10, the elongated member 1010 can be mated with an anchor 1002. Once deployed, the anchor 1002 can be fixed or secured to the vessel wall by frictional force and/or fixation members (not shown) (see FIG. 8 and accompanying description). In operation, insertion of the catheter 1017 from its proximal end (not shown) causes the therapeutic assembly 1004 to rotate in a distal direction while the anchor 1002 remains relatively generally stationary. In some embodiments (not shown), the anchor 1002 can be fixed to the guide sheath 1006.

Figure 11:
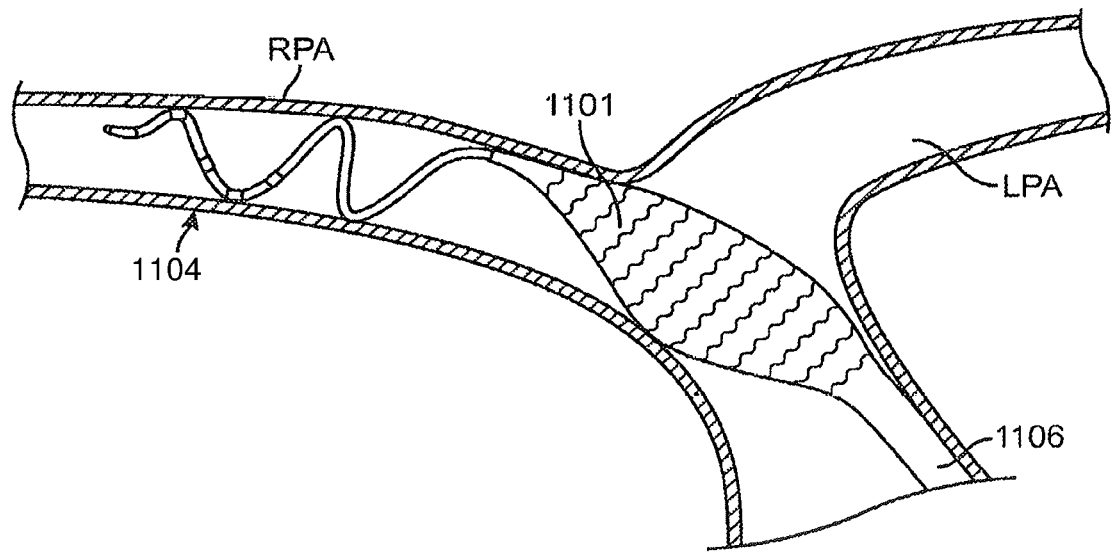
FIG. 11 is a side view of a therapeutic assembly having an anchoring device within the right pulmonary artery in a deployed configuration in accordance with an embodiment of the present technology.

FIG. 11 is a side view of another embodiment of a catheter shown in the deployed configuration within the RPA in accordance with the present technology. The catheter can include an expandable anchor 1101 configured to expand against at least a portion of the vessel wall and secure the therapeutic assembly 1104 relative to the local anatomy. For example, as shown in FIG. 11, once advanced distally past the catheter shaft 1106, the expandable anchor 1101 can expand and exert an outward force against the vessel wall. In particular embodiments, the anchor 1101 can engage and/or exert a contact force in one or more branches of the pulmonary artery simultaneously. For example, as shown in the illustrated embodiment, the anchor 1101 can span the bifurcation of the MPA into the LPA and/or RPA. Additionally, the anchor 1101 can have a tapered shape in the proximal and/or distal directions, and in other embodiments, the anchor 1101 can have a relatively uniform cross-sectional area along its length. In yet other embodiments, the anchor 1101 can have a main body and one or more branches (not shown) configured to be positioned within at least a portion of the MPA and the LPA or RPA, respectively. In some embodiments, the expandable anchor 1101 can be a stent, balloon, self-expanding basket or other suitable expandable or shape-changing structures or devices.

C. Tension-Relieving Devices and Methods

Figure 12:
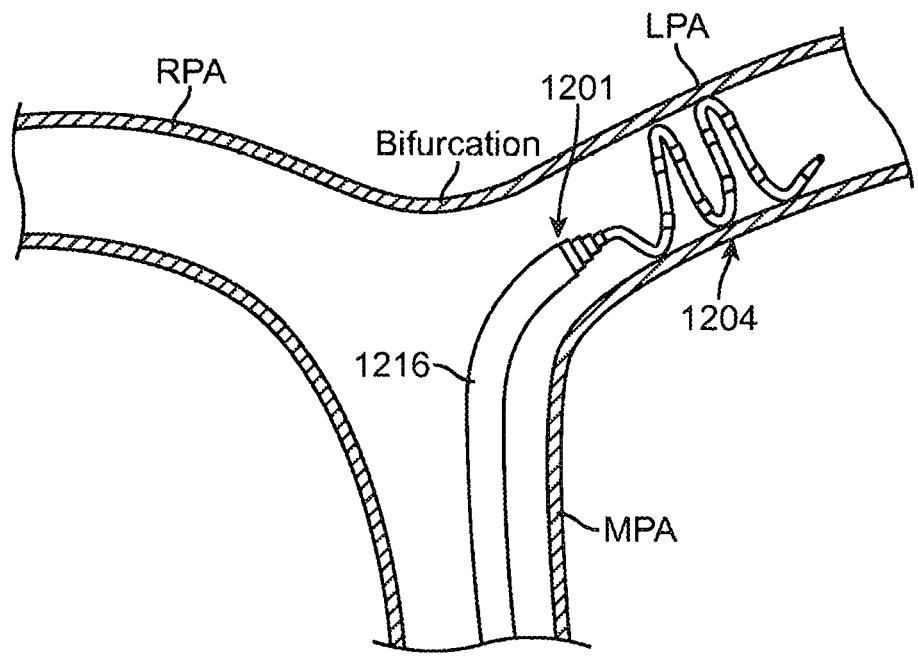
FIG. 12 is a side view of a therapeutic assembly having an extendable shaft within the left pulmonary artery in a deployed configuration in accordance with an embodiment of the present technology.

FIG. 12 is a side view of another embodiment of the catheter having a collapsible inner shaft 1201 configured in accordance with an embodiment of the present technology.

At least a proximal portion of the therapeutic assembly 1204 can be carried by the inner shaft 1201. As shown in FIG. 12, the inner shaft 1201 can have a "telescoping" design that allows the inner shaft 1201 to extend and retract freely such that proximal and distal movement of the shaft 1216 caused by the cardiac cycle, respiration, etc. will not pull or push the therapeutic assembly 104 out of position. Instead such motion is absorbed by the collapsible/extendable design of the inner shaft 1201. In some embodiments, the catheter can include a locking and/or activation mechanism (not shown) so that the timing and/or extent of the extension/retraction of the inner shaft 1201 can be controlled by the clinician. In further embodiments, the inner shaft can be corrugated along at least a portion of length to allow extension and retraction. Likewise, in a particular embodiment, the inner shaft 1201 can be a braided structure having a plurality of sections with alternating flexibility (e.g., by altering wire diameter, wire count, etc.) As a result, the sectioned inner shaft 1201 would allow for compression and extension with motion, thus mechanically isolating (at least in part) the therapeutic assembly 1204 from the shaft 1216.

Figure 13:
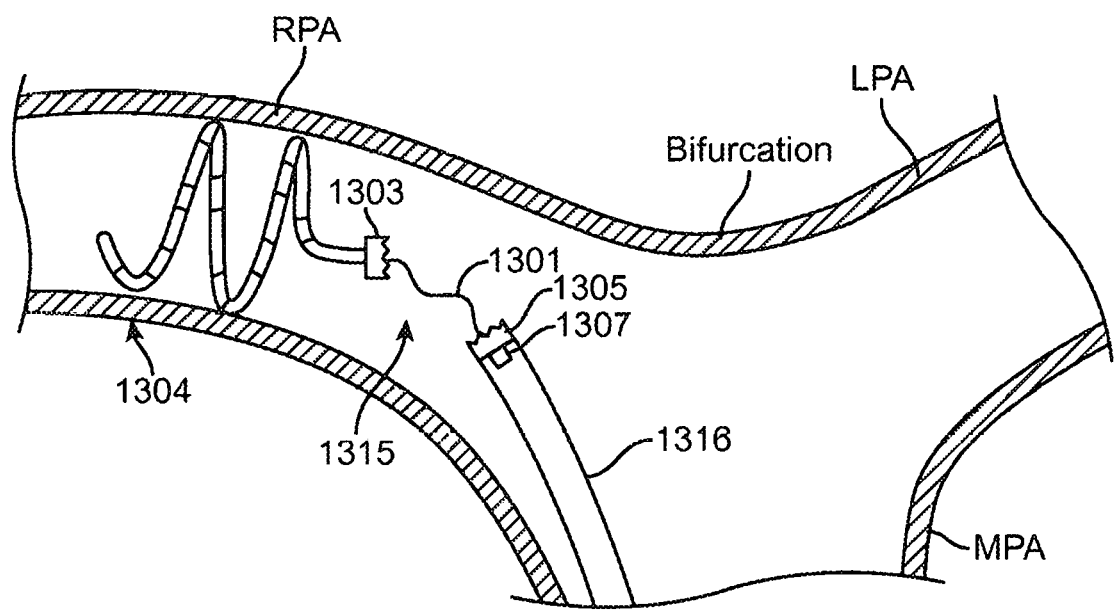
FIG. 13 is a side view of a therapeutic assembly mechanically isolated from the shaft within the right pulmonary artery in a deployed configuration in accordance with an embodiment of the present technology.

FIG. 13 is a side view of another embodiment of the catheter having a therapeutic assembly 1304 mechanically isolated from the shaft 1316 by an isolating element 1315. The isolating element 1315 can include a first portion 1303 operably connected to the therapeutic assembly 1304, a second portion 1305 operably connected to the shaft 1316, and a connector 1301 therebetween. The connector 1301 can have enough slack such that the position of the therapeutic assembly 1304 with respect to the vessel in which it is expanded is generally unaffected by movement of the shaft 1316. As discussed above, often times during cardiac contraction and relaxation the movement of the shaft 1316 is strong enough to pull or push the therapeutic assembly 1304 along the pulmonary vessel. For example, when the heart contracts, the shaft 1316 can be pulled distally by the contracting heart muscles, thereby pulling the therapeutic assembly 1304 distally (and likely out of position). The isolating element 1315 of the present technology mechanically isolates the therapeutic assembly 1304 from the catheter shaft 1316, allowing the shaft to move while the therapeutic assembly 1304 remains relatively stationary. In some embodiments, the catheter can include a locking and/or activation mechanism 1307 operably connected to the isolating element 1315 so that the timing of the release of the therapeutic assembly 1304 from the shaft 1316 can be controlled by the clinician. Additional devices and deployment methods for mechanical isolation of the therapeutic assembly from the shaft and/or catheter can be found in U.S. patent application Ser. No. 13/836,309, filed Mar. 15, 2013, titled "CATHETERS HAVING TETHERED NEUROMODULATION UNITS AND ASSOCIATED DEVICES, SYSTEMS, AND METHODS," which is incorporated herein by reference in its entirety.

Figure 14:
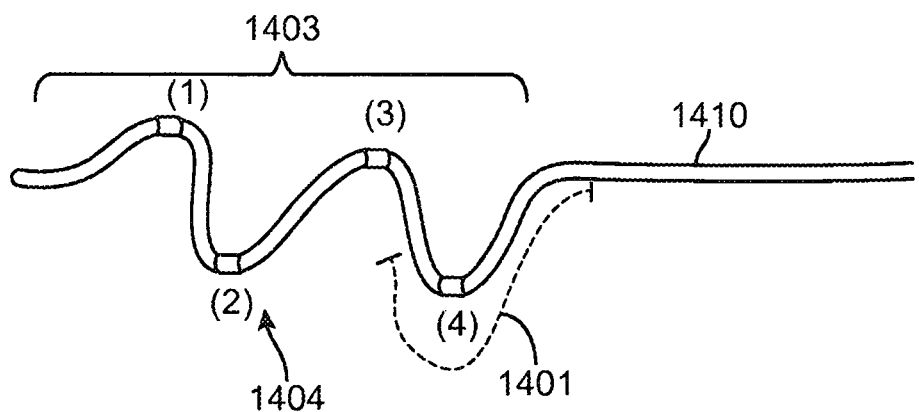
FIG. 14 is a side view of therapeutic assemblies in a deployed configuration in accordance with an embodiment of the present technology.
Figure 15:
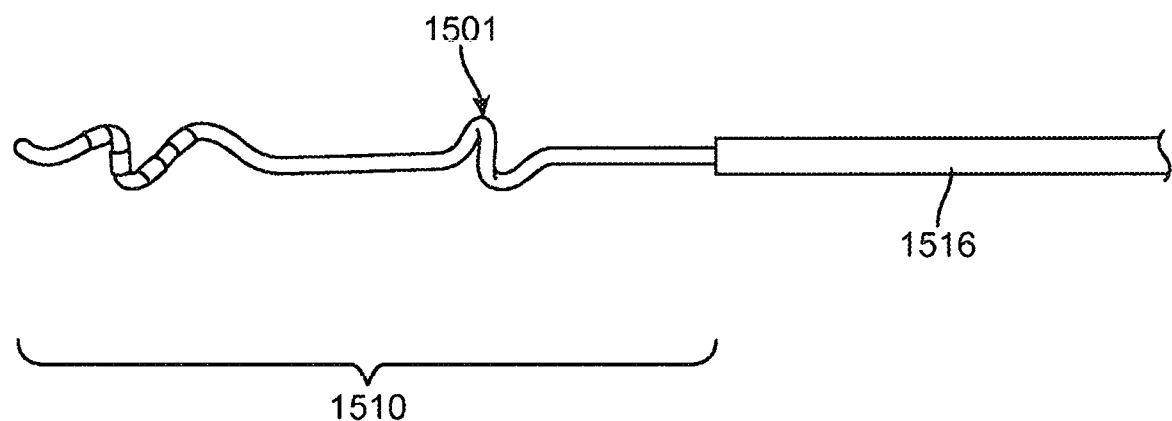
FIG. 15 is a side view of a therapeutic assembly having an inflection section in a deployed configuration in accordance with an embodiment of the present technology.

In some embodiments, the therapeutic assembly and/or support structure can be modified to relieve tension between therapeutic assembly and the shaft. For example, as shown in FIG. 14, the support structure 1410 can include an extended segment 1401 at a proximal section of the helical/spiral portion 1403 of the support structure 1410 and/or therapeutic assembly 1404. Such an extension can provide more slack and greater flexibility at the proximal section of the helical/spiral portion 1403. Additionally, one or more turns (labeled (1), (2), (3) and (4) in FIG. 14) can be added to the support structure 1410 to increase flexibility and/or the lengthening potential of the therapeutic assembly 1404. In a particular embodiment shown in FIG. 15, an inflection section 1501 can be included along the generally straight portion of the support structure 1510. Similar to the features described above with reference to FIG. 14, the inflection section 1501 can provide the added slack to absorb the disruptive motion of the shaft 1516.

D. Additional Embodiments

Figure 16A:
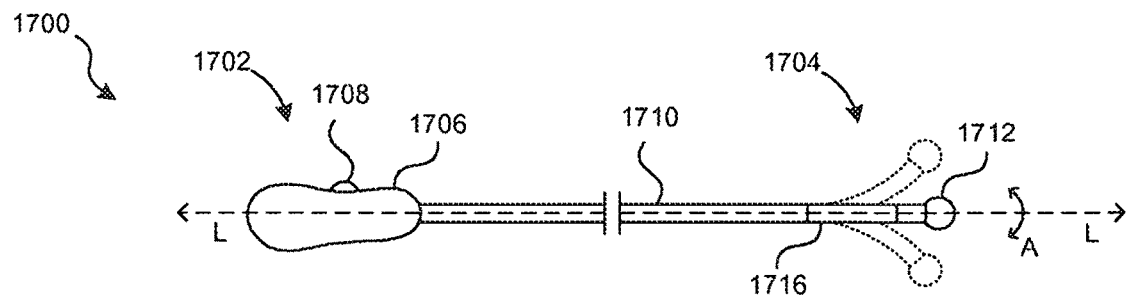
FIG. 16A is a side view of a catheter in a low-profile state configured in accordance with an embodiment of the present technology. A few exemplary deployed states are shown in phantom lines for purposes of illustration.

FIG. 16A is a side view of a catheter apparatus 1700 ("catheter 1700") configured in accordance with an embodiment of the present technology. The catheter 1700 can include a proximal portion 1702, a distal portion 1704, a handle assembly 1706 at the proximal portion 1702, and an elongated shaft 1710 extending distally from the handle assembly 1706. The distal portion 1704 of the elongated shaft 1710 can include an actuatable portion 1716 and one or more energy delivery elements 1712 (e.g., electrodes). For example, as shown in FIG. 16A, the catheter 1700 can include a single energy delivery element 1712 positioned at a distal-most portion of the shaft 1710. In other embodiments, the catheter 1700 can include more than one energy delivery element 1712 and/or one or more energy delivery elements 1712 can be positioned at any location along the length of the shaft 1710.

The handle assembly 1706 can include a control 1708 that is electrically coupled to the actuatable portion 1716 at the distal portion 1704 of the shaft 1710. For example, the catheter 1700 can include one or more wires (not shown in FIG. 16A) extending distally from the handle assembly 1706 through or along the shaft to the actuatable portion 1716. As indicated by arrow A, movement of the actuatable portion 1716 by the control 1708 can deflect, flex and/or bend the distal portion 1704 of the shaft 1710 to space the energy delivery element 1712 apart from a longitudinal axis L of the shaft 1710. Such movement by the actuatable portion 1716 can be used, for example, to place the energy delivery element 1712 in apposition with a vessel wall at a treatment site, as explained in greater detail below.

Figure 16B:
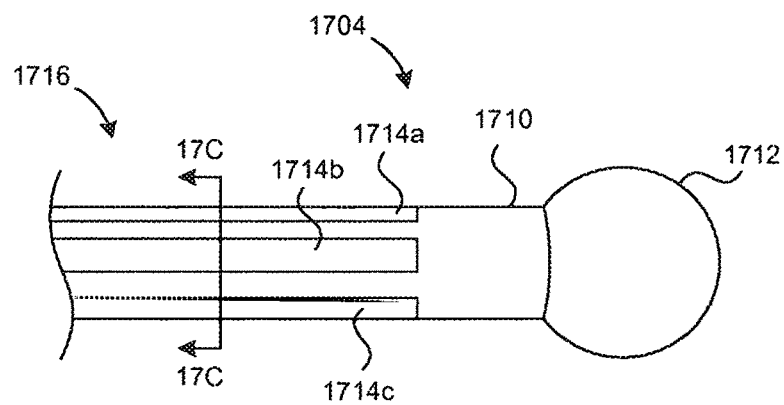
FIG. 16B is an enlarged side view of a portion of the distal portion of the catheter of FIG. 16A in a low-profile state configured in accordance with an embodiment of the present technology.
Figure 16C:
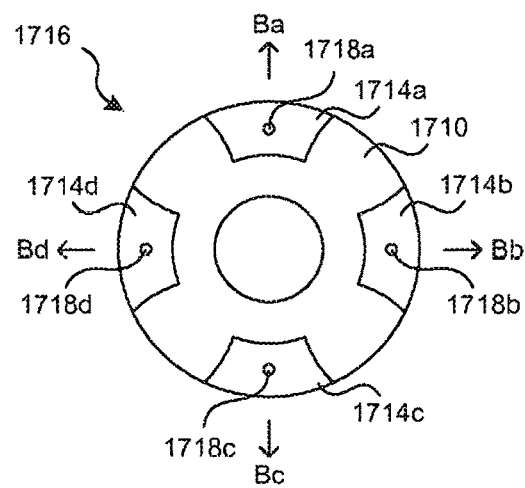
FIG. 16C is a cross-sectional end view of the shaft shown in FIG. 16B taken along the line 16C-16C.

FIG. 16B is an enlarged side view of a portion of the distal portion 1716, and FIG. 16C is a cross-sectional end view of the shaft 1710 taken along line 17C-17C in FIG. 16B. Referring to FIGS. 16A-16C together, the actuatable portion 1716 can include four deflectable members 1714a-d (referred to collectively as deflectable members 1714) spaced apart about the circumference of the shaft 1710. In the embodiment shown in FIGS. 16A-16C, the deflectable members 1714 are evenly spaced apart about the circumference of the shaft 1710 such that each deflectable member 1714a-d corresponds to a distinct quadrant of the shaft 1710. In other embodiments, the actuatable portion 1716 can include more or less than four deflectable members 1714 (e.g., one deflectable member, two deflectable members, six deflectable members, etc.) and/or the deflectable members 1714 can have any spacing about the shaft 1710. The deflectable members 1714 can have a length less than the length of the shaft. In one embodiment, the deflectable members 1714 can have a distal terminus spaced proximally of the energy delivery element 1712 and a proximal terminus within the distal portion 1704 of the shaft 1710. For example, the deflectable members 1714 can have a length of about 0.5 cm to about 10 cm, about 1 cm to about 5 cm, or more specifically about 1 cm to about 2 cm. Each of the deflectable members 1714a-d can include a wire 1718a-d running therethrough (referred to collectively as wires 1718). Each of the wires 1718a-d can extend proximally from a proximal portion one of the corresponding deflectable members 1714a-d along the shaft 1710 to the handle

1706. The wires 1718 can be electrically isolated from one another in the shaft 1710 (e.g., via separate lumens (not shown), embedding the wires in a polymer, etc.). As such, each of the deflectable members 1714a-d can be independently electrically controlled from the handle assembly 1706.

In operation, upon positioning the distal portion 1704 of the shaft 1710 at a treatment site adjacent a vessel wall (not shown), one or more of the deflectable members 1714 can be actuated to bend the distal portion 1704 in a desired direction. For example, selection of deflectable member 1714a (e.g., via the control) sends a current distally along the wire 1718a to the deflectable member 1714a, thereby causing the deflectable member 1714a to bend outwardly (see arrow $B_a$) and away from the longitudinal axis of the shaft 1710. The second-fourth deflectable members 1714b-d can be actuated in a similar fashion (see arrows $B_b$, $B_c$, $B_d$). The ability of the present technology to independently manipulate the distal portion of the shaft (relative to the rest of the shaft) can be advantageous, especially in a pulmonary setting, to compensate for the pulsatile, dynamic flow conditions present with vessels in close proximity to the heart. Moreover, such independent control can be advantageous to finely tune the deformation of the distal portion to position or navigate tortuous vasculature at and near the pulmonary system.

In some embodiments, the deflectable members 1714a-d can individually comprise a bimetallic strip including a first material having a first coefficient of thermal expansion (CTE) positioned adjacent a second material having a second coefficient of thermal expansion (CTE) that is different than the first CTE. The wires 1718a-d can be positioned between the first and second materials, and the first and second materials can be coupled to one another along their lengths. As the current flows through the wire 1718, the first and second materials begin to heat. Because the first and second materials have different CTE's, the lengths of the first and second materials will expand at different rates. As a result, the deflectable member will bend in the direction of the material with the lower CTE. In some embodiments, the first and second materials can comprise platinum (linear CTE of about 9 ($10^{-6}$ $K^{-1}$)), aluminum (CTE of about 22.2 ($10^{-6}$ $K^{-1}$)), silver (linear CTE of about 429 ($10^{-6}$ $K^{-1}$)), and steel (linear CTE of about 13 ($10^{-6}$ $K^{-1}$)).

Additionally, the deflectable members 1714a-d can individually comprise a piezoelectric material (e.g., an electrical-mechanical polymer) positioned on or adjacent a substrate material. The piezoelectric material and the substrate material can be coupled to one another along their lengths such that, when current is applied to the deflectable member (e.g., via the wire 1718), the piezoelectric material elongates while the substrate does not, thereby bending the deflectable member.

In some embodiments, the catheter 1700 can include a plurality of actuatable portions spaced apart along the length of the shaft 1710. When actuated, the plurality of actuatable portions can bend the shaft 1710 at multiple locations and/or in different directions. In such embodiments, the number, size, shape and/or spacing of the deflectable members can be the same or different amongst the actuatable portions.

Figure 17A:
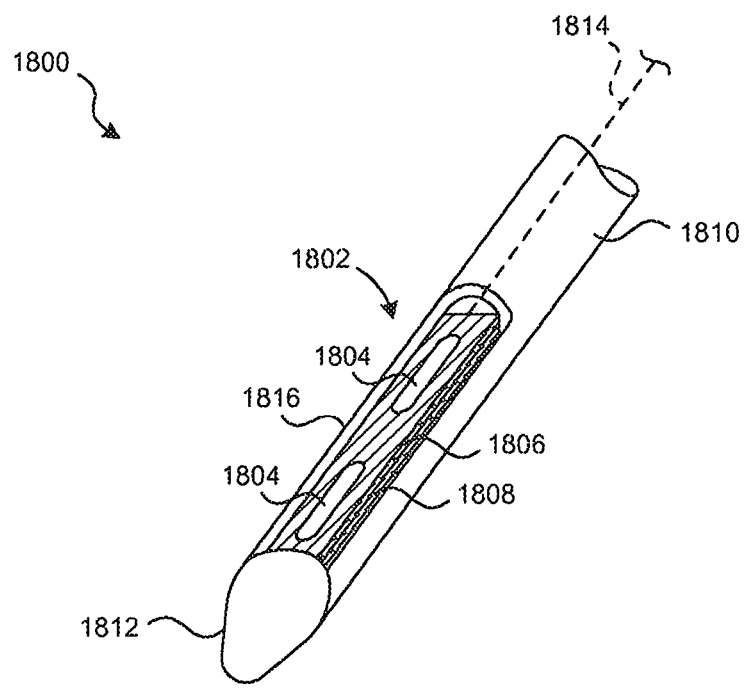
FIG. 17A is a perspective view of a distal portion of a catheter in a low-profile state configured in accordance with an embodiment of the present technology.
Figure 17B:
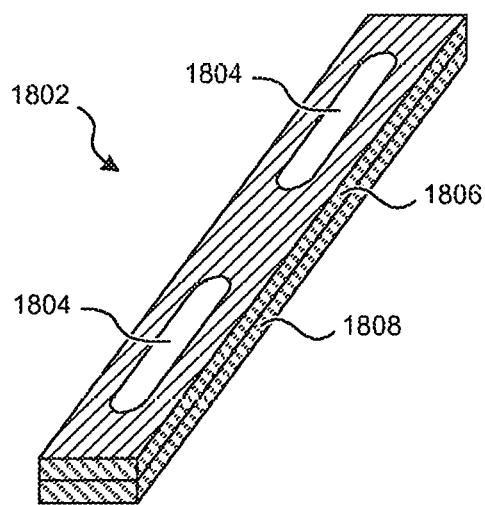
FIG. 17B is an isolated, enlarged view of the treatment member of FIG. 17A configured in accordance with an embodiment of the present technology.

FIG. 17A is a perspective view of a portion of a catheter 1800 in a low-profile state configured in accordance with another embodiment of the present technology. As shown in FIG. 17A, the catheter 1800 can include a shaft 1810 having a proximal portion (not shown) and a distal portion configured to be intravascularly positioned at a treatment site. The distal portion can include a recessed portion 1816 and an atraumatic distal end region 1812. The recessed portion 1816 can house a deformable member 1802. An isolated, enlarged view of the deformable member 1802 is shown in FIG. 17B. Referring to FIGS. 17A and 17B together, the deformable member 1802 can comprise a first conductive member 1806 positioned on a second conductive member 1808. The first and second members 1806, 1808 can individually comprise a metal. In some embodiments, the first member 1806 can be a first material having a first CTE and the second member 1808 can be a second material having a second CTE different than the first CTE. A wire 1814 extending from a proximal portion of the catheter 1800 (not shown) can be coupled to the first and second conductive members 1806, 1808. For example, the wire 1814 can be positioned between the first and second members 1806, 1808. The first and second conductive members 1806, 1808 can be coupled to one another along their lengths. In some embodiments, the first and second conductive members can individually comprise platinum (linear CTE of about 9 ($10^{-6}$ $K^{-1}$)), aluminum (CTE of about 22.2 ($10^{-6}$ $K^{-1}$)), silver (linear CTE of about 429 ($10^{-6}$ $K^{-1}$)), and steel (linear CTE of about 13 ($10^{-6}$ $K^{-1}$)).

Referring still to FIGS. 17A-17B, the first and second conductive members 1806, 1808 can be coated or otherwise surrounded by an insulative material. The first conductive member 1806 can include two energy delivery elements 1804 comprising an exposed portion of the first conductive member 1806 (e.g., an opening in the insulative material). In other embodiments, the deformable member 1804 can include more or less than two energy delivery elements (e.g., one energy delivery element, three energy delivery elements, etc.).

FIG. 17C is a side view of the distal portion of the catheter 1800 in a low-profile state, and FIG. 17D is a side view of the distal portion of the catheter 1800 in a deployed state. The sidewalls of the recessed portion 1816 are shown in phantom lines for ease of illustration. Referring to FIGS. 17A-17D together, as the current flows through the wire 1814, the first and second members conductive 1806, 1808 begin to heat. Because the first and second conductive members 1806, 1808 have different CTE's, the lengths of the first and second conductive members 1806, 1808 will expand at different rates. As a result, the deformable member 1802 will bend in the direction of the material with the lower CTE, thereby projecting away from the longitudinal axis of the shaft 1810 and into apposition with the vessel wall at the treatment site.

Figure 18:
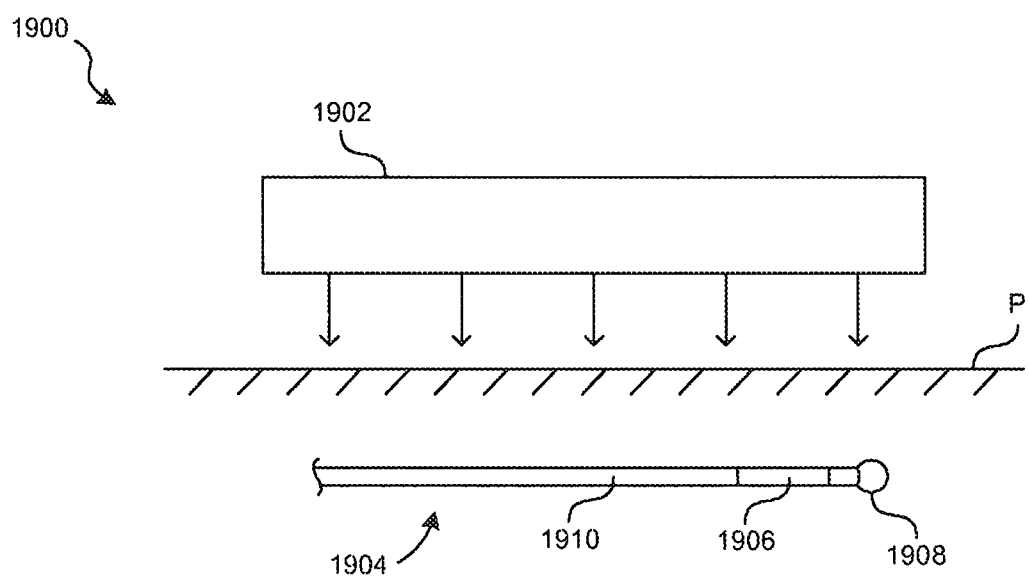
FIG. 18 is a schematic representation of a magnetically-deformable catheter system configured in accordance with an embodiment of the present technology.

FIG. 18 is a schematic representation of a magnetically-deformable catheter system 1900 configured in accordance with an embodiment of the present technology. As shown in FIG. 18, the catheter system 1900 can include a magnetic field generator 1902 (e.g., a magnetic resonance imaging (MRI) system, etc.) configured to be positioned external to the patient P and a catheter 1904. The catheter 1904 can include an elongated shaft 1910 and a magnetically actuatable portion 1906 coupled to a distal portion of the elongated shaft 1910. When the magnetic field generator 1902 is activated, the magnetic field deforms the magnetically actuatable portion 1906 of the shaft 1910 (not shown) to achieve a desired shaft 1910 configuration.

The catheter 1904 of FIG. 18 can have a single energy delivery element 1908 or, in other embodiments the catheter 1900 can include more than one energy delivery element 1908 positioned along the shaft 1910. Additionally, the catheter 1900 can include more than one magnetically actuatable portion 1906 positioned along the shaft 1910.

When modulating the nerves from within a pulmonary vessel, it is desirable to avoid total occlusion of the vessel since 100% of the body's blood flows through portions of the pulmonary vasculature (e.g., the MPA). Several of the catheters, catheter systems, and methods of the present technology provide non-occlusive means for effectively modulating the nerves communicating with the pulmonary system. In other embodiments, the catheters, catheter systems, and methods of the present technology can provide occlusive means for effectively modulating nerves communicating with the pulmonary system.

Figure 19:
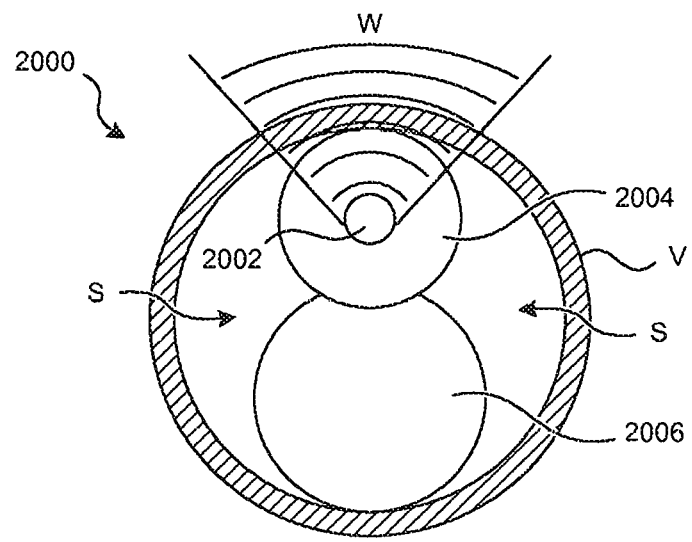
FIG. 19 is a cross-sectional end view of a non-occlusive catheter system shown deployed in a vessel and configured in accordance with an embodiment of the present technology.
Figure 20:
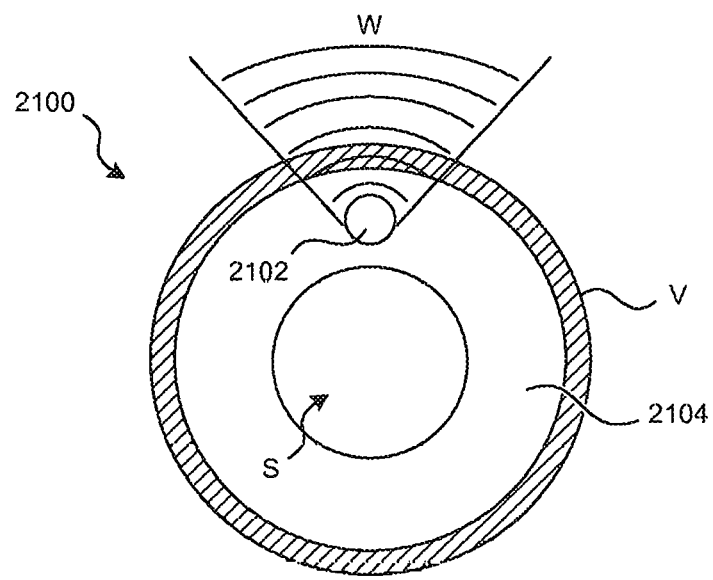
FIG. 20 is a cross-sectional end view of a non-occlusive catheter system shown deployed in a vessel and configured in accordance with another embodiment of the present technology.

FIGS. 19-20 are cross-sectional views of two additional embodiments of such non-occlusive catheters. FIG. 19 shows a non-occlusive catheter 2000 in a deployed state positioned in a vessel V and configured in accordance with an embodiment of the present technology. As shown in FIG. 19, the catheter 2000 can include an ultrasound transducer 2002 that produces sound waves (W), a first expandable member 2004 (e.g., a balloon, a wire cage, etc.) positioned around the ultrasound transducer 2002, and a second expandable member 2006 (e.g., a balloon, a wire cage, etc.) positioned adjacent the first expandable member 2004. When deployed, the first and second expandable members 2004, 2006 together position the ultrasound transducer 2002 near the vessel wall V at a desired distance to achieve effective neuromodulation. As shown in FIG. 19, the diameters of the first and second expandable members 2004, 2006 can be selected such that sufficient space S remains adjacent the catheter 2000 within the vessel V, thereby allowing blood flow during treatment.

FIG. 20 is a cross-sectional end view of another non-occlusive catheter 2100 in a deployed state positioned in a vessel V and configured in accordance with an embodiment of the present technology. As shown in FIG. 20, the catheter 2100 can include an ultrasound transducer 2102 positioned within a donut-shaped expandable member 2104 (e.g., a balloon, a wire cage, etc.). During treatment, blood can flow through the opening in the expandable member 2104. It will be appreciated that the expandable members of the present technology can have any suitable size, shape, and configuration. For example, in some embodiments, the expandable members can have a helical/spiral shape in a deployed state.

E. Nerve Monitoring Devices and Methods

Figure 21A:
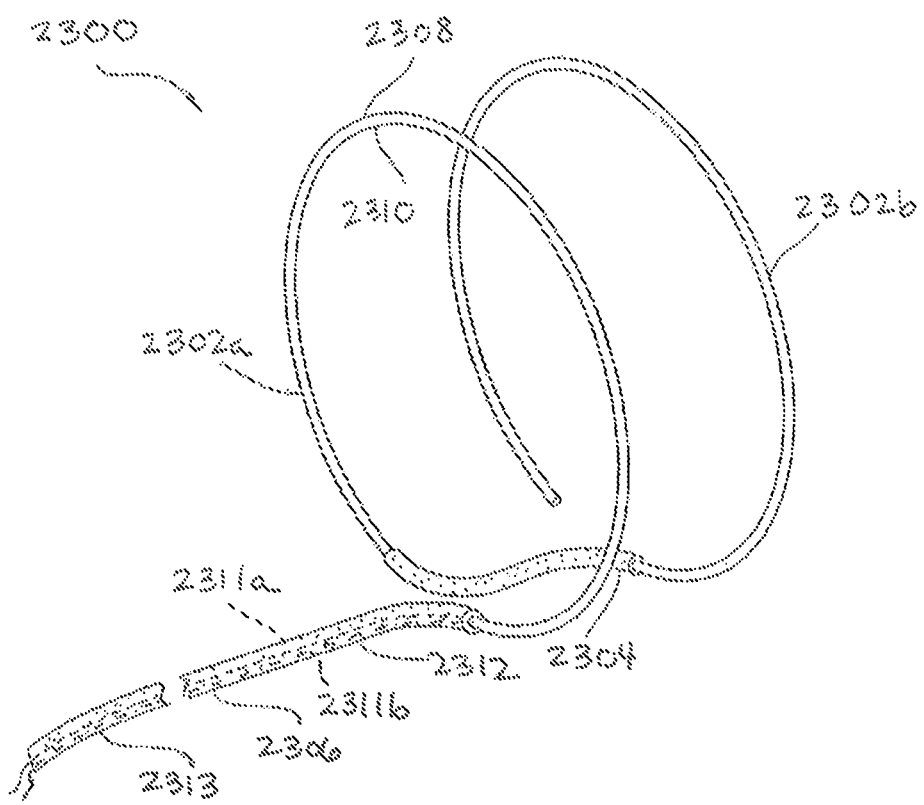
FIG. 21A is an enlarged isometric view of a therapeutic assembly configured in accordance with an embodiment of the present technology.

Any of the pulmonary neuromodulation systems and/or therapeutic assemblies described herein can be configured to stimulate nerves proximate the treatment site and/or record the resultant nerve activity. For example, several embodiments of the pulmonary neuromodulation systems and/or therapeutic assemblies described herein can include a nerve monitoring assembly. FIG. 21A, for example, is an enlarged isometric view of one embodiment of a nerve monitoring assembly 2300 (also referred to herein as "monitoring assembly 2300") configured in accordance with the present technology. The monitoring assembly 2300 is configured to provide stimulation to neural fibers and/or record activity of nerves in communication with the pulmonary system. As shown in FIG. 21A, the monitoring assembly 2300 can include a first loop electrode or conductor 2302a and a second loop electrode or conductor 2302b (referred to collectively as loop electrodes 2302) electrically isolated from the first loop electrode 2302a and positioned at a distal portion 2312 of an elongated catheter shaft 2306. In the illustrated embodiment, the two loop electrodes 2302 form a generally circular shape. However, the term "loop electrode" as used herein should be construed broadly to include electrodes 2302 having other shapes configured to contact at least a portion of the interior wall of a vessel. In various embodiments, the first loop electrode 2302a can be an anode, the other loop electrode 2302 can be a cathode, and an insulated portion 2304 can electrically isolate the anode and cathode loop electrodes 2302 from one another and space the loop electrodes 2302 laterally apart from one another. For example, the distal end of the first loop electrode 2302a and the proximal end of the second loop electrode 2302b can terminate at or within a portion of the insulating portion 2304, and the insulating portion 2304 can space apart the loop electrodes 2302. In various embodiments, the separation between the loop electrodes 2302 (e.g., provided by the insulating portion 2304) can be selected to enhance the signal to noise ratio for recording nerve activity (e.g., delta fibers and/or C-fibers). For example, the first and second loop electrodes 2302a and 2302b can be spaced about 5 mm apart from one another for recording action potentials from delta fibers, and may be positioned further apart from one another for recording C-fibers.

When the first and second loop electrodes 2302a and 2302b are configured as an anode and a cathode, the monitoring assembly 2300 can deliver bipolar stimulation to nerves proximate a target site in a vessel (e.g., nerves that communicate with the pulmonary system) or provide bipolar recording of nerve activity proximate the target site. For example, a nerve monitoring device configured in accordance with one embodiment of the present technology can include two electrode assemblies 2300: a first electrode assembly configured to stimulate nerves and a second electrode assembly spaced apart from the first electrode assembly along the vasculature and configured to measure the action potential of the nerves resulting from the stimuli of the first electrode assembly. Action potential is the electrical activity developed in a nerve cell during activity (e.g., induced by a stimulus from the first electrode assembly).

The loop electrodes 2302 can have an outer diameter at least equal to an inner diameter of a target vessel and, in some cases, larger (e.g., 1.5 times larger) than the inner diameter of the target vessel.

Each loop electrode 2302 can be made from a separate shape memory wire that defines the electrode 2302. The shape memory wire allows the loop electrodes 2302 to be positioned in a low profile, delivery state during intravascular delivery to the target vessel and open transverse to the longitudinal axis of the target vessel to an expanded or deployed state (shown in FIG. 21A). For example, the loop electrodes 2302 can be made from nitinol wires that can self-expand to a predefined shape upon delivery at the target vessel. In various embodiments, the shape memory material can be coated (e.g., sputter coated) with gold, platinum, platinum iridium, and/or other suitable materials. The coating can be selected to substantially optimize the impedance of the assembly 2300 and/or enhance the signal-to-noise ratio recorded by the electrode assembly 2300. In other embodiments, the loop electrodes 2302 can be made from other suitable materials (e.g., platinum, gold, platinum iridium, stainless steel, aluminum, etc.). The wire thickness of each loop electrode 2302 can be sized such that the loop electrode 2302 is stable enough to maintain its shape during nerve monitoring, yet flexible enough to allow for intravascular delivery in a low profile arrangement to a peripheral vessel (e.g., a pulmonary blood vessel).

Each loop electrode 2302 of the monitoring assembly 2300 can have an exposed abluminal surface 2308 (e.g., an outer surface proximate the vessel wall during nerve monitoring) to deliver and/or receive electrical signals to neural fibers proximate to a target vessel and an insulated adluminal or luminal surface 2310 (e.g., an inner surface facing away from the vessel wall and toward the lumen formed by the target vessel) to reduce the likelihood that blood flowing through the target vessel will short circuit the loop electrodes 2302. The luminal surface 2310 may be insulated using a coating with a high dielectric constant, strong adhesive properties to prevent it from rubbing off during delivery, biocompatible properties suitable for intravascular use, and/or other suitable characteristics.

As mentioned previously, the total exposed abluminal surface 2308 of the monitoring assembly 2300 can be selected to enhance the signal-to-noise ratio of the assembly 2300.

The monitoring assembly 2300 can be delivered intravascularly to a treatment site before and/or after neuromodulation. The distal portion 2312 of the shaft 2306 can be made from various flexible polymeric materials, such as a polyethylene block amide copolymer (e.g., PEBAX®, available from Arkema of France), high-density polyethylene (HDPE), nylon, polyimide, and/or other suitable materials, to facilitate navigation through tortuous vasculature. The distal portion 2312 can also include braid reinforcement comprised of polymeric materials to improve column strength, torque, and reduce kinking. A proximal portion (not shown) of the shaft 2306 can be more stiff than the distal portion 2312, and can therefore transmit force to track the shaft 2306 through the vasculature to the target site (e.g., proximate a pulmonary blood vessel). The proximal portion 2313 can be made from PERAX®, HDPE, low-density polyethylene (LDPE), nylon, polyimide, nylon, nitinol, a stainless steel hypotube, and/or other suitable materials. In various embodiments, the distal end portion of the assembly 2300 can include an atraumatic tip when the monitoring assembly 2300 is in the delivery state to reduce trauma to vessel walls as the monitoring assembly 2300 advances through the vasculature and deploys at the target site. This atraumatic tip material can be made from various soft materials, such as PEBAX®, LDPE, other polymers, and/or other suitable materials. The distal tip can also include a radiopaque tip marker (electrically isolated from the loop electrodes 2302) to provide visualization of the distal tip under fluoroscopy.

Signal wires 2311 (referred to individually as a first signal wire 2311a and a second signal wire 2311b; shown in broken lines) can be operatively coupled to the monitoring assembly 2300 to drive nerve stimulation, record nerve activity, and/or otherwise provide a signal to the loop electrodes 2302. The signal wires 2311, for example, can be welded, soldered, crimped, and/or otherwise connected to the shaft 2306. A distal portion of the first signal wire 2311a can be operably coupled to the first loop electrode 2302a, and a distal portion of the second signal wire 2311b can be operably coupled to the second loop electrode 2302b. The signal wires 2311 can extend through the shaft 2306 to a proximal end of the shaft where the signal wires 2311 can be operatively connected to a signal processing console (e.g., the energy generator 132 of FIG. 1) suitable for nerve stimulation. In various embodiments, for example, one or more electrode assemblies 2300 can be operatively coupled to a NIM-Response Nerve Integrity Monitor ("NIM") made available by Medtronic Xomed of Jacksonville, Fla., which provides intraoperative nerve monitoring capabilities using visual and/or audible indications of nerve activity. Additionally, in those embodiments where the catheter and/or treatment device includes an electrical element 211 (FIG. 2A), the signal wires 2311 can extend from the monitoring assembly 2300 to the electrical element 211. In such embodiments, the catheter can include an additional set of wires (not shown) that extends between (and electrically couples) the electrical element 211 and the energy generator 132.

Figure 21B:
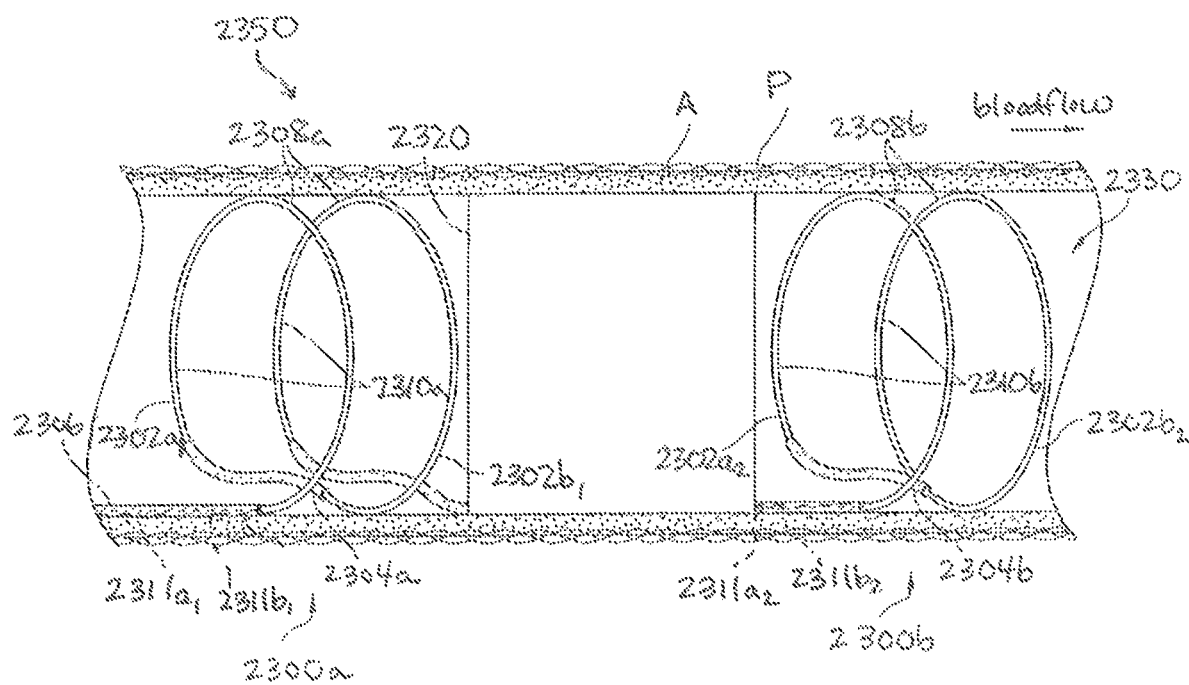
FIG. 21B is an enlarged partially schematic view of a distal portion of a treatment device within a blood vessel in accordance with an embodiment of the present technology.

FIG. 21B is an enlarged partially schematic side view of a distal portion 2350 positioned in a blood vessel A (e.g., a pulmonary blood vessel) and configured in accordance with an embodiment of the present technology. The distal portion 2350 can include a therapeutic assembly 2320 (shown schematically) and a nerve monitoring assembly 2330. The therapeutic assembly 2320 can include features generally similar to the features of the therapeutic assemblies described above with reference to FIGS. 1-20. The nerve monitoring assembly 2330 can be generally similar to the nerve monitoring assembly 2300 of FIG. 21A. In the illustrated embodiment, the therapeutic assembly 2320 is operatively coupled to and positioned between two electrode assemblies (identified individually as a first electrode assembly 2300a and a second electrode assembly 2300b) which together define the nerve monitoring assembly 2330. In other embodiments, the therapeutic assembly 2320 and the nerve monitoring assembly 2330 may be stand-alone devices that can be delivered independently to a target site (e.g., within the pulmonary artery). For example, in some embodiments the second electrode assembly 2300b, the therapeutic assembly 2320 and the first electrode assembly 2300a are coupled to separate catheter shafts and delivered sequentially to the target site to provide a configuration similar to that shown in FIG. 21B. In still other embodiments, the first and second electrode assemblies 2300a and 2300b can be integrally coupled to one another and delivered to the target site before and/or after neuromodulation. The distal end of the first loop electrode 2302a1 (or 2302a2) and the proximal end of the second loop electrode 2302b1 (or 2302b2) can terminate at or within a portion of the insulating portion 2304a (or 2304b), and the insulating portion 2304a (or 2304b) can space apart the loop electrodes 2302.

The nerve monitoring assembly 2330 can be configured to stimulate nerves in communication with the pulmonary system proximally with the first electrode assembly 2300a and record nerve activity distally with the second electrode assembly 2300b. The second electrode assembly 2300b can be positioned distal to the first electrode assembly 2300a. In further embodiments, the second electrode assembly 2300b can be configured to provide stimulation and the first electrode assembly 2300a can be configured to record the resultant nerve activity.

The first and second electrode assemblies 2300a and 2300b can be spaced far enough apart from one another such that the signal artifact associated with the bipolar stimulation from the first electrode assembly 2300a, which is less than that which would be produced by monopolar stimulation, does not substantially engulf or otherwise interfere with the signal being recorded at the second electrode assembly 2300b. The magnitude of the signal artifact at the second electrode assembly 2300b depends at least in part on the conduction velocity of the nerve fibers and the spacing between the stimulus and recording electrodes. C-fibers and delta-fibers, such as those found in nerves, have relatively low conduction velocities (e.g., no more than 2 m/s for C-fibers and about 3-13 m/s for delta fibers). As such, when the second electrode assembly 2300b is configured to record activity of nerves in communication with the pulmonary system, the second electrode assembly 2300b can be positioned laterally apart from the first electrode assembly 2300a along the axis of the pulmonary vessel A to reduce the signal artifact recorded by the second electrode assembly 2300b. In further embodiments, at least one of the electrode assemblies 2300 can be positioned outside the pulmonary blood vessel A. For example, in some embodiments the second electrode assembly 2300b can be positioned in the pulmonary blood vessel A to record nerve activity, and the first electrode assembly 2300a can be positioned elsewhere within the vasculature that can deliver a stimulus to nerves in communication with the pulmonary system. In still other embodiments, the first electrode assembly 2300a can be configured to stimulate nerves from a location outside the human body (e.g., at the brain stem), and the second electrode assembly 2300b can be configured to record the resultant nerve activity at a site within or proximate to the pulmonary blood vessel A. In additional embodiments, the electrode assemblies 2300 can be configured to be placed at other suitable locations for stimulating and recording nerve activity.

In various embodiments, the first electrode assembly 2300a can be configured to provide biphasic and bipolar stimulation. The second loop electrode $2302b_1$ (i.e., the electrode closest to the recording/second electrode assembly 2302b) can be a cathode and the first loop electrode $2302a_1$ an anode. The second electrode assembly 2300b can be configured to provide bipolar recording of nerve activity resulting from the stimulation induced by the first electrode assembly 2300a. As such, the first loop electrode $2302a_2$ can be one of an anode or a cathode, and the second loop electrode $2302b_2$ can be the other of the anode or the cathode. The second electrode assembly 2300b can pick up the relatively small action potentials associated with activity of nerves in communication with the pulmonary system, and can be sensitive to relatively small signals to differentiate nerve stimulation from noise. In order to pick up the small action potentials and differentiate the nerve activity from noise (e.g., from the signal artifact, action potentials of proximate muscle fibers, etc.), the second electrode assembly 2300b can be configured to record a plurality of samples that can be averaged (e.g., using an NIM or other suitable console). In one embodiment, for example, the second electrode assembly 2300b can average 160 samples within 12 seconds to identify the nerve activity. In other embodiments, more or less samples can be averaged to identify the nerve activity.

As shown in FIG. 21B, the first and second electrode assemblies 2300a and 2300b and the therapeutic assembly 2320 can be attached to the distal portion 2312 of the same shaft 2306 such that the nerve monitoring assembly 2330 and the therapeutic assembly 2320 can be delivered as a unit to the target site. In one embodiment, for example, the therapeutic assembly 2320 includes a neuromodulation loop electrode that is connected between the first and second electrode assemblies 2300a and 2300b. The first and second electrode assemblies 2300a and 2300b can be stiffer than the neuromodulation loop electrode such that the electrode assemblies 2300a-b stay substantially planar in the vessel A and provide adequate contact with the arterial walls to stimulate the nerves and record the resultant nerve activity. The neuromodulation loop electrode may be more flexible, allowing it to be pulled into a helix or corkscrew configuration during deployment at the target site while the first and second electrode assemblies 2300a and 2300b stay anchored against the vessel A due to self-expansion. In other embodiments, each electrode assembly 2300a-b and/or the therapeutic assembly 2320 can be attached to separate shafts and delivered independently to the target site.

In various embodiments, the nerve monitoring assembly 2330 (in conjunction with or independent of the therapeutic assembly 2320) can be delivered intravascularly to the pulmonary artery A or other peripheral vessel via a delivery sheath (not shown). The delivery sheath can extend along the length of the shaft 2306, and can be made from PEBAX®, nylon, HDPE, LDPE, polyimide, and/or other suitable materials for navigating the vasculature. The delivery sheath can cover the electrode assemblies 2300a-b such that they are positioned in a low profile, delivery state suitable for navigation through the vasculature. At the pulmonary vessel A, the delivery sheath can be moved relative to the electrode assemblies 2300a-b (e.g., the sheath can be retracted or the electrode assemblies 2300a-b can be advanced) to expose the electrode assemblies 2300a-b from the sheath 2300. This allows the electrode assemblies 2300a-b to deploy (e.g., self-expand) into an expanded state where the abluminal surfaces 2308 of the loop electrodes 2302 contact the vessel wall. In other embodiments, the delivery sheath is not integrated with the nerve monitoring assembly 2330, and is advanced over a guide wire to the treatment site via a guide catheter. In this embodiment, the delivery sheath can be made from a soft, flexible material that allows it to navigate tortuous vessels. Once the delivery sheath is at the target site in the pulmonary vessel A, the electrode assemblies 2300a-b can be positioned in a proximal opening of the delivery sheath and advanced distally to the treatment site where they can be deployed to the expanded state by moving the delivery sheath and the electrode assemblies 2300a-b relative to one another.

As shown in FIG. 21B, in the expanded state, the loop electrodes 2302 of the first and second electrode assemblies 2300a and 2300b are sized to press against or otherwise contact the interior wall of the pulmonary vessel A. The nerve monitoring assembly 2330 can first monitor nerve activity in real time before neuromodulation by delivering an electrical current proximal to a treatment site via the first electrode assembly 2300a and recording the resultant nerve activity at the second electrode assembly 2300b. The first and second loop electrodes $2302a_1$ and $2302b_1$ of the first electrode assembly 2300a can be operably coupled to first and second signal wires $2311a_1$ and $2311b_1$, respectively, to provide bipolar stimulation, and the first and second loop electrodes $2302a_2$ and $2302b_2$ of the second electrode assembly 2300b can be operably coupled to two separate signal wires $2311a_2$ and $2311b_2$, respectively, to provide bipolar recording, or vice versa. Since the abluminal surface 2308 (e.g., 2308a and 2308b) of the loop electrodes 2302 are fully exposed, the first electrode assembly 2300a can deliver stimulation to nerves positioned around the full circumference of the pulmonary vessel A. The exposed abluminal surface 2308 also allows the second electrode assembly 2300b to capture nerve activity regardless of nerve orientation around the circumference of the vessel A. The insulated luminal surface 2310 (e.g., 2310a and 2310b) of the loop electrodes 2302 insulates the electrode assemblies 2300 from blood flowing through the pulmonary vessel A to avoid a short circuit between the electrode loops 2302. The recording can be visualized using a console (e.g., an NIM) coupled to the proximal portion (not shown) of the shaft 2306.

The therapeutic assembly 2320 can then apply an energy field to the target site to cause electrically-induced and/or thermally-induced partial or full denervation of the nerves in communication with the pulmonary system (e.g., using electrodes or cryotherapeutic devices). The nerve monitoring assembly 2330 can again stimulate and record the nerve activity to determine whether sufficient neuromodulation occurred. If the nerve monitoring assembly 2330 indicates the presence of a higher level of nerve activity than desired, the therapeutic assembly 2320 can again apply the energy field to effectuate neuromodulation. This process of supplying a current, recording the resultant nerve activity, and applying neuromodulation to the treatment site can be repeated until the desired nerve lesion is achieved. In some embodiments, such as when the therapeutic assembly 2320 uses cryotherapeutic cooling, the nerve monitoring assembly 2330 can also record nerve activity during denervation. Once nerve monitoring at the treatment site is complete, the delivery sheath can again be advanced over the electrode assemblies 2300a-b and/or the electrode assemblies 2300a-b can be retracted into the delivery sheath, thereby moving the electrode assemblies 2300a-b back into the delivery state for removal from the patient.

In further embodiments, the nerve monitoring assembly 2330 can be operatively coupled to the therapeutic assembly 2320 such that nerve monitoring and neuromodulation can run automatically as part of a preset program. In other embodiments, the nerve monitoring assembly 2330 is not positioned around the therapeutic assembly 2320, but instead delivered to the treatment site separately before and/or after neuromodulation by the therapeutic assembly 2320.

In various embodiments, the first and second electrode assemblies 2300a and 2300b can be delivered after neuromodulation to confirm the desired neuromodulation has occurred. For example, the two electrode assemblies 2300a-b can be delivered proximate the treatment site as separate components or as an integrated unit to a vessel (e.g., the pulmonary vessel) during the neuromodulation procedure a short time after neuromodulation occurs (e.g., 5 minutes after neuromodulation). In other embodiments, the electrode assemblies 2300a-b can be used to monitor nerve activity during a separate procedure following the neuromodulation procedure (e.g., 1, 2 or 3 days after the neuromodulation procedure).

Figure 22A:
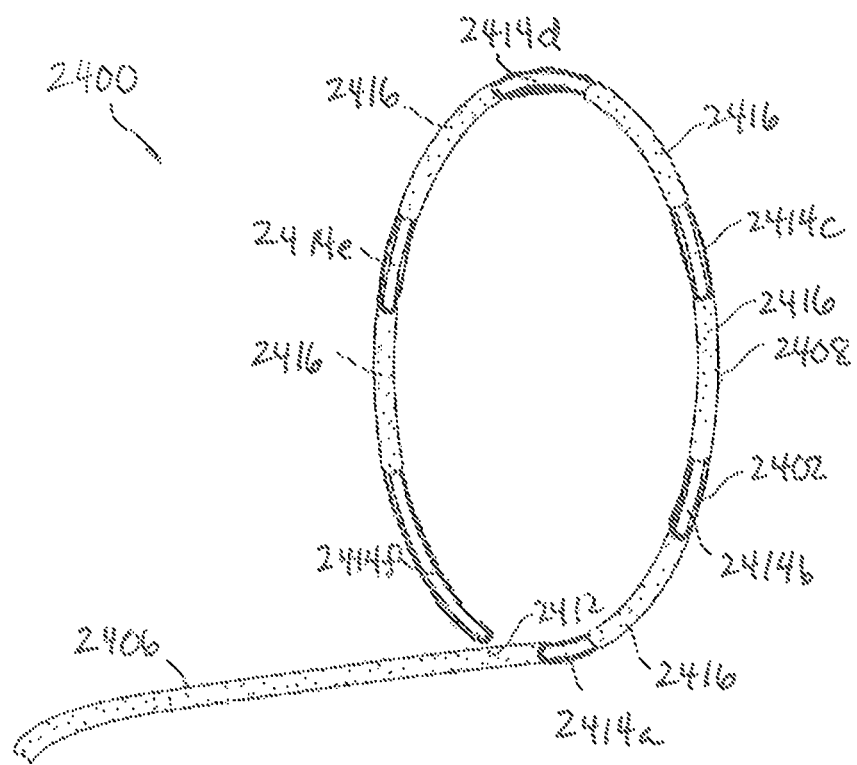
FIG. 22A is an enlarged isometric view of an electrode assembly configured in accordance with another embodiment of the present technology.

FIG. 22A is an enlarged isometric view of an electrode assembly 2400 configured in accordance with another embodiment of the present technology. The electrode assembly 2400 can include features generally similar to the assembly 2300 described above with reference to FIGS. 21A and 21B. For example, the electrode assembly 2400 includes a loop 2402 (e.g., a nitinol wire) at a distal portion 2412 of an elongated shaft 2406 that is configured to provide bipolar, biphasic nerve stimulation and/or record the resultant nerve activity. However, the electrode assembly 2400 shown in FIG. 22A includes a plurality of electrodes 2414 (identified individually as first through sixth electrodes 2414a-f, respectively) positioned around the circumference of the loop 2402 spaced apart and electrically insulated from one another by insulating sections 2416. The electrodes 2414 can be made from stainless steel, gold, platinum, platinum iridium, aluminum, nitinol, and/or other suitable materials, and the insulation sections 2416 can be made from a suitable dielectric material (e.g., a high-k dielectric with strong adhesive properties). The electrodes 2414 can be substantially coplanar with an outer surface of the insulating sections 2416 and/or the shaft 2406, or may project beyond the insulating sections 2416 by a distance. In various embodiments, for example, the electrodes 2414 can extend a radial distance from the adjacent insulating portions 2416 and include a smoothed edge (e.g., a beveled edge) to reduce denuding of the adjacent arterial wall. The coplanar or projecting electrodes 2414 can facilitate contact with the arterial wall to enhance stimulation and/or recording. In other embodiments, one or more of the electrodes 2414 may be recessed from the insulating portions 416.

In the illustrated embodiment, the multi-electrode loop 2402 includes six electrodes 2414a-f, which may be suitable for loops having outer diameters of approximately 8 mm. In other embodiments, however, the loop 2402 can include more or less electrodes 2414 (e.g., four to eight electrodes 2414) depending at least in part on the outer diameter of the loop 2402. Each of the electrodes 2414 can be designated as a cathode, anode, or inactive by a nerve monitoring console (e.g., an NIM and/or other suitable console) operably coupled to the multi-electrode loop 2402 via signal wires extending through the shaft 2406. For example, the electrodes 2414 can alternate as anodes and cathodes around the circumference of the loop 2402 (e.g., the first, third and fifth electrodes 2414a, 2414c and 2414e can be anodes and the second, fourth and sixth electrodes 2414b, 2414d and 2414f can be cathodes) such that the single loop 2402 can provide bipolar stimulation or recording. Similar to the loop electrodes 2302 described above, a luminal surface 2410 of the multi-electrode loop 2402 can also be insulated to inhibit short circuits across the electrodes 2414 (e.g., via blood or other conductive pathways), while an abluminal surface 2408 can remain exposed to allow the electrodes 2414 to contact a vessel wall (e.g., the pulmonary blood vessel).

In various embodiments, the electrode assembly 2400 can include two loops 2402 spaced laterally apart from one another (e.g., similar to the dual loop electrode assembly 2300 shown in FIG. 21A). This arrangement allows all the electrodes 2414 on one multi-electrode loop 2402 to be configured as anodes, while all the electrodes 2414 on the other multi-electrode loop 2402 can be configured as cathodes. Much like the loop electrodes 2302 shown in FIG. 21A, the double multi-electrode loop configuration can increase the surface area with which the electrode assembly 2400 can stimulate and/or capture nerve activity, and can therefore enhance nerve monitoring.

Figure 22B:
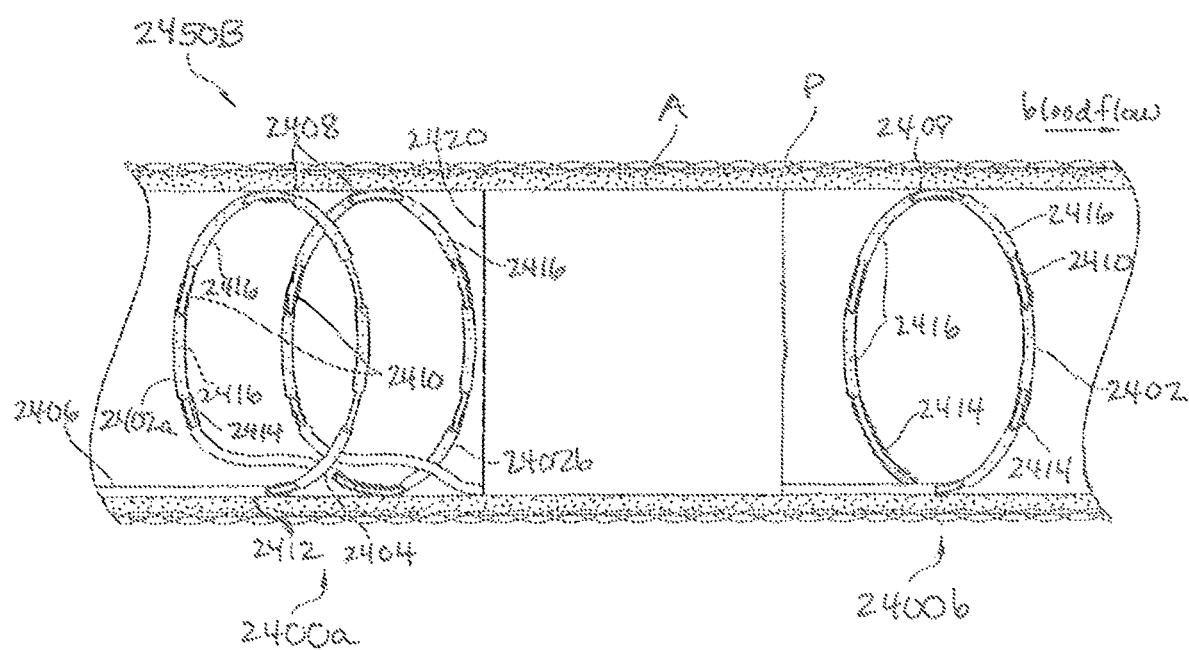
FIG. 22B is an enlarged partially schematic view of a distal portion of a treatment device within a blood vessel in accordance with another embodiment of the present technology.

FIG. 22B is an enlarged partially schematic side view of a distal portion of a treatment device 2450B within a blood vessel A (e.g., a pulmonary vessel) configured in accordance with another embodiment of the present technology. The treatment device 2450B includes features generally similar to the features of the treatment device 2350 described above with reference to FIG. 21B. For example, the treatment device 2450B includes a therapeutic assembly 2420 positioned between and optionally operably coupled to a first electrode assembly 2400a and a second electrode assembly 2400b. The first electrode assembly 2400a includes two multi-electrode loops 2402 (identified individually as a first multi-electrode loop 2402a and a second multi-electrode loop 2402b). In various embodiments, all the electrodes 2414 of the first multi-electrode loop 2402a can be anodes, and all the electrodes 2414 of the second multi-electrode loop 2402b can be cathodes such that the first electrode assembly 2400a can provide bipolar nerve stimulation. In the embodiment illustrated in FIG. 22B, the second electrode assembly 2400b includes one multi-electrode loop 2402 having both anodes and cathodes spaced around the circumference to provide bipolar recording of nerve activity. In other embodiments, the second electrode assembly 2400b can include two multi-electrode loops 2402 and designate one as a cathode and the other as an anode. An insulated portion 2404 can space the multi-electrode loops 2402a and 2402b laterally apart from one another. In further embodiments, the first electrode assembly 2400a and/or the second electrode assembly 2400b can include two bare loop electrodes 2302 as shown in FIG. 21B. In still further embodiments, the electrode assemblies 2400 can be configured to provide monopolar nerve stimulation or recording.

Figure 22C:
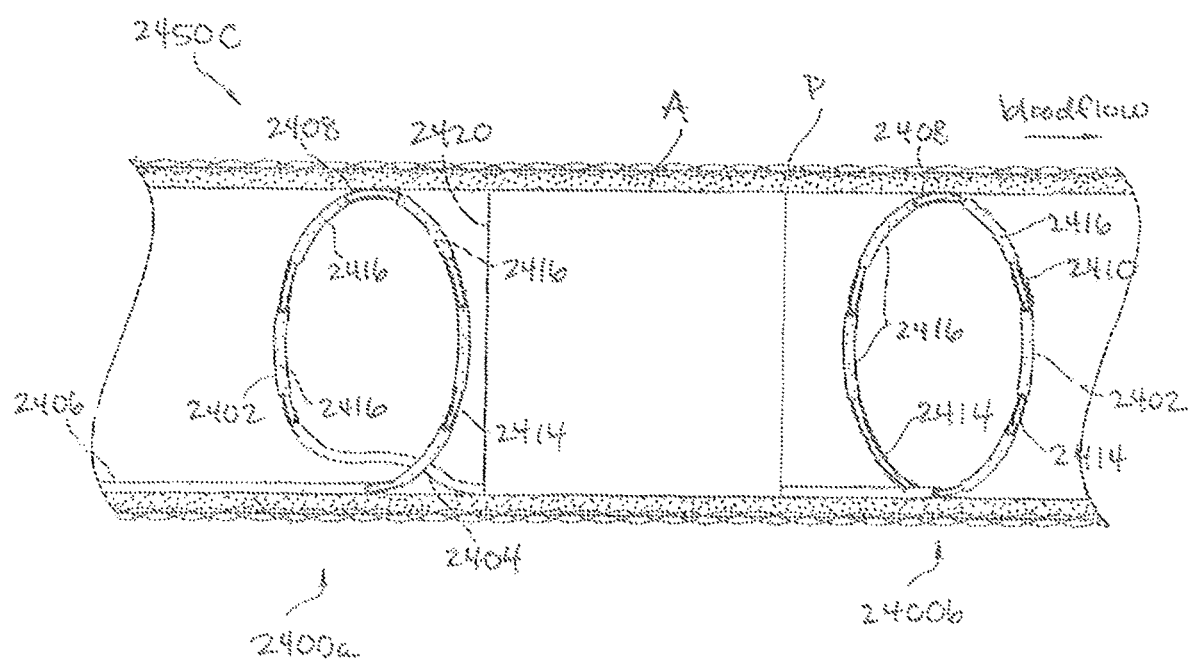
FIG. 22C is an enlarged partially schematic view of a distal portion of a treatment device within a blood vessel in accordance with yet another embodiment of the present technology.

FIG. 22C is an enlarged partially schematic side view of a distal portion of a treatment device 2450C within a blood vessel A (e.g., a pulmonary blood vessel) in accordance with yet another embodiment of the present technology. The treatment device 2450C includes features generally similar to the features of the treatment device 2450B described above with reference to FIG. 22B. For example, the treatment device 2450C includes the therapeutic assembly 2420 positioned between the first electrode assembly 2400a and the second electrode assembly 2400b. In the embodiment illustrated in FIG. 22C, however, the first electrode assembly 2400a includes only one multi-electrode loop 2402 such that the loop 2402 includes both anodes and cathodes to provide the desired bipolar stimulation.

FIG. 23 is an enlarged partially schematic side view of a distal portion of a treatment device 2550 within a blood vessel A (e.g., a pulmonary blood vessel) in accordance with a further embodiment of the present technology. The treatment device 2550 includes features generally similar to the features of the treatment devices described above with reference to FIGS. 21B, 22B and 22C. The treatment device 2550, for example, includes a therapeutic assembly 2520 (shown schematically) and a nerve monitoring assembly 2530 at a distal portion 2512 of a shaft 2506. The therapeutic assembly 2520 is positioned between a first electrode assembly 2500a that provides bipolar nerve stimulation and a second electrode 2500b that provides bipolar recording of nerve activity (collectively referred to as electrode assemblies 2500). In the illustrated embodiment, each electrode assembly 2500 includes a balloon 2532 (identified individually as a first balloon 2532a and a second balloon 2532b) having one or more conductive portions 2534 (identified individually as a first conductive portion 2534a and a second conductive portion 2534b) that serve as electrodes. The conductive portions 2534 can be made from a conductive ink that is sufficiently flexible to allow the balloons 2532 to fold into a guide catheter (not shown) during delivery and removal of the treatment device 2550. In other embodiments, the conductive portions 2534 can be made from other suitable materials that attach to the balloons 2532, such as platinum iridium wires.

In the embodiment illustrated in FIG. 23, each balloon 2532 includes two spaced apart conductive portions 2534 around at least a portion of the circumference of the balloon 2532 such that the conductive portions 2534 can contact the inner wall of the blood vessel A when the balloons 2532 are inflated (e.g., as shown in FIG. 23). The balloons 2532 can be inflated by flowing gas (e.g., air) or liquid (e.g., saline solution) into the balloons 2532 through one or more openings 2537 (referred to individually as a first opening 2537a and a second opening 2537b) in a tube 2535 that is coupled to a fluid source (not shown) at a proximal end portion and extends through the balloons 2532 at a distal end portion. Similar to the multi-loop electrode assemblies described above, the two conductive portions 2534 of each balloon 2532 can be designated as an anode and as a cathode to provide bipolar nerve stimulation and recording. In other embodiments, at least one of the electrode assemblies 2500 can include a dual balloon, and each balloon can include one conductive portion 2534 such that the nerve monitoring assembly 2530 includes three or four balloons.

In various embodiments, the therapeutic assembly 2520 can be omitted. As such, the electrode assemblies 2500 can be intravascularly delivered to the treatment site (e.g., at the pulmonary vessel) to record nerve activity before neuromodulation. The electrode assemblies 2500 can then be removed from the target site to allow the therapeutic assembly 2520 to be delivered. After neuromodulation, the electrode assemblies 2500 can be delivered back to the target site to record the nerve activity. If a sufficient nerve lesion has not been formed, the therapeutic assembly 2520 can again be delivered to the treatment site to deliver an energy field to ablate or otherwise modulate the nerves. The therapeutic assembly 2520 can then be removed from the treatment site to allow the electrode assemblies 2500 to be delivered and monitor the resultant nerve activity. This process can be repeated until a sufficient nerve lesion is formed at the target site.

FIG. 24 is an enlarged side view of a distal portion of a treatment device 2650 within a blood vessel A (e.g., a pulmonary blood vessel) in accordance with yet another embodiment of the present technology. The treatment device 2650 includes a number of features generally similar to the features of the treatment devices described above with reference to FIGS. 21B, 22B, 22C and 23. For example, the treatment device 2650 includes an array of electrodes (identified individually as a first electrode array 2600a and a second electrode array 2600b, and referred to collectively as electrode arrays 2600) proximal and distal to a neuromodulation area. 2643 (shown in broken lines). In the embodiment illustrated in FIG. 24, the treatment device 2650 has a double balloon configuration in which a first inflatable body or outer balloon 2640 is disposed over a second inflatable body or inner balloon 2642. The inner balloon 2642 can be configured to deliver therapeutic neuromodulation to nerves proximate a treatment site (e.g., a pulmonary blood vessel). For example, the inner balloon 2642 can define an expansion chamber in which a cryogenic agent (e.g., nitrous oxide ($N_2O$)) can expand to provide therapeutically-effective cooling to tissue adjacent to the inflated inner balloon 2642 (e.g., in the neuromodulation area 2643). In other embodiments, the inner balloon 2642 can be configured to provide therapeutic neuromodulation using other suitable means known in the art such as ultrasound (e.g., HIFU). In further embodiments, the inner balloon 2642 may be omitted, and energy deliver elements (e.g., electrodes) can be disposed on an outer surface of the outer balloon 2640 to deliver RF ablation energy and/or other forms of energy for neuromodulation.

As shown in FIG. 24, a proximal end portion of the outer balloon 2640 can be coupled to a distal portion 2612 (also 2812, see also FIG. 26) of an outer shaft 2606 (also 2806, see also FIG. 26) and a proximal end portion of the inner balloon 2642 can be coupled to an inner shaft 2644 that extends through the outer shaft 2606. In the illustrated embodiment, the inner shaft 2644 extends through the outer and inner balloons 2640 and 2642 such that the distal end portions of the outer and inner balloons 2640 and 2642 can connect thereto, and therefore the inner shaft 2644 can provide longitudinal support along the balloons 2640 and 2642. In other embodiments, the inner shaft 2644 can extend partially into the balloons 2640 and 2642 or terminate proximate to the distal end of the outer shaft 2606. The outer and inner shafts 2606 and 2644 can define or include supply lumens fluidly coupled at proximal end portions to one or more fluid sources and fluidly coupled at distal end portions to the outer and inner balloons 2640 and 2642. For example, the inner shaft 2644 can include one or more openings 2646 through which fluids (e.g., refrigerants or other cryogenic agents) can be delivered to the inner balloon 2642 (e.g., as indicated by the arrows) to inflate or expand the inner balloon 2642. Fluids (e.g., saline or air) can be delivered to the outer balloon 2640 through a space or opening 2646 between the outer and inner shafts 2606 and 2644 (e.g., as indicated by the arrows) and/or by a supply lumen spaced therebetween to inflate or expand the outer balloon 2640.

The inner balloon 2642 can have smaller dimensions than the outer balloon 2640 such that the outer balloon 2640 expands into full circumferential contact with the vessel wall along a length of the vessel and the inner balloon 2642 expands to press against or otherwise contact a segment of the inner wall of the outer balloon 2640. In the embodiment illustrated in FIG. 24, for example, the outer and inner balloons 2640 and 2642 contact each other at an interface extending around a full circumference of the inner balloon 2642 spaced laterally inward of the electrode arrays 2600. The portion of the outer balloon 2640 in contact with the inflated inner balloon 2642 can deliver therapeutically-effective neuromodulation (e.g., via cryotherapeutic cooling) to nerves proximate the adjacent vessel wall. Accordingly, the double balloon arrangement shown in FIG. 24 can deliver fully-circumferential neuromodulation. Non-targeted tissue proximal and distal to the contacting balloon walls is shielded or protected from neuromodulation by an inflation medium (e.g., saline solution, air, etc.) within the outer balloon 2640, which may effectively act as insulation.

The outer and inner balloons 2640 and 2642 can be made from various compliant, non-compliant, and semi-compliant balloons materials. The outer balloon 640, for example, can be made from a compliant balloon material (e.g., polyurethane or silicone) such that when the outer balloon 2640 is inflated, it can press against the inner wall of a vessel to provide stable contact therebetween. The inner balloon 2642 can be made from semi-compliant and or non-compliant materials (e.g., formed from polyether block amide, nylon, etc.) to define a smaller expanded size. In other embodiments, the outer and inner balloons 2640 and 2642 can be made from other suitable balloon materials.

As shown in FIG. 24, the first electrode array 2600a and the second electrode array 2600b may be located at the outer wall of the outer balloon 2640 and positioned proximal and distal to the neuromodulation area 2643 (i.e., the region of the outer balloon 2640 that contacts the inflated inner balloon 2642). Each electrode array 2600 (also 2800, see also FIG. 26) can include a first conductive portion 2634a (also 2834a, see also FIG. 26) and a second conductive portion 2634b also 2834b, see also FIG. 26) (referred to collectively as conductive portions 2634 (2834)) that extend around the circumference of the outer balloon 2640 (2840) to define first and second electrode loops. In other embodiments, one or both of the electrode arrays 2600 can include a single conductive portion or strip extending around the circumference of the outer balloon 2640. The conductive portions 2634 can be made from a conductive ink printed on the outer wall of the outer balloon 2640 and/or other conductive materials that can attach to the outer balloon 2640. In operation, the first electrode array 2600a can stimulate nerves proximal to the neuromodulation area 2643 and the second electrode array 2600b can sense the resultant stimulation, or vice versa. The first and second conductive portions 2634 of each electrode array 2600 can be configured to provide bipolar or monopolar stimulation and/or recording depending upon which mode provides the highest signal response. For example, the first electrode array 2600a can include one electrode (e.g., one conductive strip 2634) for monopolar stimulation and the second electrode array 2600b can include two electrodes (e.g., two conductive strips 2634) for bipolar recording. In other embodiments, however, the electrode arrays 2600 may have other arrangements and/or include different features.

The treatment device 2650 can provide nerve stimulation and recording before, during, and/or after neuromodulation. For example, the electrode assemblies 2600 can stimulate nerves and record the resultant nerve activity before neuromodulation to provide a set point against which subsequent nerve monitoring can be compared. This information can also be used to determine the level of power or current that must be delivered to ablate the nerves since each patient typically has different base line levels nerve activity. Therefore, the electrode arrays 2600 can also provide diagnostic nerve monitoring. During the neuromodulation procedure, the electrode arrays 2600 can monitor the reduction of nerve signal strength to confirm the effectiveness of the neuromodulation. For example, the electrode assemblies 2600 can continually monitor nerve activity during neuromodulation by interleaving stimulation pulses and recording periods. In other embodiments, nerve monitoring periods can be spaced between neuromodulation periods to determine whether the nerves have been sufficiently modulated or if subsequent neuromodulation cycles are necessary to provide the desired modulation.

Figure 25:
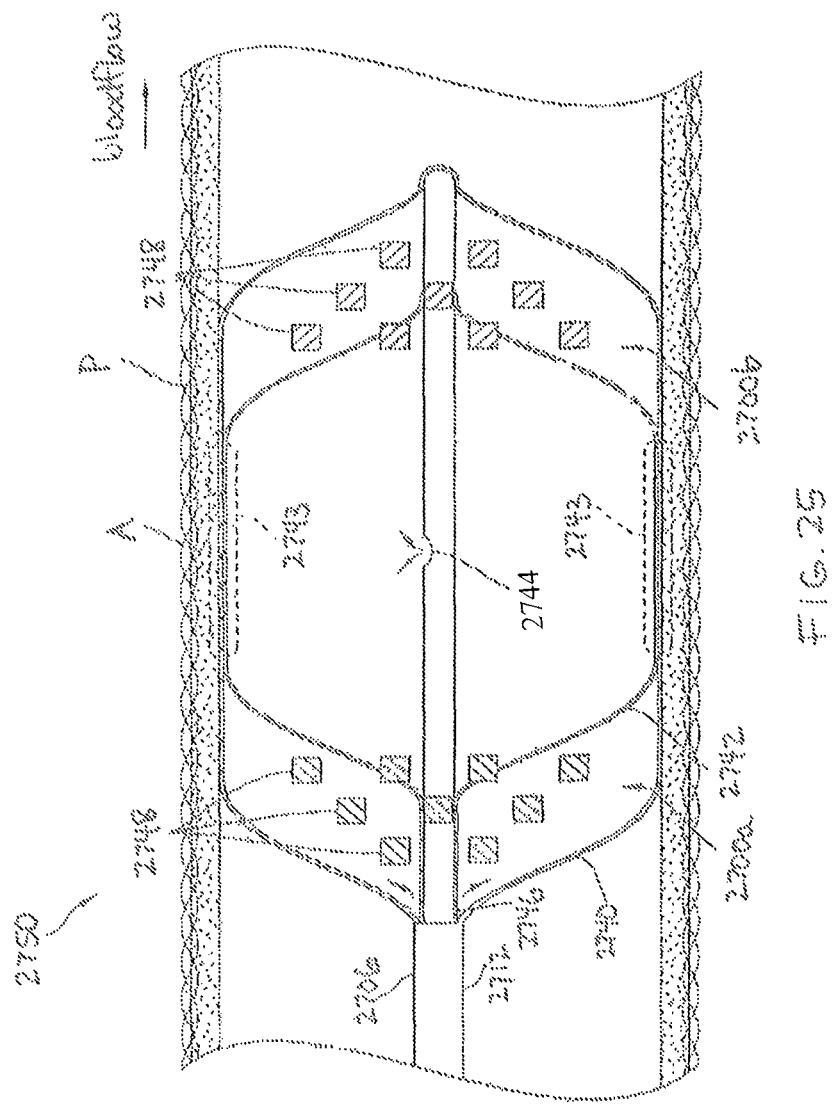
FIG. 25 is an enlarged side view of a distal portion of a treatment device within a blood vessel in accordance with a further embodiment of the present technology.

FIG. 25 is an enlarged side view of a distal portion of a treatment device 2750 within a blood vessel A (e.g., a pulmonary blood vessel) in accordance with a further embodiment of the present technology. The treatment device 2750 includes a number of features generally similar to the features of the treatment device 2650 described above with reference to FIG. 24. For example, the treatment device 2750 includes an outer balloon 2740 in fluid communication with a first supply lumen via an opening 2746 at a distal portion 2712 of an outer shaft 2706, and an inner balloon 2742 in fluid communication with a second supply lumen via an opening 2746 of an inner shaft 2744. The outer balloon 2740 can be inflated with a non-therapeutically effective fluid (e.g., air) to press against and maintain contact with the inner vessel wall. The inner balloon 2742 can be inflated with a cryogenic agent (e.g., a refrigerant) and/or other fluid to contact a portion of the outer balloon 2740 and provide neuromodulation (e.g., via cryotherapeutic cooling or ultrasound) about the full circumference of an adjacent vessel wall (e.g., within a neuromodulation region 2743).

The treatment device 2750 also includes first and second electrode arrays 2700a and 2700b (referred to collectively as electrode arrays 2700) proximal and distal to the portion at which the inner balloon 2742 contacts the outer balloon 2740. Rather than continuous conductive strips around the circumference of the outer balloon 2740, however, the electrode arrays 2700 illustrated in FIG. 25 include a plurality of point electrodes 2748 on or in an outer wall of the outer balloon 2740. The point electrodes 2748, for example, can be made from conductive ink printed on the outer balloon 2740, conductive pads adhered to the outer balloon 2740, and/or other suitable conductive features. The individual point electrodes 2748 can be oriented about the circumference of the outer balloon 2740 in various different patterns and provide monopolar and/or bipolar nerve stimulation and recording before, during and/or after neuromodulation.

Figure 26:
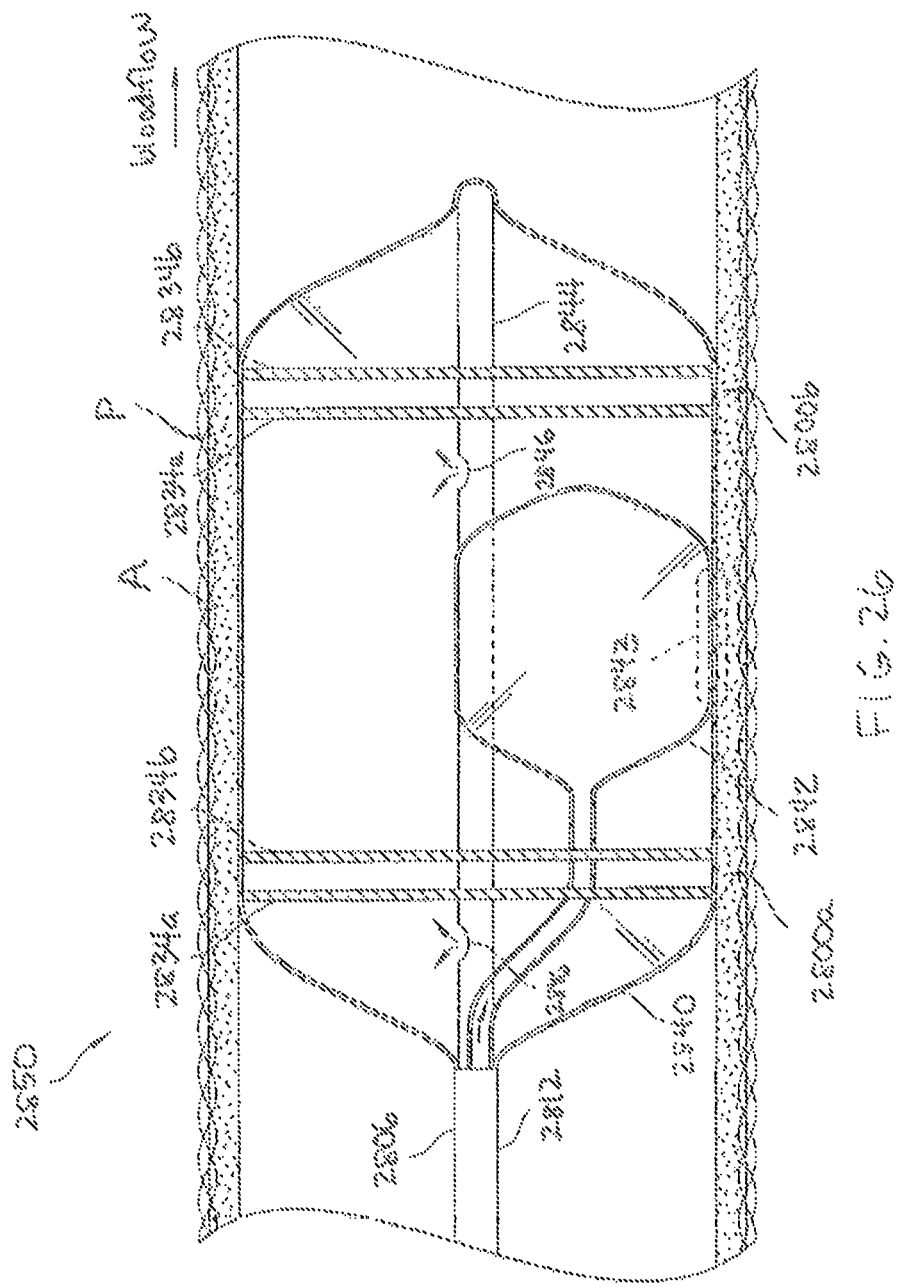
FIG. 26 is an enlarged side view of a distal portion of a treatment device within a blood vessel in accordance with an additional embodiment of the present technology.

FIG. 26 is an enlarged side view of a distal portion of a treatment device 2850 within a blood vessel A (e.g., a pulmonary blood vessel) in accordance with an additional embodiment of the present technology. The treatment device 2850 includes several features generally similar to the features of the treatment device 2650 described above with reference to FIG. 24. For example, the treatment device 2850 includes first and second electrode arrays 2800a and 2800b (referred to collectively as electrode arrays 2800) on an outer balloon 2840 and positioned proximal and distal to a neuromodulation region 2843 provided by an inner balloon 2842. In the embodiment illustrated in FIG. 26, the inner balloon 2842 has a smaller outer diameter in an inflated state than that of the outer balloon 2840 and is attached to an interior surface of the outer balloon 2840 using an adhesive, a heat-bond and/or other types of balloon connection. The outer balloon 2840 can be fluidly coupled to a supply lumen defined by a shaft 2844 that delivers an insulative medium (e.g., a heated liquid, heated gas, ambient air, etc.) to the outer balloon 2840 via openings 2846, and the inner balloon 2842 can be fluidly coupled to a separate supply lumen (not shown) that delivers an inflation fluid (e.g., a cryogenic agent) to the inner balloon 2842.

In use, the outer balloon 2840 expands into full circumferential contact with the vessel wall to provide tissue apposition for signal transfer to and from the vessel wall via the electrode arrays 2800. The inner balloon 2842 is essentially radially pulled toward only the portion of the vessel wall adjacent to where the inner balloon 2842 is attached to the outer balloon 2840. When a cryogenic agent and/or other therapeutic medium is introduced into the inner balloon 2842, non-targeted tissue that is not adjacent to the inner balloon 2842 is shielded or protected from ablation by the inflation medium located within the outer balloon 2840. The targeted tissue adjacent to the inner balloon 2842 is ablated, resulting in a partial circumferential neuromodulation. The inner balloon 2842 can be shaped or otherwise configured to provide a non-continuous, helical, and/or other type of ablation pattern.

Figure 27:
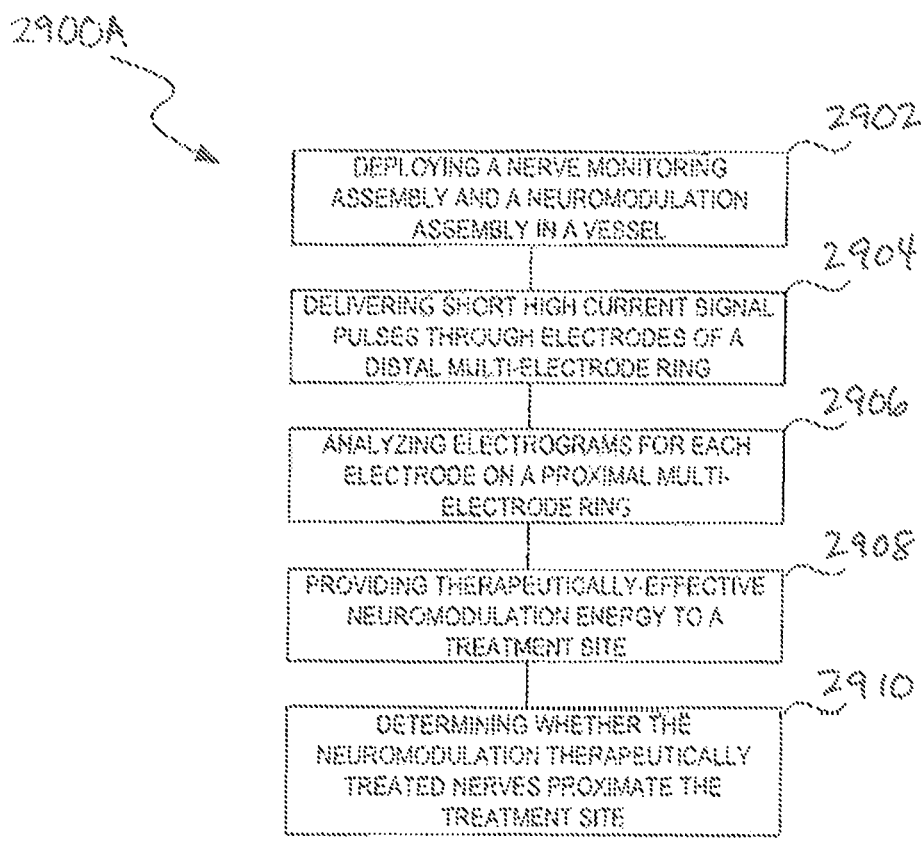
FIG. 27 is a block diagram illustrating a method of endovascularly monitoring nerve activity in accordance with an embodiment of the present technology.

FIG. 27 is a block diagram illustrating a method 2900A of endovascularly monitoring nerve activity in accordance with an embodiment of the present technology. The method 2900A can include deploying a nerve monitoring assembly and a therapeutic assembly in a vessel (e.g., a pulmonary blood vessel; block 2902). The nerve monitoring assembly can include a plurality of multi-electrode rings (e.g., similar to the multi-electrode loops 2402 described above with reference to FIGS. 22A-22C) connected to a distal portion of a catheter shaft. The multi-electrode rings can be made of nitinol or other shape memory materials such that they can be deployed by simply moving the catheter shaft and a sheath covering the multi-electrode rings relative to one another (e.g., pulling the sheath proximally, pushing the catheter shaft distally, etc.). Each multi-electrode ring can include a plurality of electrodes spaced around the circumference of the ring and communicatively coupled to signal wires extending through the catheter shaft. The signal wires can extend outside the body where they are operably coupled to a signal generator and/or receiver (e.g., an NIM) to generate stimuli and record the resultant action potential of the proximate neural fibers.

When the therapeutic assembly is deployed, at least one and often two or more multi-electrode rings ("distal rings") or another distal electrode assembly can be positioned distal to the therapeutic assembly and at least one multi-electrode ring ("proximal ring") or other proximal electrode assembly can be positioned proximal to the therapeutic assembly. In other embodiments, the nerve monitoring assembly can include one, two, or more multi-electrode rings on either side of the therapeutic assembly. In further embodiments, other types of electrode arrays can be positioned proximal and distal to the therapeutic assembly. The therapeutic assembly, such as a single- or multi-electrode device or a cryoballoon, can be integrated with the same catheter shaft as the multi-electrode rings and positioned between the proximal and distal rings. In other embodiments, the therapeutic assembly can be attached to a separate catheter shaft and deployed between proximal and distal multi-electrode rings.

The method 2900A can further include delivering a plurality of short, high current stimulus pulses through the electrodes on one or both of the multi-electrode rings positioned distal to the therapeutic assembly (block 2904), and analyzing an electrogram of at least one of the electrodes on the proximal ring resulting from the stimulus pulse (block 2906). For example, a signal generator can pass a current having a magnitude of about 10-60 mA (e.g., 20 mA, 50 mA, etc.) for a pulse length of about 25-1,500 μs (e.g., 100-400 μs, 1 ms, etc.) between the electrodes of the distal rings in the delivering process 2904. The signal generator can also control the frequency of the signal such that the signal has a frequency of about 10-50 Hz (e.g., 20 Hz). After a predetermined time interval, a separate electrogram can be recorded through at least one electrode on the proximal ring. For example, a separate electrogram can be recorded through each of the electrodes of the proximal electrode ring. The length of the time interval between stimulation and recording depends on the separation of the distal and proximal rings along the length of the vessel such that the proximal ring picks up the signal resulting from the induced stimulus. For example, the time interval can be about 10-50 ms for rings spaced 10-50 mm apart. In an alternative embodiment, the delivering process (block 2904) of the method 2900A can include delivering the short, high current stimulus pulses through at least one of the proximal electrode rings (e.g., proximal electrode assembly), and the analyzing process (block 2906) of the method 2900A can include analyzing an electrogram of at least one of the electrodes of the distal electrode rings (e.g., distal electrode assembly).

The method 2900A can further include providing therapeutically-effective neuromodulation energy (e.g., cryogenic cooling, RF energy, ultrasound energy, etc.) to a target site using the therapeutic assembly (block 2908). After providing the therapeutically-effective neuromodulation energy (block 2908), the method 2900A includes determining whether the neuromodulation therapeutically treated or otherwise sufficiently modulated nerves or other neural structures proximate the treatment site (block 2910). For example, the process of determining whether the neuromodulation therapeutically treated the nerves can include determining whether nerves were sufficiently denervated or otherwise disrupted to reduce, suppress, inhibit, block or otherwise affect the afferent and/or efferent pulmonary signals.

Figure 28:
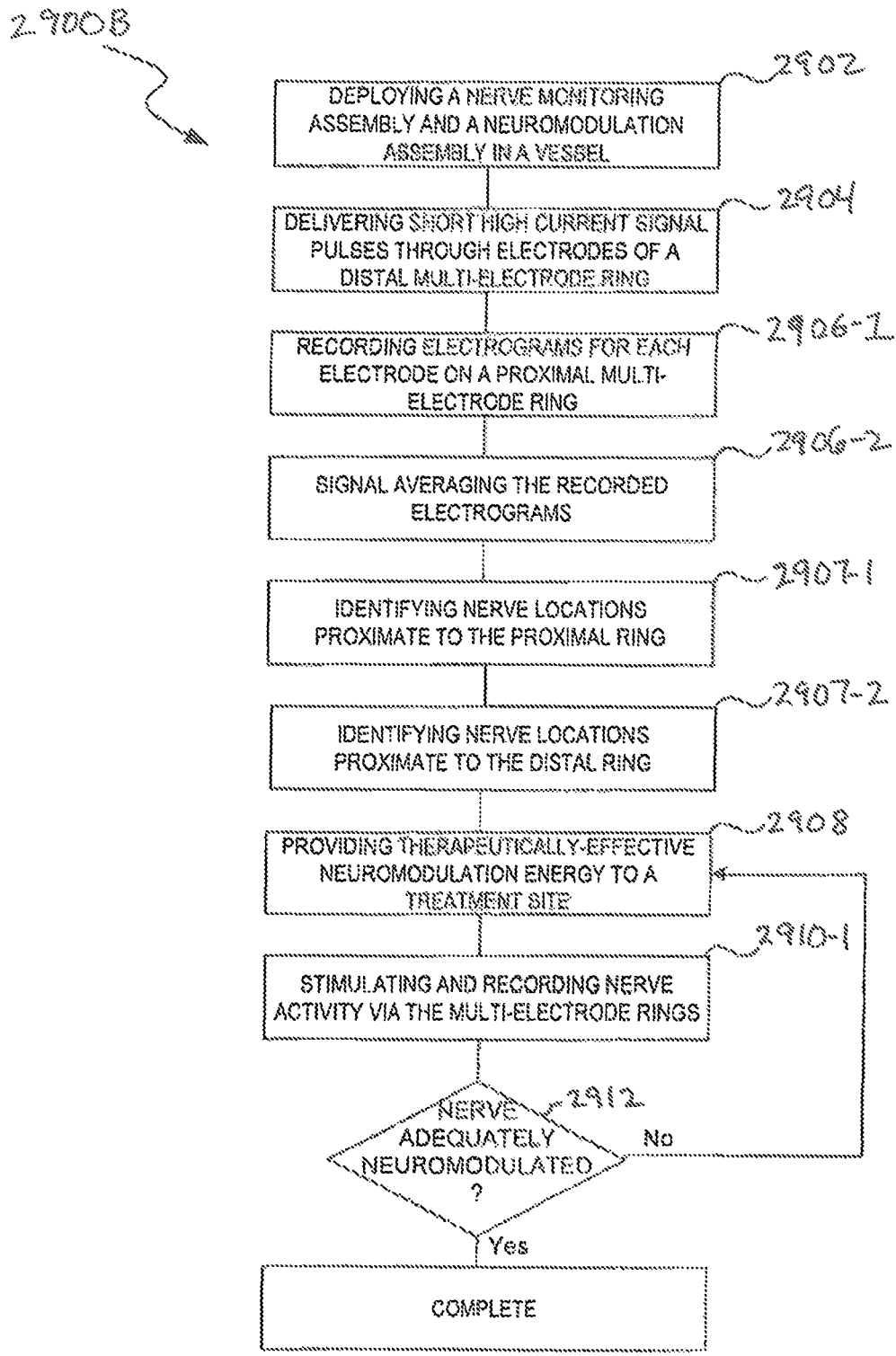
FIG. 28 is a block diagram illustrating a method of endovascularly monitoring nerve activity in accordance with another embodiment of the present technology.

FIG. 28 is a block diagram illustrating a method 2900B of endovascularly monitoring nerve activity in accordance with an embodiment of the present technology. The method 2900B can include deploying a nerve monitoring assembly and a therapeutic assembly in a vessel (block 2902) and delivering short, high current signal pulses through an electrode assembly (block 2904) as described above with respect to the method 2900A in FIG. 27. In this embodiment, the analyzing process (block 2906 of FIG. 27) can optionally include recording the electrograms for each electrode on the proximal electrode ring or other proximal electrode assembly (block 2906-1) and signal averaging a plurality of the recorded electrode signals (e.g., 10-100 recorded electrode signals) resulting from a corresponding plurality of stimulus pulses to enhance the recorded signal (block 2906-2).

The method 2900B can optionally include identifying the nerve location proximate one or more of the electrode rings. For example, one or more of the recorded electrode signals may include a deflection or other change in the recorded current indicating an action potential caused by the stimulus (e.g., identified via signal averaging) indicating the transmission of an electrical impulse from the stimulus pulse via adjacent nerves. Electrode signals that include changes in current intensity correspond with the electrodes on the proximal ring positioned proximate to nerves. The higher the deflection or change in current intensity, the closer the electrode is to the nerves. This information can be used to identify electrodes on the proximal ring close to the nerves for effective nerve stimulation or recording (block 2907-1). Optionally, the method 2900 can include stimulating nerves via the proximal ring and recording electrograms of the individual electrodes at one of the distal rings to determine the location of nerves proximate the distal rings (block 2907-2).

The method 2900B can also include providing therapeutically-effective neuromodulation energy (e.g., cryogenic cooling, RF energy, ultrasound energy, etc.) to a target site using the therapeutic assembly (block 2908). In this embodiment, the process of determining whether the neuromodulation treated the nerves proximate the target site (block 2910 in FIG. 27) can include repeating the nerve stimulation (block 2904) and analyzing processes (block 2906) discussed above to assess whether the neuromodulation caused any changes in the nerve activity (block 2910-1). For example, short, high current stimulus pulses can be transmitted via the proximal or distal rings and the resultant nerve activity can be recorded by the opposing ring(s). The method 2900B can then determine whether the nerves have been adequately modulated (block 2912). For example, if the current density or other parameter observed in the recording electrodes proximate the nerve locations is below a threshold value, then the neuromodulation step may have effectively modulated or stopped conduction of the adjacent nerves and the neuromodulation process can be complete. On the other hand, if nerve activity is detected above a threshold value, the process of neuromodulating (block 2908) and monitoring the resultant nerve activity (block 2910-1) can be repeated until the nerves have been effectively modulated.

In various embodiments, the methods 2900A and 2900B can also include repeating the nerve monitoring and neuromodulation steps in the opposite direction to confirm that the nerves have been adequately modulated. The methods 2900A and 2900B can also optionally be repeated after a time period (e.g., 5-30 minutes, 2 hours, 1 day, etc.) to confirm that the nerves were adequately ablated (e.g., rather than merely stunned) and have not resumed conduction.

In other embodiments, the methods 2900A and 2900B can be performed using other nerve monitoring assemblies or electrode arrays described above with reference to FIGS. 21A-28 and/or other suitable electrode arrangements. For example, the therapeutic assembly can include multiple point electrodes spaced around the circumference of a balloon as described above with respect to FIG. 26. In other embodiments, continuous wire loop electrodes and/or conductive strips on balloons can be used to identify nerve location and monitor nerve activity.

III. EXAMPLES

1. A catheter apparatus, comprising:
    an elongated shaft having a proximal portion and a distal portion, wherein the distal portion of the shaft is configured for intravascular delivery to a body vessel of a human patient;
    an energy delivery element positioned along the distal portion of the shaft; and
    a plurality of deflectable members spaced apart about a circumference of the distal portion of the shaft, wherein each of the deflectable members is configured to transform from a low-profile state to a deployed state, thereby bending the distal portion and placing the energy delivery element in apposition with a wall of the body vessel.

2. The catheter apparatus of example 1 wherein the distal portion of the elongated shaft is sized and configured for intravascular delivery into the pulmonary artery.

3. The catheter apparatus of example 1 or example 2 wherein the each of the deflectable members comprises a bimetallic strip including a first material having a first coefficient of thermal expansion (CTE) positioned adjacent a second material having a second CTE that is different than the first CTE.

4. The catheter apparatus of any of examples 1-3 wherein each of the deflectable members comprises a bimetallic strip including a piezoelectric material and a substrate material coupled to one another along their lengths, wherein the piezoelectric material has a first CTE and the substrate material has a second CTE that is different than the first CTE.

5. The catheter apparatus of any of examples 1-4 wherein the therapeutic assembly comprises four deflectable members, wherein each of the deflectable members corresponds to a distinct quadrant of the shaft.

6. The catheter apparatus of any of examples 1-5 wherein the deflectable members extend along a length of the shaft and have a proximal terminus within the distal portion of the elongated shaft.

7. The catheter apparatus of any of examples 1-6 wherein the deflectable members have a length less than a length of the elongated shaft and a proximal terminus spaced distally apart from a proximal portion of the shaft.

8. The catheter apparatus of any of examples 1-7 wherein the deflectable members have distal terminus spaced proximally of the energy delivery device and a proximal terminus within the distal portion of the elongated shaft.

9. The catheter apparatus of any of examples 1-8 wherein the energy delivery element is a single energy delivery element positioned at a distal terminus of the shaft.

10. The catheter apparatus of any of examples 1 and 3-10 wherein the distal portion of the elongated shaft is sized and configured for intravascular delivery into the renal artery.

11. The catheter apparatus of any of examples 1-10, further comprising a handle at the proximal portion of the shaft, the handle including an actuator that is electrically coupled to each of the deflectable members, and wherein the deflectable members are independently transformable between their respective low-profile states and deployed states by activating the actuator.

12. The catheter apparatus of any of examples 1-11 wherein the energy delivery element is spaced apart from the deflectable members along the shaft.

13. The catheter apparatus of any of examples 1-11 wherein the energy delivery element is positioned on one or more of the deflectable members.

14. The catheter apparatus of any of examples 1-13 wherein the energy delivery element is a first energy delivery element, and wherein the catheter apparatus further comprises a second delivery element.

15. A catheter apparatus, comprising:
an elongated shaft having a proximal portion and a distal portion, wherein the distal portion of the shaft is configured for intravascular delivery to a body vessel of a human patient;
a deflectable member at the distal portion of the shaft and electrically coupled to the proximal portion, wherein the deflectable member comprises a bimetallic strip including a first material having a first CTE positioned adjacent a second material having a second CTE that is different than the first CTE; and
an energy delivery element on the deflectable member,
wherein heating the deflectable member deforms the deflectable member, thereby placing the energy delivery element in apposition with a wall of the body vessel.

16. The catheter apparatus of example 15 wherein the energy delivery element is a first energy delivery element, and wherein the catheter apparatus further comprises a second delivery element on the deflectable member.

17. The catheter apparatus of example 15 or example 16 wherein the energy delivery element is in direct contact with the deflectable member.

18. The catheter apparatus of any of examples 15-17 wherein the deflectable element is a first deflectable element, and wherein the catheter apparatus further comprises a second deflectable element.

19. A method, comprising:
intravascularly positioning a therapeutic assembly at a treatment site within a blood vessel, wherein the therapeutic assembly includes a deflectable member and an energy delivery element;
heating the deflectable member to position the energy delivery element in apposition with the blood vessel wall; and
ablating nerves proximate the treatment site via the energy delivery element.

20. The method of example 19 wherein intravascularly positioning the therapeutic assembly includes intravascularly positioning the therapeutic assembly within a pulmonary blood vessel.

21. The method of example 19 wherein intravascularly positioning the therapeutic assembly includes intravascularly positioning the therapeutic assembly within a renal blood vessel.

22. A treatment device, comprising:
a shaft including a proximal portion and a distal portion, wherein the shaft is configured to intravascularly locate the distal portion at a treatment site within a pulmonary blood vessel of a human patient;
a balloon at the distal portion of the shaft;
a lumen extending distally from a proximal portion of the shaft to an output port at the distal portion, wherein the output port is positioned along a portion of the shaft within the balloon, and wherein the output port is configured to deliver a cooling agent to an interior portion of the balloon;
a first electrode positioned on the outer surface of the balloon and extending about at least a portion of the circumference of the balloon;
a second electrode positioned on the outer surface of the balloon and extending about at least a portion of the circumference of the balloon, wherein the first electrode is spaced apart from and out of contact with the second electrode along the balloon;
wherein the first and second electrodes are configured to—
deliver therapeutic neuromodulation to nerves in communication with the pulmonary system proximate the treatment site, and
stimulate nerves and/or record nerve activity at the treatment site.

23. The treatment device of example 22 wherein the first electrode is configured to stimulate nerves proximate the treatment site and the second electrode is configured to record nerve activity at the treatment site during and/or after the therapeutic neuromodulation.

24. The treatment device of example 22 or example 23, further comprising an insulated portion between the first electrode and the second electrode on the outer surface of the balloon.

25. The treatment device of any of examples 22-24 wherein:
the first electrode is configured to deliver energy sufficient to modulate the nerves in communication with the pulmonary system; and
the second electrode is configured for bipolar recording of renal nerve activity before, during, and/or after energy application.

26. The treatment device of any of examples 22-25 wherein the lumen is a first lumen, and wherein the shaft further includes a second lumen extending distally to an inlet port positioned along a portion of the shaft within the balloon.

27. The treatment device of any of examples 22-26 wherein at least one of the first and second electrodes includes a multi-electrode loop having at least two electrodes spaced circumferentially about the loop.

28. The treatment device of any of examples 22-27 wherein at least one of the first electrode and the second electrode is configured to deliver radio frequency (RF) energy sufficient to ablate nerves in communication with the pulmonary system proximate the treatment site.

29. The treatment device of any of examples 22-28 wherein the balloon is transformable between a delivery state and a deployed state and wherein, in the deployed state, the balloon is sized and shaped to occlude the pulmonary blood vessel.

30. The treatment device of any of examples 22-29 wherein the balloon is transformable between a delivery state and a deployed state and wherein, in the deployed state, the balloon is sized and shaped to place the first electrode and second electrode in apposition with an inner wall of the pulmonary blood vessel.

31. A method, comprising:
intravascularly deploying a treatment device in a pulmonary blood vessel of a human patient at a treatment site, wherein the treatment device includes an elongated shaft, a balloon at a distal portion of the shaft, and first and second electrodes on an outer surface of the balloon;
ablating the renal nerves via radio frequency (RF) energy delivered from the first electrode and/or the second electrode;
before ablation, stimulating nerves in communication with the pulmonary system near the treatment site and recording the resulting nerve activity; and
after ablation, stimulating the nerves and recording the resulting nerve activity.

32. The method of example 31, further comprising confirming the effectiveness of the ablation on the nerves based on the post-ablation recording.

33. The method of example 31 or example 32 wherein stimulating the nerves in communication with the pulmonary system before and/or after ablation is performed by the first electrode and recording nerve activity before and/or after ablation is performed with the second electrode.

34. The method of any of examples 31-33 wherein:
stimulating the nerves in communication with the pulmonary system before and after ablation comprises providing bipolar stimulation to the nerves; and
recording nerve activity before and after ablation comprises providing bipolar recording of the nerve activity with the second electrode, wherein the second electrode is distal to the first electrode.

35. The method of any of examples 31-34 wherein:
stimulating the nerves in communication with the pulmonary system before and/or after ablation comprises delivering a plurality of stimulus pulses with the first electrode; and
recording nerve activity before and after ablation is performed by the second electrode, wherein recording comprises recording an electrogram of the second electrode and that corresponds to the nerve activity resulting from the corresponding stimulus pulses.

36. The method of any of examples 31-35 wherein deploying the treatment device includes deploying the first electrode proximal to the second electrode, wherein the first and second electrodes each comprise a loop electrode.

37. The method of any of examples 31-36 wherein deploying the treatment device in the pulmonary blood vessel comprises deploying the first electrode proximal to the second electrode.

38. The method of any of examples 31-37 wherein deploying the treatment device in the pulmonary blood vessel comprises inflating the balloon within a pulmonary artery, wherein the inflated balloon contacts an inner wall of the pulmonary artery.

39. The method of any of examples 31-38 wherein deploying the treatment device in the pulmonary blood vessel comprises inflating the balloon within a pulmonary artery, wherein the inflated balloon, the first electrode, and the second electrode contact an inner wall of the pulmonary artery.

40. The method of any of examples 31-39 wherein:
stimulating nerves after ablation and recording the resulting nerve activity is performed after delivering a first cycle of ablation to nerves in communication with the pulmonary system; and
the method further comprises delivering a second cycle of ablation to nerves in communication with the pulmonary system with the first and/or second electrodes when the recorded post-ablation nerve activity from the first cycle is above a predetermined threshold.

41. The method of any of examples 31-40 wherein recording nerve activity before and after ablation comprises providing bipolar recording of the nerve activity with the second electrode, wherein the second electrode is distal to the first electrode.

42. The method of any of examples 31-40 wherein recording nerve activity before and after ablation is performed by the second electrode, wherein recording comprises recording an electrogram of the second electrode and that corresponds to the nerve activity resulting from the corresponding stimulus pulses.

43. The method of any of examples 31-42 further comprising delivering a second cycle of ablation to nerves in communication with the pulmonary system with the first and/or second electrodes when the recorded post-ablation nerve activity from the first cycle is above a predetermined threshold.

IV. CONCLUSION

Although many of the embodiments are described below with respect to systems, devices, and methods for PN, the technology is applicable to other applications such as modulation of other nerves that communicate with the renal system, modulation of peripheral nerves, and/or treatments other than neuromodulation. Any appropriate site within the body may be modulated or otherwise treated including, for example, the pulmonary inflow tract, pulmonary veins, pulmonary arteries, the carotid artery, renal arteries and branches thereof. In some embodiments, cardiac tissue (e.g., the left and/or right atrium of the heart) may be modulated (e.g., to modulate electrical signals). Moreover, as further described herein, while the technology may be used in helical or spiral neuromodulation devices, it may also be used in non-helical or non-spiral neuromodulation devices as appropriate. Furthermore, other embodiments in addition to those described herein are within the scope of the technology. For example, in some embodiments the therapeutic assembly can include an expandable basket structure having one or more energy delivery elements positioned on the arms of the basket. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-28.

Although many embodiments of the present technology are described for use in an intravascular approach, it is also possible to use the technology in a non-vascular approach, such as a cutaneous and/or transcutaneous approach to the nerves that innervate the pulmonary system. For example, the vagal and phrenic nerves may lie outside the lungs (e.g., in the neck region and/or in the inlet to the thoracic cavity) at various locations that may render them amenable to access via cutaneous puncture or to transcutaneous denervation. As such, devices and/or methods described herein may be used to effect modulation of vagal and/or phrenic nerves from within a carotid vein and/or a jugular vein. Neuromodulation at one or both of those locations may be effective (e.g., may provide a therapeutically beneficial effect with respect to treating pulmonary hypertension).

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A catheter apparatus, comprising:
   an elongated shaft having a proximal portion and a distal portion, wherein the distal portion of the elongated shaft is configured for intravascular delivery to a body vessel of a human patient;
   an energy delivery element positioned along the distal portion of the elongated shaft; and
   a plurality of deflectable members spaced apart about a circumference of the distal portion of the elongated shaft, wherein each of the plurality of deflectable members has a bimetallic strip including a first material, a second material and a wire that runs in between and contacts the first material and the second material, and is configured to transform from a low-profile state to a deployed state, thereby bending the distal portion of the elongated shaft and placing the energy delivery element in apposition with a wall of the body vessel of the human patient when a current first flows through the wire and heats the first material and the second material.

2. The catheter apparatus of claim 1 wherein the distal portion of the elongated shaft is sized and configured for intravascular delivery into a pulmonary artery.

3. The catheter apparatus of claim 1 wherein the first material has a first coefficient of thermal expansion (CTE) and the second material has a second CTE that is different than the first CTE.

4. The catheter apparatus of claim 1 wherein the first material is a piezoelectric material having a length and the second material is a substrate material having a length, wherein the piezoelectric material and the substrate material are coupled to one another along their lengths, wherein the piezoelectric material has a first CTE and the substrate material has a second CTE that is different than the first CTE.

5. The catheter apparatus of claim 1 wherein the plurality of deflectable members include four deflectable members, wherein each of the four deflectable members corresponds to a distinct quadrant of the elongated shaft.

6. The catheter apparatus of claim 5 wherein the plurality of deflectable members extend along a length of the elongated shaft and have a proximal terminus within the distal portion of the elongated shaft.

7. The catheter apparatus of claim 1 wherein the plurality of deflectable members have a length less than a length of the elongated shaft and a proximal terminus spaced distally apart from the proximal portion of the elongated shaft.

8. The catheter apparatus of claim 1 wherein the plurality of deflectable members have a distal terminus spaced proximally of the energy delivery element and a proximal terminus within the distal portion of the elongated shaft.

9. The catheter apparatus of claim 1 wherein the energy delivery element is a single energy delivery element positioned at a distal terminus of the elongated shaft.

10. The catheter apparatus of claim 1 wherein the distal portion of the elongated shaft is sized and configured for intravascular delivery into a renal artery.

11. The catheter apparatus of claim 1, further comprising a handle at the proximal portion of the elongated shaft, the handle including an actuator that is electrically coupled to each of the plurality of deflectable members, and wherein the plurality of deflectable members are independently transformable between their respective low-profile states and deployed states by activating the actuator.

12. The catheter apparatus of claim 1 wherein the energy delivery element is spaced apart from the plurality of deflectable members along the elongated shaft.

13. The catheter apparatus of claim 1 wherein the energy delivery element is positioned on one or more of the plurality of deflectable members.

14. The catheter apparatus of claim 1 wherein the energy delivery element is a first energy delivery element, and wherein the catheter apparatus further comprises a second delivery element.

15. A catheter apparatus, comprising:
    an elongated shaft having a proximal portion and a distal portion, wherein the distal portion of the elongated shaft is configured for intravascular delivery to a body vessel of a human patient;
    a deflectable member at the distal portion of the elongated shaft and electrically coupled to the proximal portion of the elongated shaft, wherein the deflectable member comprises a bimetallic strip including a first material having a first CTE, a second material having a second CTE that is different than the first CTE and a wire that runs in between and contacts the first material and the second material; and
    an energy delivery element on the deflectable member, wherein a current first flows through the wire and heats the first material and the second material to deform the deflectable member, thereby placing the energy delivery element in apposition with a wall of the body vessel.

16. The catheter apparatus of claim 15 wherein the energy delivery element is a first energy delivery element, and wherein the catheter apparatus further comprises a second delivery element on the deflectable member.

17. The catheter apparatus of claim 15 wherein the energy delivery element is in direct contact with the deflectable member.

18. The catheter apparatus of claim 15 wherein the deflectable member is a first deflectable member, and wherein the catheter apparatus further comprises a second deflectable member.

* * * * *